(12) United States Patent
Paramithiotis et al.

(10) Patent No.: US 10,338,081 B2
(45) Date of Patent: Jul. 2, 2019

(54) TYPE 2 DIABETES BIOMARKERS AND USES THEREOF

(71) Applicants: Caprion Biosciences Inc., Montreal (CA); VAL-CHUM, Limited Partnership, Montreal (CA); Adaerata, Limited Partnership, Montreal (CA)

(72) Inventors: Eustache Paramithiotis, Boucherville (CA); Marc Prentki, Mount-Royal (CA); Rèmi Rabasa-Lhoret, Montreal (CA); Pascal Croteau, Laval (CA); Joel Lanoix, Montreal (CA); S.R. Murthy Madiraju, Brossard (CA); Èrik Joly, Blainville (CA)

(73) Assignees: Caprion Biosciences Inc., Montreal (CA); Adaerata, Limited Partnership, Montreal (CA); Val-Chum, Limited Partnership, Montreal (CA)

( * ) Notice: Subject to any disclaimer, the term of this patent is extended or adjusted under 35 U.S.C. 154(b) by 516 days.

(21) Appl. No.: 14/813,344

(22) Filed: Jul. 30, 2015

(65) Prior Publication Data
US 2015/0330997 A1 Nov. 19, 2015

Related U.S. Application Data

(63) Continuation of application No. PCT/IB2014/000426, filed on Jan. 31, 2014.

(60) Provisional application No. 61/758,987, filed on Jan. 31, 2013.

(51) Int. Cl.
*G01N 31/00* (2006.01)
*G01N 33/53* (2006.01)
*G01N 33/68* (2006.01)

(52) U.S. Cl.
CPC ..... *G01N 33/6893* (2013.01); *G01N 2500/00* (2013.01); *G01N 2560/00* (2013.01); *G01N 2570/00* (2013.01); *G01N 2800/042* (2013.01); *G01N 2800/50* (2013.01); *G01N 2800/52* (2013.01)

(58) Field of Classification Search
None
See application file for complete search history.

(56) References Cited

U.S. PATENT DOCUMENTS

2008/0200568 A1  8/2008  Chissoe

FOREIGN PATENT DOCUMENTS

| WO | WO-2007044860 A2 | 4/2007 |
| WO | WO-2008131224 A2 | 10/2008 |
| WO | WO-2009014639 A2 | 1/2009 |

OTHER PUBLICATIONS

Tascilar et al. (Annals of Oncology 10,Suppl. 4:S107-S110, 1999).*
Tockman et al. (Cancer Research 52:2711s-2718s, 1992).*
Duvillared et al. (care.diabetesjournals.org/content/26/5/1540 pp. 1-11, 2003).*
Pihlajamaki et al., "Thyroid hormone-related regulation of gene expression in human fatty liver", J Clin Endocrinol Metab, Sep. 2009, 94(9):3521-3529.
International Search Report and Written Opinion from PCT/IB2014/000426 dated Jul. 14, 2014.
European Search Report dated Oct. 4, 2016 for EP 14746108.1.

* cited by examiner

*Primary Examiner* — Lisa V Cook
(74) *Attorney, Agent, or Firm* — McCarter & English, LLP; Jonathan M. Sparks; Deborah L. Nagle

(57) ABSTRACT

The present invention provides biomarkers, methods and kits for diagnosing and prognosing the development of impaired glucose tolerance in a subject and the progression of diabetes in a subject, as well as methods for identifying a compound that can inhibit the development of impaired glucose tolerance and/or type 2 diabetes; reduce or slow down the progression of normal glucose tolerance to impaired fasting glycaemia, to impaired glucose tolerance, and/or to diabetes; and/or reduce or inhibit the development of complications associated with the disease in a subject, and methods for inhibiting the development of impaired glucose tolerance and/or type 2 diabetes; reducing or slowing down the progression of normal glucose tolerance to impaired fasting glycaemia, to impaired glucose tolerance, and/or to diabetes; and/or reducing or inhibiting the development of complications associated with the disease in a subject.

8 Claims, 1 Drawing Sheet

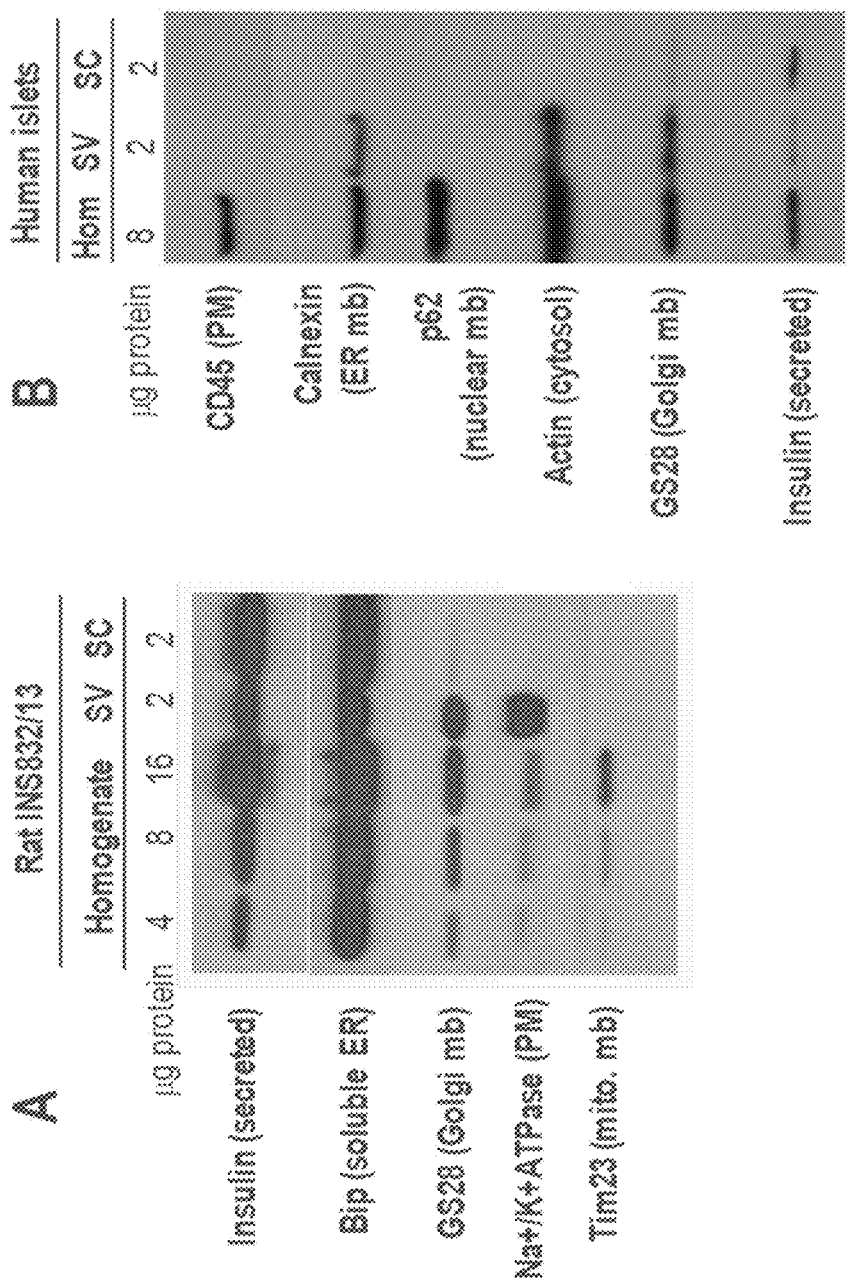

TYPE 2 DIABETES BIOMARKERS AND USES THEREOF

RELATED APPLICATIONS

This application is a 35 U.S.C. 111(a) continuation application, which claims the benefit of priority to PCT/PCT/IB2014/000426, filed on Jan. 31, 2014 and U.S. Provisional Patent Application Ser. No. 61/758,987, filed on Jan. 31, 2013, the entire contents of each of which is incorporated herein by reference.

BACKGROUND OF THE INVENTION

Diabetes mellitus type 2 (also referred to as noninsulin-dependent diabetes mellitus (NIDDM) or adult-onset diabetes) is a metabolic disorder that is characterized by high blood glucose in the presence of insulin resistance and relative insulin deficiency. Type 2 diabetes is a progressive disease in which the risks of myocardial infarction, stroke, microvascular events and mortality are all strongly associated with hyperglycaemia. Type 2 diabetes is also a silent disease with significant declines in β-cell function and kidney damage often occurring before any symptoms of the disease manifest.

The progression from normal glucose tolerance (NGT) to type 2 diabetes involves intermediate stages of impaired fasting glucose (IFG) and impaired glucose tolerance (IGT), also known as prediabetes. The pathophysiology underlying the development of these glucose metabolic alterations is multifactorial and includes, for example, lifestyle and genetic factors. In particular, obesity is thought to be the primary cause of type 2 diabetes in people who are genetically predisposed to the disease and rates of type 2 diabetes have increased markedly over the last 50 years in parallel with obesity. As of 2010 there are approximately 285 million people with the disease compared to around 30 million in 1985.

Although numerous risk factors, such as age, body mass index (BMI), and ethnicity, have been associated with the development of prediabetes and type 2 diabetes, these are not adequate to accurately predict the risk of progression from normal glucose tolerance to impaired glucose tolerance and/or from impaired glucose tolerance to type 2 diabetes since the development and progression of diabetes is often silent with organ damage occurring before the onset of identifiable symptoms. In addition, although methods for determining whether a subject has impaired glucose tolerance and/or type 2 diabetes are known (e.g., glucose tolerance testing), such methods require overnight fasting and multiple blood draws over several hours and are often associated with side effects, such as, nausea, vomiting, abdominal bloating, and/or headache.

Accordingly, as early identification of subjects who have impaired glucose tolerance and/or type 2 diabetes and/or who are at risk of developing impaired glucose tolerance and/or type 2 diabetes and/or those that will respond to a particular therapy would decrease short-term and long-term complications associated with glucose imbalance, there is a need in the art for reliable and accurate methods of determining which subjects have or will develop impaired glucose tolerance and/or type 2 diabetes and/or respond to a therapy to permit early intervention.

SUMMARY OF THE INVENTION

The present invention is based, at least in part, on the discovery of markers that are associated with the development of impaired glucose tolerance and/or type 2 diabetes and the response of subjects having impaired glucose tolerance and/or type 2 diabetes to a treatment. Accordingly, the present invention provides sensitive and facile methods and kits for predicting whether a subject has or will develop impaired glucose tolerance, methods and kits for predicting whether a subject has or will develop diabetes, as well as methods for identifying a compound that can slow down the progression of impaired glucose tolerance and/or type 2 diabetes, methods of monitoring the effectiveness of a therapy in reducing the progression of impaired glucose tolerance and/or type 2 diabetes in a subject, and methods for inhibiting progression of impaired glucose tolerance and/or type 2 in a cell or a subject by measuring and identifying particular markers, or particular combinations of markers.

Accordingly, in one aspect the present invention provides methods for determining whether a subject has or will develop impaired glucose tolerance. The methods include determining the level of one or more markers of the invention, e.g., any one or more of the markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, in a sample(s) from the subject; comparing the level of the one or more markers in the subject sample(s) with a level of the one or more markers in a control sample(s), wherein a difference in the level of the one or more markers in the subject sample(s) as compared to the level of the one or more markers in the control sample(s) indicates that the subject has or will develop impaired glucose tolerance.

In another aspect, the present invention provides methods for determining whether a subject has or will develop type 2 diabetes. The methods include determining the level of one or more markers of the invention, e.g., any one or more of the markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, in a sample(s) from the subject; comparing the level of the one or more markers in the subject sample(s) with a level of the one or more markers in a control sample(s), wherein a difference in the level of the one or more markers in the subject sample(s) as compared to the level of the one or more markers in the control sample(s) indicates that the subject has or will develop type 2 diabetes.

In another aspect, the present invention provides methods for determining whether a subject will develop a type 2 diabetes-associated complication. The methods include determining the level of one or more markers of the invention, e.g., any one or more of the markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, in a sample(s) from the subject; comparing the level of the one or more markers in the subject sample(s) with a level of the one or more markers in a control sample(s), wherein a difference in the level of the one or more markers in the subject sample(s) as compared to the level of the one or more markers in the control sample(s) indicates that the subject will develop a type 2 diabetes-associate complication.

In yet another aspect, the present invention provides methods for determining whether a subject having impaired glucose tolerance and/or type 2 diabetes will respond to a therapy. The methods include determining the level of one or more markers of the invention, e.g., any one or more of the markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, in a sample(s) from the subject; comparing the level of the one or more markers in the subject sample(s) with a level of the one or more markers in a control sample(s), wherein a difference in the level of the one or more markers in the subject sample(s) as compared to the level of the one or more markers in the control sample(s) indicates that the subject will respond to the therapy.

In another aspect, the present invention provides methods for monitoring the effectiveness of a treatment in a subject having impaired glucose tolerance and/or type 2 diabetes. The methods include determining the level of one or more markers of the invention, e.g., any one or more of the markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, in a first sample(s) from the subject prior to the initiation of the treatment; determining the level of one or more markers in a second sample(s) from the subject after at least a portion of the treatment has been administered; comparing the level of the one or more markers in the first sample(s) with a level of the one or more markers in the second sample(s), wherein a difference in the level of the one or more markers in the first sample(s) as compared to the level of the one or more markers in the second sample(s) indicates that the subject will respond to the treatment.

In one aspect, the present invention provides methods for identifying a compound that can inhibit the development of impaired glucose tolerance and/or type 2 diabetes, the method comprising contacting an aliquot of a sample(s) from the subject with each member of a library of compounds; determining the effect of a member of the library of compounds on the level and/or activity of one or more markers of the invention, e.g., any one or more of the markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, in each of the aliquots; and selecting a member of the library of compounds which modulates the level and/or the activity of the one or more marker(s) of the invention in an aliquot as compared to the level and/or activity of the one or more marker(s) of the invention in a control sample, thereby identifying a compound that can inhibit the development of impaired glucose tolerance and/or type 2 diabetes.

In another aspect, the present invention provides methods for inhibiting the development of impaired glucose tolerance and/or type 2 diabetes in a subject. The methods include administering to the subject an effective amount of an agent that modulates the expression and/or activity of any one or more of the markers of the invention, e.g., any one or more of the markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, thereby inhibiting the development of impaired glucose tolerance and/or type 2 diabetes in the subject.

In one embodiment the level in the subject sample(s) is determined by mass spectrometry. In one embodiment the mass spectrometry is matrix assisted laser desorption/time of flight (MALDI/TOF) mass spectrometry, liquid chromatography quadruple ion trap electrospray (LCQ-MS), or surface enhanced laser desorption ionization/time of flight (SELDI/TOF) mass spectrometry.

In another embodiment the level in the subject sample(s) is determined by immunoassay.

The sample(s) from the subject may be a fluid sample(s) or a tissue sample(s).

In one embodiment, the level of the marker is an expression level and/or activity of the marker.

In one embodiment the subject is at risk of developing type 2 diabetes.

In one aspect, the present invention provides kits for determining whether a subject has or will develop impaired glucose tolerance. The kits include reagents for determining the level of one or more markers, e.g., one or more markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, in a subject sample(s) and instructions for use of the kit to determine whether the subject has or will develop impaired glucose tolerance.

In another aspect, the present invention provides kits for determining whether a subject has or will develop type 2 diabetes. The list include reagents for determining the level of one or more markers, e.g., one or more markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, in a subject sample(s) and instructions for use of the kit to determine whether the subject has or will develop type 2 diabetes.

In yet another aspect, the present provides kits for determining whether a subject has or will develop type 2 diabetes complications. The kits include reagents for determining the level of one or more markers, e.g., one or more markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, in a subject sample(s) and instructions for use of the kit to determine whether the subject has or will develop type 2 diabetes complications.

In another aspect, the present invention provides kits for determining whether a subject having impaired glucose tolerance and/or type 2 diabetes will respond to a treatment. The kits include reagents for determining the level of one or more markers, e.g., one or more markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, in a subject sample(s) and instructions for use of the kit to determine whether the subject will respond to the treatment.

In yet another aspect, the present invention provides kits of monitoring the effectiveness of a treatment in a subject having impaired glucose tolerance and/or type 2 diabetes. The uts include reagents for determining the level of one or more markers, e.g., one or more markers listed in any of Tables 1-3; USP9X; SEPT3; INS and SERPINB13; PPY and DAG1; INS, CPM, and MMP7; BTC, MMP7, and PPY; PPY, SEPT3, and PTPRJ; CPM, INS, MMP7, and LDLR, in a subject sample(s) and instructions for use of the kit to monitor the effectiveness of the treatment.

In one embodiment, the kits further comprise reagents for obtaining a sample from a subject.

In one embodiment, the kits further comprise a control sample.

In one aspect, the present invention provides methods for identifying a type 2 diabetes marker. The methods include identifying proteins in the secretory vesicles of two or more organs from two or more species under steady state conditions; identifying proteins in the secretory vesicles of pancreatic β cells thereby generating a provisional list of steady state markers; identifying the markers in the provisional list of steady state markers from the two or more organs from the two or more species common to the markers in the secretory vesicles of pancreatic β cells and removing those markers from the provisional list of steady state markers, thereby generating a list of β cell mass markers; identifying proteins in the secretory vesicles of pancreatic β cells under dysfunctional conditions, identifying proteins in the secretory vesicles of pancreatic β cells under normal conditions, identifying the proteins that were differentially expressed under dysfunctional conditions and under normal conditions, thereby generating a provisional list of β cell function markers, determining the level of a β cell mass marker and/or a β cell function marker in a sample(s) form a test sample and a control sample, wherein a difference in the level of a marker in the control sample as compared to the level in the test sample identifies the marker as a type 2 diabetes biomarker.

In one embodiment, the test sample is from a subject having impaired glucose tolerance. In another embodiment, the test sample is from a subject having newly diagnosed type 2 diabetes. In yet another embodiment, the test sample is from a subject having established type 2 diabetes.

In one embodiment, the control sample is from a subject having normal glucose tolerance. In another embodiment, the control sample is from a subject having impaired glucose tolerance. In yet another embodiment, the control sample is from a subject having newly diagnosed type 2 diabetes.

In another aspect, the present invention provides methods for identifying a type 2 diabetes marker. The methods include identifying proteins differentially expressed in a sample(s) from a subject before and after treatment, thereby generating a list of therapeutic efficacy markers; determining the level of one or more of the markers in a first sample obtained from a subject having type 2 diabetes prior to providing at least a portion of a therapy to the subject; and determining the level of a protein in a second sample obtained from the subject following provision of at least a portion of the therapy, wherein a difference in the level of expression of the one or more markers in the second sample relative to the first sample identifies the protein as a type 2 diabetes marker.

BRIEF DESCRIPTION OF THE DRAWINGS

FIG. 1 depicts Western blots of proteins identified during the process of secreted proteins preparation. Cell or tissue homogenates were prepared by mechanical disruption and secretory pathway vesicles isolated by sucrose density centrifugation. The resultant vesicles were washed with salt to remove loosely attached proteins, opened with alkali, and the secretory protein contents retrieved by high speed centrifugation. Shown are western blots of starting materials (Hom), intermediate (SV) and final product (SC) preparations from a rat cell line (A) and human primary islets (B). The western blot markers were against specific intracellular compartments and indicate the progressive enrichment of secretory proteins during sample preparation. Hom: homogenate; SV: secretory vesicle; SC: secretory vesicle contents; Mb: membrane; PM: plasma membrane.

DETAILED DESCRIPTION OF THE INVENTION

The present invention is based, at least in part, on the discovery of markers that are associated with the development of impaired glucose tolerance and/or type 2 diabetes, the progression of type 2 diabetes, and the response of a subject having impaired glucose tolerance and/or type 2 diabetes to a treatment. In particular, biomarkers associated with type 2 diabetes have been discovered, prioritized, and validated in multiple in vitro experimental systems. The markers were identified as being expressed, e.g., essentially specifically expressed in β-cells, and/or as being involved, e.g., essentially specifically involved, in β-cell function, and/or as being involved in response to a therapeutic treatment.

Accordingly, the present invention provides sensitive and facile methods and kits for predicting whether a subject has or will develop impaired glucose tolerance, methods and kits for predicting whether a subject has or will develop diabetes, as well as methods for identifying a compound that can slow down the progression of impaired glucose tolerance and/or type 2 diabetes, methods of monitoring the effectiveness of a therapy in reducing the progression of impaired glucose tolerance and/or type 2 diabetes in a subject, and methods for inhibiting progression of impaired glucose tolerance and/or type 2 in a cell or a subject by measuring and identifying particular markers, or particular combinations of markers.

Various aspects of the invention are described in further detail in the following subsections:

I. Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "marker" or "biomarker" is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median level, e.g., expression level, of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for, e.g., disease (prognostics and diagnostics), therapeutic effectiveness of a drug (theranostics) and of drug toxicity.

In some embodiments, the accuracy of a marker(s) useful in the compositions and methods of the present invention may be characterized by a Receiver Operating Characteristic curve ("ROC curve"). An ROC is a plot of the true positive rate against the false positive rate for the different possible cutpoints of a diagnostic marker(s). An ROC curve shows the relationship between sensitivity and specificity. That is, an increase in sensitivity will be accompanied by a decrease in specificity. The closer the curve follows the left axis and then the top edge of the ROC space, the more accurate the marker(s). Conversely, the closer the curve comes to the 45-degree diagonal of the ROC graph, the less accurate the marker(s). The area under the ROC is a measure of a marker(s) accuracy. The accuracy of the marker(s) depends on how well the marker(s) separates the group being tested into those with and without the disease in question. An area under the curve (referred to as "AUC") of 1 represents a perfect marker(s), while an area of 0.5 represents a less useful marker(s). Thus, in some embodiments, biomarkers and methods of the present invention have an AUC greater than about 0.50, an AUC greater than about 0.60, or an AUC greater than about 0.70.

"Type 2 diabetes" also referred to herein as "diabetes" is characterized by a combination of peripheral insulin resistance and inadequate insulin secretion by pancreatic beta cells. A "subject has diabetes" if the subject has a fasting plasma glucose (FPG) level of about 126 mg/dL (about 7.0 mmol/L) or higher; a 2-hour plasma glucose (PG) level of about 200 mg/dL (about 11.1 mmol/L) or higher during a 75-g oral glucose tolerance test (OGTT); a random plasma glucose of about 200 mg/dL (about 11.1 mmol/L) or higher in a subject having symptoms of hyperglycemia or hyperglycemic crisis; and/or a hemoglobin A1c (HbA1c) level of about 6.5% or higher.

A subject having "normal glucose tolerance" or "NGT" has a 2-hour plasma glucose (PG) level of less than about 140 mg/dL (less than about 7.8 mmol/L) during a 75-g oral glucose tolerance test (OGTT); a fasting plasma glucose (FPG) level of less than about 110 mg/dL (less than about 6.1 mmol/L); and/or a hemoglobin A1c (HbA1c) level of less than about 6%.

A "subject at risk of developing diabetes" is a subject that has a sustained blood pressure about 135/80 mm Hg or higher; is overweight (e.g., has a body mass index (BMI) greater than about 30 kg/m$^2$); has a first-degree relative with diabetes; has an HDL level about 35 mg/dL or higher and/or triglyceride level less than about 250 mg/dL); is age 45 years or older; is female; has a history of gestational diabetes; has polycystic ovarian syndrome; has a condition associated with metabolic syndrome; is Hispanic; is African-American; and/or is Native-American. In addition, a number of medications and other diseases can put a subject at risk of developing diabetes. For example, glucocorticoids, thiazides, beta blockers, atypical antipsychotics, and statins may put a subject at risk of developing diabetes. Subjects who have previously had acromegaly, Cushing's syndrome, hyperthyroidism, pheochromocytoma, and certain cancers such as glucagonomas, and testosterone deficiency are also at risk of developing type 2 diabetes.

A subject, e.g., a subject at risk of developing diabetes, may be "pre-diabetic." A subject is considered "pre-diabetic" if the subject has an impaired glucose tolerance. "Impaired glucose tolerance" is a state of hyperglycemia that is associated with insulin resistance and increased risk of cardiovascular pathology. A subject has impaired glucose tolerance when the subject has an intermediately raised glucose level after 2 hours, but less than would qualify for type 2 diabetes mellitus. The fasting glucose may be either normal or mildly elevated.

A subject having impaired glucose tolerance has a 2-hour plasma glucose (PG) level of about 140 mg/dL (about 7.8 mmol/L) or higher during a 75-g oral glucose tolerance test (OGTT) (e.g., between about 7.8 and 11 mmol/L); a fasting plasma glucose (FPG) level of less than about 126 mg/dL (less than about 7 mmol/L) (e.g., between about 95 and about 125 mg/dL); a hemoglobin A1c (HbA1c) level of about 6% or higher (e.g., between about 6.0 and 6.4); and/or a BMI about 24 kg/m$^2$ or greater.

A subject, e.g., a subject at risk of developing diabetes, may have "impaired fasting glycaemia." A subject having impaired fasting glycaemia has a 2-hour plasma glucose (PG) level of less than about 140 mg/dL (less than about 7.8 mmol/L) during a 75-g oral glucose tolerance test (OGTT); a fasting plasma glucose (FPG) level of less than about 126 mg/dL (less than about 7 mmol/L) (e.g., between about 110 and about 125 mg/dL); and/or a hemoglobin A1c (HbA1c) level of about 6% or higher (e.g., between about 6.0 and 6.4).

The term "diabetes has progressed" refers to the progression of normal glucose tolerance to impaired fasting glycaemia; the progression of normal glucose tolerance to impaired glucose tolerance; the progression of normal glucose tolerance to type 2 diabetes; the progression of impaired fasting glycaemia to impaired glucose tolerance; the progression of impaired fasting glycaemia to type 2 diabetes; and/or the progression of impaired glucose tolerance to type 2 diabetes in a subject.

A "level of a marker" or "the level of a biomarker" refers to an amount of a marker present in a sample being tested. A level of a marker may be either in absolute level or amount (e.g., µg/ml) or a relative level or amount (e.g., relative intensity of signals). A "higher level" or an "increase in the level" of marker refers to a level of a marker in a test sample that is greater than the standard error of the assay employed to assess the level of the marker, and is preferably at least twice, and more preferably three, four, five, six, seven, eight, nine, or ten or more times the level of marker in a control sample (e.g., a sample from a subject having normal glucose tolerance, a subject having impaired fasting glycaemia, a subject having impaired glucose tolerance, a subject having been diagnosed with type 2 diabetes in the previous 18 months, and/or, the average level of the marker in several control samples).

A "lower level" or a "decrease in the level" of a marker refers to a level of the marker in a test sample that is less than the standard error of the assay employed to assess the level of the marker, and preferably at least twice, and more preferably three, four, five, six, seven, eight, nine, or ten or more times less than the level of the marker in a control sample (e.g., a sample from a subject having normal glucose tolerance, a subject having impaired fasting glycaemia, a subject having impaired glucose tolerance, a subject having been diagnosed with type 2 diabetes in the previous 18 months, and/or, the average level of the marker in several control samples).

The term "known standard level" or "control level" refers to an accepted or pre-determined level of a marker which is used to compare the level of the marker in a sample derived from a subject. In one embodiment, the control level of a marker is based the level of the marker in a sample(s) from a subject(s) having normal glucose tolerance. In another embodiment, the control level of a marker is based on the level of the marker in a sample from a subject or subjects having impaired fasting glycaemia. In another embodiment, the control level of a marker is based on the level of the marker in a sample(s) from a subject having impaired glucose tolerance. In another embodiment, the control level of a marker is based on the level of the marker in a sample(s) from a subject having been diagnosed with type 2 diabetes with the previous 18 months. In one embodiment, the control level of a marker in a sample from a subject is a level of the marker previously determined in a sample(s) from the subject.

In yet another embodiment, the control level of a marker is based on the level of the marker in a sample from a subject(s) prior to the administration of a therapy for impaired fasting glycaemia, impaired glucose tolerance, and/or type 2 diabetes. In another embodiment, the control level of a marker is based on the level of the marker in a sample(s) from a subject(s) having impaired fasting glycaemia, impaired glucose tolerance, and/or type 2 diabetes that is not contacted with a test compound. In another embodiment, the control level of a marker is based on the level of the marker in a sample(s) from a subject(s) having normal glucose tolerance that is contacted with a test compound. In one embodiment, the control level of a marker is based on the expression level of the marker in a sample(s) from an animal model of impaired fasting glycaemia, impaired glucose tolerance, and/or type 2 diabetes, a cell, or a cell line derived from the animal model of impaired fasting glycaemia, impaired glucose tolerance, and/or type 2 diabetes.

Alternatively, and particularly as further information becomes available as a result of routine performance of the methods described herein, population-average values for "control" level of expression of a marker may be used. In other embodiments, the "control" level of a marker may be determined by determining the level of a marker in a subject sample obtained from a subject before the suspected onset of impaired fasting glycaemia, impaired glucose tolerance, and/or type 2 diabetes in the subject, from archived subject samples, and the like.

As used herein, the terms "patient" or "subject" refer to human and non-human animals, e.g., veterinary patients. The term "non-human animal" includes all vertebrates, e.g., mammals and non-mammals, such as non-human primates, mice, rabbits, sheep, dog, cat, horse, cow, chickens, amphibians, and reptiles. In one embodiment, the subject is a human.

In some embodiments, a subject has a body mass index (BMI) of less than about 40 kg/m$^2$ (e.g., about 40 39, 38, 37, 36, 35, 34, 33, 32, 31, 30, 29, 28, 27, 26, 25, 24, 23, 22, 21, 20, 19, or about 18 kg/m$^2$). In other embodiments, a subject has a body mass index (BMI) of greater than about 40 kg/m$^2$ (e.g., about 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or about 80 kg/m$^2$).

The term "sample" as used herein refers to a collection of similar cells or tissue isolated from a subject, as well as tissues, cells and fluids present within a subject. The term "sample" includes any body fluid (e.g., blood fluids, lymph, gynecological fluids, cystic fluid, urine, ocular fluids and fluids collected by bronchial lavage and/or peritoneal rinsing), or a cell from a subject. In one embodiment, the tissue or cell is removed from the subject. In another embodiment, the tissue or cell is present within the subject. Other subject samples, include tear drops, serum, cerebrospinal fluid, feces, sputum and cell extracts. In one embodiment, the biological sample contains protein molecules from the test subject. In another embodiment, the biological sample may contain mRNA molecules from the test subject or genomic DNA molecules from the test subject.

The term "determining" means methods which include detecting the presence or absence of marker(s) in the sample, quantifying the amount of marker(s) in the sample, and/or qualifying the type of biomarker. Measuring can be accomplished by methods known in the art and those further described herein.

As used herein, the various forms of the term "modulate" are intended to include stimulation (e.g., increasing or upregulating a particular response or activity) and inhibition (e.g., decreasing or downregulating a particular response or activity).

A kit is any manufacture (e.g. a package or container) comprising at least one reagent, e.g. a probe, a primer, or an antibody, for specifically detecting a marker of the invention, the manufacture being promoted, distributed, or sold as a unit for performing the methods of the present invention. In certain embodiments, a lit may include a substrate, e.g., a substrate comprising a capture reagent for one or more markers of the invention and/or a capture reagent bound to one or more markers of the invention. In some embodiments, such kits comprise instructions for determining the level of a marker(s) using mass spectrometry.

II. Markers of the Invention

The present invention is based upon the discovery of markers that are essentially specifically expressed in pancreatic β-cells (Table 1), and/or as being essentially specifically involved in β-cell function (Table 2), and/or as being involved in response to a therapeutic treatment (Table 3). These markers have been shown to be differentially present in samples of subjects having impaired glucose tolerance and control subjects, and/or differentially present in samples of subjects having impaired glucose tolerance and subjects having newly diagnosed type 2 diabetes, and/or differentially present in samples of subjects having impaired glucose tolerance and subjects having established type 2 diabetes, and/or differentially present in samples of subjects having newly diagnosed type 2 diabetes and subjects having established type 2 diabetes, and/or differentially expressed in samples of subjects responsive to treatment with an insulin sensitizer and subjects non-responsive to an insulin sensitizer, and/or differentially expressed in samples of subjects responsive to treatment with an insulin sensitizer and a secretagogue and subjects non-responsive to an insulin sensitizer and a secretagogue, and/or differentially expressed in samples of subjects responsive to treatment with an insulin sensitizer, a secretagogue, and insulin and subjects non-responsive to an insulin sensitizer, a secretagogue, and insulin.

Accordingly, the level of any one marker or any combination of markers listed in Tables 1-3 found in a test sample compared to a control, or the presence or absence of one marker or combination of markers listed in Tables 1-3 in the test sample may be used in the methods and kits of the present invention.

The markers of the invention are listed in Tables 1-3. The nucleotide and amino acid sequences of the markers are known in the art and may be found in, for example, the GenBank Accession numbers listed in Tables 1-3, the entire contents of which are incorporated herein by reference.

TABLE 1

β-Cell Mass Markers of the Invention.

| Marker Name | Protein Description | UNIPROT_ID | UNIPROT ACCESSION | GENBANK ACCESSION |
|---|---|---|---|---|
| ABCC8 | ATP-binding cassette sub-family C member 8 | ABCC8_HUMAN | Q09428 | NP_000343.2. NM_000352.3. |

TABLE 1-continued

β-Cell Mass Markers of the Invention.

| Marker Name | Protein Description | UNIPROT_ID | UNIPROT ACCESSION | GENBANK ACCESSION |
|---|---|---|---|---|
| ACPP | Prostatic acid phosphatase | PPAP_HUMAN | P15309 | NP_001090.2<br>NM_001099.4<br>NP_001127666.1<br>NM_001134194.1 |
| APLP1 | Amyloid-like protein 1 | APLP1_HUMAN | P51693 | NP_001019978.1.<br>NM_001024807.1.<br>NP_005157.1.<br>NM_005166.3. |
| APOL2 | Apolipoprotein L2 | APOL2_HUMAN | Q9BQE5 | NP_112092.1<br>NM_030882.2<br>NP_663612.1<br>NM_145637.1 |
| APP | Amyloid beta A4 protein | A4_HUMAN | P05067 | NP_000475.1<br>NM_000484.3<br>NP_001129488.1.<br>NM_001136016.3<br>NP_001129601.1.<br>NM_001136129.2<br>NP_001129602.1.<br>NM_001136130.2<br>NP_001129603.1.<br>NM_001136131.2<br>NP_001191230.1.<br>NM_001204301.1.<br>NP_001191231.1.<br>NM_001204302.1.<br>NP_001191232.1.<br>NM_001204303.1.<br>NP_958816.1.<br>NM_201413.2.<br>NP_958817.1.<br>NM_201414.2. |
| ATP8A1 | Probable phospholipid-transporting ATPase IA | AT8A1_HUMAN | Q9Y2Q0 | NP_001098999.1.<br>NM_001105529.1.<br>NP_006086.1.<br>NM_006095.2. |
| ATP9A | Probable phospholipid-transporting ATPase IIA | ATP9A_HUMAN | O75110 | NP_006036.1.<br>NM_006045.1. |
| BET1L | BET1-like protein | BET1L_HUMAN | Q9NYM9 | NP_001092257.1.<br>NM_001098787.1. |
| BMP7 | Bone morphogenetic protein 7 | BMP7_HUMAN | P18075 | NP_001710.1.<br>NM_001719.2. |
| BOLA1 | BolA-like protein 1 | BOLA1_HUMAN | Q9Y3E2 | NP_057158.1.<br>NM_016074.3. |
| BTC | Probetacellulin | BTC_HUMAN | P35070 | NP_001720.1.<br>NM_001729.2. |
| C12ORF23 | UPF0444 transmembrane protein C12orf23 | CL023_HUMAN | Q8WUH6 | NP_689474.1.<br>NM_152261.2. |
| C6ORF142 | Muscular LMNA-interacting protein | MLIP_HUMAN | Q5VWP3 | NP_612636.2.<br>NM_138569.2. |
| C9ORF5 | Transmembrane protein 245 | TM245_HUMAN | Q9H330 | NP_114401.2.<br>NM_032012.3. |
| CADM1 | Cell adhesion molecule 1 | CADM1_HUMAN | Q9BY67 | NP_001091987.1.<br>NM_001098517.1.<br>NP_055148.3.<br>NM_014333.3. |
| CASC4 | Protein CASC4 | CASC4_HUMAN | Q6P4E1 | NP_612432.2.<br>NM_138423.3.<br>NP_816929.1.<br>NM_177974.2. |
| CASR | Peripheral plasma membrane protein CASK | CASR_HUMAN | P41180 | NP_000379.2<br>NM_000388.3<br>NP_001171536.1<br>NM_001178065.1 |
| CBARA1 | Calcium uptake protein 1, mitochondrial | MICU1_HUMAN | Q9BPX6 | NP_001182447.1.<br>NM_001195518.1.<br>NP_001182448.1.<br>NM_001195519.1.<br>NP_006068.2.<br>NM_006077.3. |
| CCDC115 | Coiled-coil domain- | CC115_HUMAN | Q96NT0 | NP_115733.2. |

TABLE 1-continued

β-Cell Mass Markers of the Invention.

| Marker Name | Protein Description | UNIPROT_ID | UNIPROT ACCESSION | GENBANK ACCESSION |
|---|---|---|---|---|
| | containing protein 115 | | | NM_032357.2. |
| CD47 | Leukocyte surface antigen CD47 | CD47_HUMAN | Q08722 | NP_001768.1. NM_001777.3. NP_942088.1. NM_198793.2. |
| CD59 | CD59 glycoprotein | CD59_HUMAN | P13987 | NP_000602.1 NM_000611.5 NP_001120695.1 NM_001127223.1 NP_001120697.1 NM_001127225.1 NP_001120698.1 NM_001127226.1 NP_001120699.1 NM_001127227.1 NP_976074.1 NM_203329.2 NP_976075.1 NM_203330.2 NP_976076.1 NM_203331.2 |
| CDCP1 | CUB domain-containing protein 1 | CDCP1_HUMAN | Q9H5V8 | NP_073753.3. NM_022842.3. NP_835488.1. NM_178181.1. |
| CFDP1 | Craniofacial development protein 1 | CFDP1_HUMAN | Q9UEE9 | NP_006315.1. NM_006324.2. |
| CHGB | Secretogranin-1 | SCG1_HUMAN | P05060 | NP_001810.2. NM_001819.2. |
| CHKA | Choline kinase alpha | CHKA_HUMAN | P35790 | NP_001268.2. NM_001277.2. NP_997634.1. NM_212469.1. |
| CLLD6 | SPRY domain-containing protein 7 | SPRY7_HUMAN | Q5W111 | NP_001120954.1. NM_001127482.1. NP_065189.1. NM_020456.2. |
| CNNM2 | Metal transporter CNNM2 | CNNM2_HUMAN | Q9H8M5 | NP_060119.3. NM_017649.4. NP_951058.1. NM_199076.2. NP_951059.1. NM_199077.2. |
| CNP | 2',3'-cyclic-nucleotide 3'-phosphodiesterase | CN37_HUMAN | P09543 | NP_149124.3. NM_033133.4. |
| CNPY4 | Protein canopy homolog 4 | CNPY4_HUMAN | Q8N129 | NP_689968.1. NM_152755.1. |
| CNTN1 | Contactin-1 | CNTN1_HUMAN | Q12860 | NP_001242992.1 NM_001256063.1 NP_001242993.1 NM_001256064.1 NP_001834.2 NM_001843.3 NP_778203.1 NM_175038.2 |
| COMMD10 | COMM domain-containing protein 10 | COMDA_HUMAN | Q9Y6G5 | NP_057228.1. NM_016144.2. |
| CPE | Carboxypeptidase E | CBPE_HUMAN | P16870 | NP_001864.1 NM_001873.2 |
| CSHL1 | Chorionic somatomammotropin hormone-like 1 | CSHL_HUMAN | Q14406 | NP_072101.1. NM_022579.1. NP_072102.1. NM_022580.1. NP_072103.1. NM_022581.1. |
| CSTF3 | Cleavage stimulation factor subunit 3 | CSTF3_HUMAN | Q12996 | NP_001028677.1 NM_001033505.1 NP_001028678.1 NM_001033506.1 NP_001317.1 NM_001326.2 |

TABLE 1-continued

β-Cell Mass Markers of the Invention.

| Marker Name | Protein Description | UNIPROT_ID | UNIPROT ACCESSION | GENBANK ACCESSION |
|---|---|---|---|---|
| CYFIP1 | Cytoplasmic FMR1-interacting protein 1 | CYFP1_HUMAN | Q7L576 | NP_001028200.1. NM_001033028.1. NP_055423.1. NM_014608.2. |
| CYFIP2 | Cytoplasmic FMR1-interacting protein 2 | CYFP2_HUMAN | Q96F07 | NP_001032409.2. NM_001037332.2. NP_001032410.1. NM_001037333.1. NP_055191.2. NM_014376.2. |
| CYTL1 | Cytokine-like protein 1 | CYTL1_HUMAN | Q9NRR1 | NP_061129.1. NM_018659.2. |
| CYTSA | Cytospin-A | CYTSA_HUMAN | Q69YQ0 | NP_056145.3. NM_015330.3. |
| DAG1 | similar to Dystroglycan precursor | DAG1_HUMAN | Q14118 | NP_001159400.2-NM_001165928.3 NP_001171105.1 NM_001177634.2 NP_001171106.1 NM_001177635.2 NP_001171107.1 NM_001177636.2 NP_001171108.1 NM_001177637.2 NP_001171109.1 NM_001177638.2 NP_001171110.1 NM_001177639.2 NP_001171111.1 NM_001177640.2 NP_001171112.1 NM_001177641.2 NP_001171113.1 NM_001177642.2 NP_001171114.1 NM_001177643.2 NP_001171115.1 NM_001177644.2 NP_004384.4 NM_004393.5 |
| DKK2 | Dickkopf-related protein 2 | DKK2_HUMAN | Q9UBU2 | NP_055236.1. NM_014421.2. |
| DSCAML1 | Down syndrome cell adhesion molecule-like protein 1 | DSCL1_HUMAN | Q8TD84 | NP_065744.2. NM_020693.2. |
| EDIL3 | EGF-like repeat and discoidin 1-like domain-containing protein 3 | EDIL3_HUMAN | O43854 | NP_005702.3. NM_005711.3. |
| EMB | Embigin | EMB_HUMAN | Q6PCB8 | NP_940851.1. NM_198449.2. |
| ENPP1 | Ectonucleotide pyrophosphatase/phosphodiesterase family member 1 | ENPP1_HUMAN | P22413 | NP_006199.2. NM_006208.2. |
| ENPP4 | Ectonucleotide pyrophosphatase/phosphodiesterase family member 4 | ENPP4_HUMAN | Q9Y6X5 | NP_055751.1. NM_014936.4. |
| ENTPD3 | Ectonucleoside triphosphate diphosphohydrolase 3 | ENTP3_HUMAN | O75355 | NP_001239.2. NM_001248.2. |
| EPN2 | Epsin-2 | EPN2_HUMAN | O95208 | NP_055779.2. NM_014964.4. |
| ERO1LB | ERO1-like protein beta | ERO1B_HUMAN | Q86YB8 | NP_063944.3. NM_019891.3. |
| ESYT2 | Extended synaptotagmin-2 | ESYT2_HUMAN | A0FGR8 | NP_065779.1. NM_020728.2. |
| EXT1 | Exostosin-1 | EXT1_HUMAN | Q16394 | NP_000118.2. NM_000127.2. |
| FAM125A | Multivesicular body subunit 12A | F125A_HUMAN | Q96EY5 | NP_612410.1. NM_138401.2. |
| FAM126A | Hyccin | HYCC1_HUMAN | Q9BYI3 | NP_115970.2. NM_032581.3. |

TABLE 1-continued

β-Cell Mass Markers of the Invention.

| Marker Name | Protein Description | UNIPROT_ID | UNIPROT ACCESSION | GENBANK ACCESSION |
|---|---|---|---|---|
| FAM19A4 | Protein FAM19A4 | F19A4_HUMAN | Q96LR4 | NP_001005527.1. NM_001005527.2. NP_872328.1. NM_182522.4. |
| FAM20A | Protein FAM20A | FA20A_HUMAN | Q96MK3 | NP_001230675.1. NM_001243746.1. NP_060035.2. NM_017565.3. |
| FAM20B | Glycosaminoglycan xylosylkinase | XYLK_HUMAN | O75063 | NP_055679.1. NM_014864.3. |
| FAM20C | Family with sequence similarity 20, member C | DMP4_HUMAN | Q8IXL6 | NP_064608.2 NM_020223.3 |
| FAM3C | Protein FAM3C | FAM3C_HUMAN | Q92520 | NP_001035109.1. NM_001040020.1. NP_055703.1. NM_014888.2. |
| FAM75A6 | Spermatogenesis-associated protein 31A6 | S31A6_HUMAN | Q5VVP1 | NP_001138668.1. NM_001145196.1. |
| FAM83F | Protein FAM83F | FA83F_HUMAN | Q8NEG4 | NP_612444.2. NM_138435.2. |
| FBXL2 | F-box/LRR-repeat protein 2 | FBXL2_HUMAN | Q9UKC9 | NP_001165184.1. NM_001171713.1. NP_036289.3. NM_012157.3. |
| FGF12 | Fibroblast growth factor 12 | FGF12_HUMAN | P61328 | NP_004104.3. NM_004113.5. NP_066360.1. NM_021032.4. |
| FGF19 | Fibroblast growth factor 19 | FGF19_HUMAN | O95750 | NP_005108.1. NM_005117.2. |
| FKBP11 | Peptidyl-prolyl cis-trans isomerase FKBP11 | FKB11_HUMAN | Q9NYL4 | NP_001137253.1. NM_001143781.1. NP_001137254.1. NM_001143782.1. NP_057678.1. NM_016594.2. |
| FREM1 | FRAS1-related extracellular matrix protein 1 | FREM1_HUMAN | Q5H8C1 | NP_001171175.1. NM_001177704.1. NP_659403.4. NM_144966.5. |
| GALNT2 | Polypeptide N-acetylgalactosaminyl-transferase 2 | GALT2_HUMAN | Q10471 | NP_004472.1. NM_004481.3. |
| GAP43 | Neuromodulin | NEUM_HUMAN | P17677 | NP_001123536.1. NM_001130064.1. NP_002036.1. NM_002045.3. |
| GLRX5 | Glutaredoxin-related protein 5, mitochondrial | GLRX5_HUMAN | Q86SX6 | NP_057501.2. NM_016417.2. |
| GNPDA2 | Glucosamine-6-phosphate isomerase 2 | GNPI2_HUMAN | Q8TDQ7 | NP_001257809.1. NM_001270880.1. NP_001257810.1. NM_001270881.1. NP_612208.1. NM_138335.2. |
| GPR158 | Probable G-protein coupled receptor 158 | GP158_HUMAN | Q5T848 | NP_065803.2. NM_020752.2. |
| GPRIN1 | G protein-regulated inducer of neurite outgrowth 1 | GRIN1_HUMAN | Q7Z2K8 | NP_443131.2. NM_052899.2. |
| GREM1 | Gremlin-1 | GREM1_HUMAN | O60565 | NP_001178252.1. NM_001191323.1. NP_037504.1. NM_013372.6. |
| GREM2 | Gremlin-2 | GREM2_HUMAN | Q9H772 | NP_071914.3. M_022469.3. |
| GRK5 | G protein-coupled receptor kinase 5 | GRK5_HUMAN | P34947 | NP_005299.1. NM_005308.2. |
| GUK1 | Guanylate kinase | KGUA_HUMAN | Q16774 | NP_000849.1. NM_000858.5. |

TABLE 1-continued

β-Cell Mass Markers of the Invention.

| Marker Name | Protein Description | UNIPROT_ID | UNIPROT ACCESSION | GENBANK ACCESSION |
|---|---|---|---|---|
| | | | | NP_001152862.1. |
| | | | | NM_001159390.1. |
| | | | | NP_001152863.1. |
| | | | | NM_001159391.1. |
| | | | | NP_001229768.1. |
| | | | | NM_001242839.1. |
| HERC4 | Probable E3 ubiquitin-protein ligase HERC4 | HERC4_HUMAN | Q5GLZ8 | NP_056416.2. NM_015601.3. |
| HPCA | Neuron-specific calcium-binding protein hippocalcin | HPCA_HUMAN | P84074 | NP_071362.1. NM_022079.2. NP_002134.2. NM_002143.2. |
| HSP90B2P | Putative endoplasmin-like protein | ENPLL_HUMAN | Q58FF3 | AY956768 AAX38255.1. |
| HSPA13 | Heat shock 70 kDa protein 13 | HSP13_HUMAN | P48723 | NP_008879.3. NM_006948.4. |
| IDE | Insulin-degrading enzyme | IDE_HUMAN | P14735 | NP_001159418.1. NM_001165946.1. NP_004960.2. NM_004969.3. |
| IGF1 | Insulin-like growth factor I | IGF1_HUMAN | P05019 | NP_000609.1. NM_000618.3. NP_001104754.1. NM_001111284.1. NP_001104755.1. NM_001111285.1. |
| IGFBP7 | Insulin-like growth factor-binding protein 7 | IBP7_HUMAN | Q16270 | NP_001544.1. NM_001553.2. |
| INS | Insulin-1 | INS_HUMAN | P01308 | NP_000198.1 NM_000207.2 NP_001172026.1 NM_001185097.1 NP_001172027.1 NM_001185098.1 |
| IRS2 | Insulin receptor substrate 2 | IRS2_HUMAN | Q9Y4H2 | NP_003740.2. NM_003749.2. |
| ITFG3 | Protein ITFG3 | ITFG3_HUMAN | Q9H0X4 | NP_114428.1. NM_032039.2. |
| ITM2B | Integral membrane protein 2B | ITM2B_HUMAN | Q9Y287 | NP_068839.1. NM_021999.4. |
| ITPKB | Inositol-trisphosphate 3-kinase B | IP3KB_HUMAN | P27987 | NP_002212.3. NM_002221.3. |
| KIAA0564 | von Willebrand factor A domain-containing protein 8 | VWA8_HUMAN | A3KMH1 | NP_001009814.1. NM_001009814.1. NP_055873.1. NM_015058.1. |
| KIAA1324 | UPF0577 protein KIAA1324 | K1324_HUMAN | Q6UXG2 | NP_001253977.1. NM_001267048.1. NP_001253978.1. NM_001267049.1. NP_065826.2. NM_020775.4. |
| KIDINS220 | Kinase D-interacting substrate of 220 kDa | KDIS_HUMAN | Q9ULH0 | NP_065789.1. NM_020738.2. |
| LDLR | Low-density lipoprotein receptor | LDLR_HUMAN | P01130 | NP_000518.1 NM_000527.4 NP_001182728.1 NM_001195799.1 NP_001182729.1 NM_001195800.1 NP_001182732.1 NM_001195803.1 |
| LGALS8 | Galectin-8 | LEG8_HUMAN | O00214 | NP_006490.3. NM_006499.4. NP_963837.1. NM_201543.2. NP_963838.1. NM_201544.2. NP_963839.1. |

TABLE 1-continued

β-Cell Mass Markers of the Invention.

| Marker Name | Protein Description | UNIPROT_ID | UNIPROT ACCESSION | GENBANK ACCESSION |
|---|---|---|---|---|
| LRRC8E | Leucine-rich repeat-containing protein 8E | LRC8E_HUMAN | Q6NSJ5 | NM_201545.2. NP_001255213.1. NM_001268284.1. NP_001255214.1. NM_001268285.1. NP_079337.2. NM_025061.4. |
| LSAMP | Limbic system-associated membrane protein | LSAMP_HUMAN | Q13449 | NP_002329.2. NM_002338.3. |
| MAP1B | Microtubule-associated protein 1B | MAP1B_HUMAN | P46821 | NP_005900.2. NM_005909.3. |
| MBP | Myelin basic protein | MBP_HUMAN | P02686 | NP_001020252.1. NM_001025081.1. NP_001020261.1. NM_001025090.1. NP_001020263.1. NM_001025092.1. NP_001020271.1. NM_001025100.1. NP_001020272.1. NM_001025101.1. NP_002376.1. NM_002385.2. |
| MCRS1 | Microspherule protein 1 | MCRS1_HUMAN | Q96EZ8 | NP_001012300.1. NM_001012300.1. NP_006328.2. NM_006337.3. |
| MGAT1 | Alpha-1,3-mannosyl-glycoprotein 2-beta-acetylglucosaminyl transferase | MGAT1_HUMAN | P26572 | NP_001108089.1 NM_001114617.1 NP_001108090.1 NM_001114618.1 NP_001108091.1 NM_001114619.1 NP_001108092.1 NM_001114620.1 NP_002397.2 NM_002406.3 |
| MIA3 | Melanoma inhibitory activity protein 3 | MIA3_HUMAN | Q5JRA6 | NP_940953.2. NM_198551.2. |
| MLN | Promotilin | MOTI_HUMAN | P12872 | NP_001035198.1. NM_001040109.1. NP_001171627.1. NM_001184698.1. NP_002409.1. NM_002418.2. |
| MPP2 | MAGUK p55 subfamily member 2 | MPP2_HUMAN | Q14168 | NP_005365.3. NM_005374.3. |
| MTHFD2 | Bifunctional methylenetetra-hydrofolate dehydrogenase/ cyclohydrolase, mitochondrial | MTDC_HUMAN | P13995 | NP_006627.2. NM_006636.3. |
| MTUS1 | Microtubule-associated tumor suppressor 1 | MTUS1_HUMAN | Q9ULD2 | NP_001001924.1. NM_001001924.2. NP_001001925.1. NM_001001925.2. NP_001001931.1. NM_001001931.2. NP_001159865.1. NM_001166393.1. NP_065800.1. NM_020749.4. |
| MUC13 | Mucin-13 | MUC13_HUMAN | Q9H3R2 | RefSeq NP_149038.3. NM_033049.3. |
| MXRA7 | Matrix-remodeling-associated protein 7 | MXRA7_HUMAN | P84157 | NP_001008528.1. NM_001008528.1. NM_001008529.1. NP_940932.2. NM_198530.2. |
| NAAA | N- | NAAA_HUMAN | Q02083 | NP_001035861.1. |

TABLE 1-continued

β-Cell Mass Markers of the Invention.

| Marker Name | Protein Description | UNIPROT_ID | UNIPROT ACCESSION | GENBANK ACCESSION |
|---|---|---|---|---|
| | acylethanolamine-hydrolyzing acid amidase | | | NM_001042402.1. NP_055250.2. NM_014435.3. |
| NAGLU | Alpha-acetylglucosaminidase | ANAG_HUMAN | P54802 | NP_000254.2. NM_000263.3. |
| NCAM1 | Neural cell adhesion molecule 1 | NCAM1_HUMAN | P13591 | NP_000606.3. NM_000615.6. NP_001070150.1. NM_001076682.3. NP_001229537.1. NM_001242608.1. NP_851996.2. NM_181351.4. |
| NECAB2 | N-terminal EF-hand calcium-binding protein 2 | NECA2_HUMAN | Q7Z6G3 | NP_061938.2. NM_019065.2. |
| NELL1 | Protein kinase C-binding protein NELL1 | NELL1_HUMAN | Q92832 | NP_006148.2 NM_006157.3 NP_963845.1 NM_201551.1 |
| NEO1 | Neogenin | NEO1_HUMAN | Q92859 | NP_001166094.1. NM_001172623.1. NP_002490.2. NM_002499.3. |
| NFASC | Neurofascin | NFASC_HUMAN | O94856 | NP_001005388.2. NM_001005388.2. NP_001005389.2. NM_001005389.1. NP_001153803.1. NM_001160331.1. NP_001153804.1. NM_001160332.1. NP_001153805.1. NM_001160333.1. NP_055905.2. NM_015090.3. |
| NGRN | Neugrin | NGRN_HUMAN | Q9NPE2 | NP_001028260.2. NM_001033088.1. |
| NMU | Neuromedin U | NMU_HUMAN | P48645 | NP_006672.1 NM_006681.2 |
| NPTN | Neuroplastin | NPTN_HUMAN | Q9Y639 | NP_001154835.1. NM_001161363.1. NP_001154836.1. NM_001161364.1. NP_036560.1. NM_012428.3. NP_059429.1. NM_017455.3. |
| NPTX2 | Neuronal pentraxin-2 | NPTX2_HUMAN | P47972 | NP_002514.1. NM_002523.2. |
| NPY | Pro-neuropeptide Y | NPY_HUMAN | P01303 | NP_000896.1. NM_000905.3. |
| NTNG1 | Netrin-G1 | NTNG1_HUMAN | Q9Y2I2 | NP_001106697.1. NM_001113226.1. NP_001106699.1. NM_001113228.1. NP_055732.2. NM_014917.2. |
| NXPH1 | Neurexophilin-1 | NXPH1_HUMAN | P58417 | NP_689958.1. NM_152745.2. |
| NXPH2 | Neurexophilin-2 | NXPH2_HUMAN | O95156 | NP_009157.1. NM_007226.2. |
| ODZ4 | Teneurin-4 | TEN4_HUMAN | Q6N022 | NP_001092286.2. NM_001098816.2. |
| P4HA2 | Prolyl 4-hydroxylase subunit alpha-2 | P4HA2_HUMAN | O15460 | NP_001017973.1. NM_001017973.1. NP_001017974.1. NM_001017974.1. NP_001136070.1. NM_001142598.1. NP_001136071.1. NM_001142599.1. NP_004190.1. NM_004199.2. |
| PAM | Peptidyl-glycine | AMD_HUMAN | P19021 | NP_000910.2. |

TABLE 1-continued

β-Cell Mass Markers of the Invention.

| Marker Name | Protein Description | UNIPROT_ID | UNIPROT ACCESSION | GENBANK ACCESSION |
|---|---|---|---|---|
| | alpha-amidating monooxygenase | | | NM_000919.3. NP_001170777.1. NM_001177306.1. NP_620121.1. NM_138766.2. NP_620176.1. NM_138821.2. NP_620177.1. NM_138822.2. |
| PAPPA2 | Pappalysin-2 | PAPP2_HUMAN | Q9BXP8 | NP_064714.2. NM_020318.2. NP_068755.2. NM_021936.2. |
| PCSK1 | Neuroendocrine convertase 1 | NEC1_HUMAN | P29120 | NP_000430.3. NM_000439.4. |
| PCSK2 | Neuroendocrine convertase 2 | NEC2_HUMAN | P16519 | NP_001188457.1. NM_001201528.1. NP_001188458.1. NM_001201529.1. NP_002585.2. NM_002594.3. |
| PDYN | Proenkephalin-B | PDYN_HUMAN | P01213 | NP_001177821.1. NM_001190892.1. NP_001177827.1. NM_001190898.2. NP_001177828.1. NM_001190899.2. NP_001177829.1. NM_001190900.1. NP_077722.1. NM_024411.4. |
| PIP4K2A | Phosphatidylinositol 5-phosphate 4-kinase type-2 alpha | PI42A_HUMAN | P48426 | NP_005019.2. NM_005028.4. |
| PLBD2 | Putative phospholipase B-like 2 | PLBL2_HUMAN | Q8NHP8 | NP_775813.2. NM_173542.3. |
| PLCB4 | 1-phosphatidylinositol 4,5-bisphosphate phosphodiesterase beta-4 | PLCB4_HUMAN | Q15147 | NP_000924.3. NM_000933.3. NP_001166117.1. NM_001172646.1. NP_877949.2. NM_182797.2. |
| PLXNC1 | Plexin-C1 | PLXC1_HUMAN | O60486 | NP_005752.1. NM_005761.2. |
| PPAP2A | Lipid phosphate phosphohydrolase 1 | LPP1_HUMAN | O14494 | NP_003702.2. NM_003711.2. NP_795714.1. NM_176895.1. |
| PPFIA1 | Liprin-alpha-1 | LIPA1_HUMAN | Q13136 | NP_003617.1. NM_003626.3. NP_803172.1. NM_177423.2. |
| PPY | Pancreatic icosapeptide | PAHO_HUMAN | P01298 | NP_002713.1 NM_002722.3 |
| PRNP | Major prion protein | PRIO_HUMAN | P04156 | NP_000302.1. NM_000311.3. NP_001073590.1. NM_001080121.1. NP_001073591.1. NM_001080122.1. NP_001073592.1. NM_001080123.1. NP_898902.1. NM_183079.2. |
| PRSS3 | Trypsin-3 | TRY3_HUMAN | P35030 | NP_001184026.2. NM_001197097.2. NP_002762.2. NM_002771.3. NP_031369.2. NM_007343.3. |
| PTPRJ | Receptor-type tyrosine-protein phosphatase eta | PTPRJ_HUMAN | Q12913 | NP_001091973.1 NM_001098503.1 NP_002834.3 NM_002843.3 |
| PTPRN | Receptor-type | PTPRN_HUMAN | Q16849 | NP_001186692.1. |

TABLE 1-continued

β-Cell Mass Markers of the Invention.

| Marker Name | Protein Description | UNIPROT_ID | UNIPROT ACCESSION | GENBANK ACCESSION |
|---|---|---|---|---|
| | tyrosine-protein phosphatase-like N | | | NM_001199763.1. NP_001186693.1. NM_001199764.1. NP_002837.1. NM_002846.3. |
| PTPRN2 | Receptor-type tyrosine-protein phosphatase N2 | PTPR2_HUMAN | Q92932 | NP_002838.2. NM_002847.3. NP_570857.2. NM_130842.2. NP_570858.2. NM_130843.2. |
| PVR | Poliovirus receptor | PVR_HUMAN | P15151 | NP_001129240.1. NM_001135768.1. NP_001129241.1. NM_001135769.1. NP_001129242.1. NM_001135770.1. NP_006496.3. NM_006505.3. |
| QPCT | Glutaminyl-peptide cyclotransferase | QPCT_HUMAN | Q16769 | NP_036545.1. NM_012413.3. |
| REG3G | Regenerating islet-derived protein 3-gamma | REG3G_HUMAN | Q6UW15 | NP_001008388.1. NM_001008387.2. NP_001256969.1. NM_001270040.1. NP_940850.1. NM_198448.3. |
| RGS7 | Regulator of G-protein signaling 7 | RGS7_HUMAN | P49802 | NP_002915.3. NM_002924.4. |
| RIMBP2 | RIMS-binding protein 2 | RIMB2_HUMAN | O15034 | NP_056162.4. NM_015347.4. |
| SCAMP1 | Secretory carrier-associated membrane protein 1 | SCAM1_HUMAN | O15126 | NP_004857.4. NM_004866.4. |
| SCAMP2 | Secretory carrier-associated membrane protein 2 | SCAM2_HUMAN | O15127 | NP_005688.2. NM_005697.3. |
| SCAMP3 | Secretory carrier-associated membrane protein 3 | SCAM3_HUMAN | O14828 | NP_005689.2. NM_005698.3. NP_443069.1. NM_052837.2. |
| SCG2 | Secretogranin-2 | SCG2_HUMAN | P13521 | NP_003460.2. NM_003469.4. |
| SCG3 | Secretogranin-3 | SCG3_HUMAN | Q8WXD2 | NP_001158729.1. NM_001165257.1. NP_037375.2. NM_013243.3. |
| SCG5 | Neuroendocrine protein 7B2 | 7B2_HUMAN | P05408 | NP_001138229.1. NM_001144757.1. NP_003011.1. NM_003020.3. |
| SCGN | Secretagogin | SEGN_HUMAN | O76038 | NP_008929.2. NM_006998.3. |
| SDK2 | Protein sidekick-2 | SDK2_HUMAN | Q58EX2 | NP_001138424.1. NM_001144952.1. |
| SEMA3A | Semaphorin-3A | SEM3A_HUMAN | Q14563 | NP_006071.1. NM_006080.2. |
| SEMA3C | Semaphorin-3C | SEM3C_HUMAN | Q99985 | NP_006370.1. NM_006379.3. |
| SEPT3 | Neuronal-specific septin-3 | SEPT3_HUMAN | Q9UH03 | NP_061979.3 NM_019106.5 NP_663786.2 NM_145733.2 |
| SERPINB13 | Serpin B13 | SPB13_HUMAN | Q9UIV8 | NP_036529.1 NM_012397.3 |
| SERPINI1 | Neuroserpin | NEUS_HUMAN | Q99574 | NP_001116224.1. NM_001122752.1. NP_005016.1. NM_005025.4. |
| SEZ6L2 | Seizure 6-like protein 2 | SE6L2_HUMAN | Q6UXD5 | NP_001107571.1. NM_001114099.2. NP_001107572.1. NM_001114100.2. NP_001230261.1. NM_001243332.1. |

TABLE 1-continued

β-Cell Mass Markers of the Invention.

| Marker Name | Protein Description | UNIPROT_ID | UNIPROT ACCESSION | GENBANK ACCESSION |
|---|---|---|---|---|
| | | | | NP_001230262.1. NM_001243333.1. NP_036542.1. NM_012410.3. NP_963869.2. NM_201575.3. |
| SFT2D3 | Vesicle transport protein SFT2C | SFT2C_HUMAN | Q58I9 | NP_116129.3. NM_032740.3. |
| SHANK2 | SH3 and multiple ankyrin repeat domains protein 2 | SHAN2_HUMAN | Q9UPX8 | NP_036441.2. NM_012309.3. |
| SLC2A13 | Proton myo-inositol cotransporter | MYCT_HUMAN | Q96QE2 | NP_443117.3. NM_052885.3. |
| SLC30A1 | Zinc transporter 1 | ZNT1_HUMAN | Q9Y6M5 | NP_067017.2. NM_021194.2. |
| SLC39A14 | Zinc transporter ZIP14 | S39AE_HUMAN | Q15043 | NP_001121903.1. NM_001128431.2. NP_001128625.1. NM_001135153.1. NP_001128626.1. NM_001135154.1. NP_056174.2. NM_015359.4. |
| SLIT3 | Slit homolog 3 | SLIT3_HUMAN | O75094 | NP_003053.1 NM_003062.2 |
| SNAP25 | Synaptosomal-associated protein 25 | SNP25_HUMAN | P60880 | NP_003072.2. NM_003081.3. NP_570824.1. NM_130811.2. |
| SNAPIN | SNARE-associated protein Snapin | SNAPN_HUMAN | O95295 | NP_036569.1. NM_012437.5. |
| SORCS2 | VPS10 domain-containing receptor SorCS2 | SORC2_HUMAN | Q96PQ0 | NP_065828.2. NM_020777.2. |
| SPARCL1 | SPARC-like protein 1 | SPRL1_HUMAN | Q14515 | NP_001121782.1. NM_001128310.1. NP_004675.3. NM_004684.4. |
| SPCS3 | Signal peptidase complex subunit 3 | SPCS3_HUMAN | P61009 | NP_068747.1. NM_021928.3. |
| SPOCK1 | Testican-1 | TICN1_HUMAN | Q08629 | NP_004589.1. NM_004598.3. |
| STK10 | Serine/threonine-protein kinase 10 | STK10_HUMAN | O94804 | NP_005981.3. NM_005990.3. |
| STX1A | Syntaxin-1A | STX1A_HUMAN | Q16623 | NP_001159375.1 NM_001165903.1 NP_004594.1 NM_004603.3 |
| STX2 | Syntaxin-2 | STX2_HUMAN | P32856 | NP_001971.2. NM_001980.3. NP_919337.1. NM_194356.2. |
| SV2A | Synaptic vesicle glycoprotein 2A | SV2A_HUMAN | Q7L0J3 | NP_055664.3. NM_014849.3. |
| SVIP | Small VCP/p97-interacting protein | SVIP_HUMAN | Q8NHG7 | NP_683691.1. NM_148893.1. |
| SYN1 | Synapsin-1 | SYN1_HUMAN | P17600 | NP_008881.2. NM_006950.3. NP_598006.1. NM_133499.2. |
| SYNPO | Synaptopodin | SYNPO_HUMAN | Q8N3V7 | NP_001103444.1. NM_001109974.2. NP_001159680.1. NM_001166208.1. NP_001159681.1. NM_001166209.1. NP_009217.3. NM_007286.5. |
| SYT7 | Synaptotagmin-7 | SYT7_HUMAN | O43581 | NP_004191.2. NM_004200.3. |
| TACSTD2 | Tumor-associated calcium signal transducer 2 | TACD2_HUMAN | P09758 | NP_002344.2. NM_002353.2. |
| TCN2 | Transcobalamin-2 | TCO2_HUMAN | P20062 | NP_000346.2. |

TABLE 1-continued

β-Cell Mass Markers of the Invention.

| Marker Name | Protein Description | UNIPROT_ID | UNIPROT ACCESSION | GENBANK ACCESSION |
|---|---|---|---|---|
| | | | | NM_000355.3. NP_001171655.1. NM_001184726.1. |
| TLL2 | Tolloid-like protein 2 | TLL2_HUMAN | Q9Y6L7 | NP_036597.1. NM_012465.3. |
| TM9SF3 | Transmembrane 9 superfamily member 3 | TM9S3_HUMAN | Q9HD45 | NP_064508.3. NM_020123.3. |
| TMEM106B | Transmembrane protein 106B | T106B_HUMAN | Q9NUM4 | NP_001127704.1. NM_001134232.1. NP_060844.2. NM_018374.3. |
| TMEM119 | Transmembrane protein 119 | TM119_HUMAN | Q4V9L6 | NP_859075.2. NM_181724.2. |
| TMEM132A | Transmembrane protein 132A | T132A_HUMAN | Q24JP5 | NP_060340.2. NM_017870.3. NP_821174.1. NM_178031.2. |
| TMPRSS11F | Transmembrane protease serine 11F | TM11F_HUMAN | Q6ZWK6 | NP_997290.2. NM_207407.2. |
| TNFSF11 | Tumor necrosis factor ligand superfamily member 11 | TNF11_HUMAN | O14788 | NP_003692.1. NM_003701.3. NP_143026.1. NM_033012.3. |
| TNFSF4 | Tumor necrosis factor ligand superfamily member 4 | TNFL4_HUMAN | P23510 | NP_003317.1. NM_003326.3. |
| TTC7B | Tetratricopeptide repeat protein 7B | TTC7B_HUMAN | Q86TV6 | NP_001010854.1. NM_001010854.1. |
| TXNDC5 | Thioredoxin domain-containing protein 5 | TXND5_HUMAN | Q8NBS9 | NP_001139021.1. NM_001145549.2. NP_110437.2. NM_030810.3. |
| UBL3 | Ubiquitin-like protein 3 | UBL3_HUMAN | O95164 | NP_009037.1. NM_007106.3. |
| UCHL1 | Ubiquitin carboxyl-terminal hydrolase isozyme L1 | UCHL1_HUMAN | P09936 | NP_004172.2. NM_004181.4. |
| VAMP4 | Vesicle-associated membrane protein 4 | VAMP4_HUMAN | O75379 | NP_001172056.1. NM_001185127.1. NP_003753.2. NM_003762.4. |
| VAT1L | Synaptic vesicle membrane protein VAT-1 homolog-like | VAT1L_HUMAN | Q9HCJ6 | NP_065978.1. NM_020927.1. |
| VAV3 | Guanine nucleotide exchange factor VAV3 | VAV3_HUMAN | Q9UKW4 | NP_001073343.1. NM_001079874.1. NP_006104.4. NM_006113.4. |
| VGF | Neurosecretory protein VGF | VGF_HUMAN | O15240 | NP_003369.2. NM_003378.3. |
| VWA5B2 | von Willebrand factor A domain-containing protein 5B2 | VW5B2_HUMAN | Q8N398 | NP_612354.1. NM_138345.1. |
| WFDC5 | WAP four-disulfide core domain protein 5 | WFDC5_HUMAN | Q8TCV5 | NP_663627.1. NM_145652.3. |
| WFS1 | Wolframin | WFS1_HUMAN | O76024 | NP_001139325.1. NM_001145853.1. NP_005996.2. NM_006005.3. |
| WNT5A | Protein Wnt-5a | WNT5A_HUMAN | P41221 | NP_001243034.1. NM_001256105.1. NP_003383.2. NM_003392.4. |
| WNT9B | Protein Wnt-9b | WNT9B_HUMAN | O14905 | NP_003387.1. NM_003396.1. |

TABLE 2

β-Cell Function Markers of the Invention.

| Marker Name | Protein Description | UNIPROT_ID | UNIPROT ACCESSION | GENBANK ACCESSION |
|---|---|---|---|---|
| ABCC9 | ATP-binding cassette sub-family C member 9 | ABCC9_HUMAN | O60706 | NP_005682.2. NM_005691.2. NP_064693.2. NM_020297.2. |
| ASNS | Asparagine synthetase [glutamine-hydrolyzing] | ASNS_HUMAN | P08243 | NP_001171546.1. NM_001178075.1. NP_001171547.1. NM_001178076.1. NP_001171548.1. NM_001178077.1. NP_001664.3. NM_001673.4. NP_597680.2. NM_133436.3. NP_899199.2. NM_183356.3. |
| GATC | Glutamyl-tRNA(Gln) amidotransferase subunit C, mitochondrial | GATC_HUMAN | O43716 | NP_789788.1. NM_176818.2. |
| MMP7 | Matrilysin | MMP7_HUMAN | P09237 | NP_002414.1. NM_002423.3. |
| OLFM4 | Olfactomedin-4 | OLFM4_HUMAN | Q6UX06 | NP_006409.3. NM_006418.4. |
| SERPINE1 | Plasminogen activator inhibitor 1 | PAI1_HUMAN | P05121 | NP_000593.1. NM_000602.4. NP_001158885.1. NM_001165413.2. |
| SMPDL3B | Acid sphingomyelinase-like phosphodiesterase 3b | ASM3B_HUMAN | Q92485 | NP_001009568.1. NM_001009568.1. NP_055289.2. NM_014474.2. |
| ADAM9 | Disintegrin and metalloproteinase domain-containing protein 9 | ADAM9_HUMAN | Q13443 | NP_003807.1. NM_003816.2. |
| C8orf55 | UPF0670 protein THEM6 | THEM6_HUMAN | Q8WUY1 | NP_057731.1. NM_016647.2. |
| CCL20 | C-C motif chemokine 20 | CCL20_HUMAN | P78556 | NP_001123518.1. NM_001130046.1. NP_004582.1. NM_004591.2. |
| GDF15 | Growth/differentiation factor 15 | GDF15_HUMAN | Q99988 | NP_004855.2. NM_004864.2. |
| IL32 | Interleukin-32 | IL32_HUMAN | P24001 | NP_001012649.1. NM_001012631.1. NP_001012650.1. NM_001012632.1. NP_001012651.1. NM_001012633.1. NP_001012652.1. NM_001012634.1. NP_001012653.1. NM_001012635.1. NP_001012736.1. NM_001012718.1. NP_004212.4. NM_004221.4. |
| MMP14 | Matrix metalloproteinase-14 | MMP14_HUMAN | P50281 | NP_004986.1. NM_004995.2. |
| SERPINB2 | Plasminogen activator inhibitor 2 | PAI2_HUMAN | P05120 | NP_001137290.1. NM_001143818.1. NP_002566.1. NM_002575.2. |
| SPINT1 | Kunitz-type protease inhibitor 1 | SPIT1_HUMAN | O43278 | NP_001027539.1. NM_001032367.1. NP_003701.1. NM_003710.3. NP_857593.1. NM_181642.2. |
| TNFAIP2 | Tumor necrosis factor alpha-induced protein 2 | TNAP2_HUMAN | Q03169 | NP_006282.2. NM_006291.2. |
| MMP1 | Interstitial collagenase | MMP1_HUMAN | P03956 | NP_002412.1. NM_002421.3. |
| SPINT2 | Kunitz-type protease inhibitor 2 | SPIT2_HUMAN | O43291 | NP_001159575.1. NM_001166103.1. NP_066925.1. NM_021102.3. |
| COL3A1 | Collagen alpha-1(III) chain | CO3A1_HUMAN | P02461 | NP_000081.1. NM_000090.3. |
| YBX1 | Nuclease-sensitive element-binding protein 1 | YBOX1_HUMAN | P67809 | NP_004550.2. NM_004559.3. |
| GHRL | Appetite-regulating hormone | GHRL_HUMAN | Q9UBU3 | NP_001128413.1. NM_001134941.1. NP_001128416.1. NM_001134944.1. NP_001128417.1. NM_001134945.1. NP_001128418.1. NM_001134946.1. NP_057446.1. NM_016362.3. |
| B4GALT1 | Beta-1,4-galactosyltransferase 1 | B4GT1_HUMAN | P15291 | NP_001488.2. NM_001497.3. |
| ACP2 | Lysosomal acid phosphatase | PPAL_HUMAN | P11117 | NP_001601.1. NM_001610.2. |
| ACSL3 | Long-chain-fatty-acid-CoA ligase 3 | ACSL3_HUMAN | O95573 | NP_004448.2. NM_004457.3. NP_976251.1. NM_203372.1. |
| ATP6AP2 | Renin receptor | RENR_HUMAN | O75787 | NP_005756.2. NM_005765.2. |
| B3GAT3 | Galactosylgalactosyl-xylosylprotein 3- | B3GA3_HUMAN | O94766 | NP_036332.2. NM_012200.3. |

TABLE 2-continued

β-Cell Function Markers of the Invention.

| Marker Name | Protein Description | UNIPROT_ID | UNIPROT ACCESSION | GENBANK ACCESSION |
|---|---|---|---|---|
| | beta-glucuronosyltransferase 3 | | | |
| CA4 | Carbonic anhydrase 4 | CAH4_HUMAN | P22748 | NP_000708.1. NM_000717.3. |
| CAPNS1 | Calpain small subunit 1 | CPNS1_HUMAN | P04632 | NP_001003962.1. NM_001003962.1. NP_001740.1. NM_001749.2. |
| CIB1 | Calcium and integrin-binding protein 1 | CIB1_HUMAN | Q99828 | NP_006375.2. NM_006384.3. |
| CYB5R1 | NADH-cytochrome b5 reductase 1 | NB5R1_HUMAN | Q9UHQ9 | NP_057327.2. NM_016243.2. |
| EPHB2 | Ephrin type-B receptor 2 | EPHB2_HUMAN | P29323 | NP_004433.2. NM_004442.6. NP_059145.2. NM_017449.3. |
| FUT3 | Galactoside 3(4)-L-fucosyltransferase | FUT3_HUMAN | P21217 | NP_000140.1. NM_000149.3. NP_001091108.1. NM_001097639.1. NP_001091109.1. NM_001097640.1. NP_001091110.1. NM_001097641.1. |
| FUT6 | Alpha-(1,3)-fucosyltransferase | FUT6_HUMAN | P51993 | NP_000141.1. NM_000150.1. NP_001035791.1. NM_001040701.1. |
| FXYD2 | Sodium/potassium-transporting ATPase subunit gamma | ATNG_HUMAN | P54710 | NP_001671.2. NM_001680.4. NP_067614.1. NM_021603.3. |
| HTATIP2 | Oxidoreductase HTATIP2 | HTAI2_HUMAN | Q9BUP3 | NP_001091990.1. NM_001098520.1. NP_001091991.1. NM_001098521.1. NP_001091992.1. NM_001098522.1. NP_001091993.1. NM_001098523.1. NP_006401.3. NM_006410.4. |
| LCN2 | Neutrophil gelatinase-associated lipocalin | NGAL_HUMAN | P80188 | NP_005555.2. NM_005564.3. |
| LMAN2 | Vesicular integral-membrane protein VIP36 | LMAN2_HUMAN | Q12907 | NP_006807.1. NM_006816.2. |
| MAN1A2 | Mannosyl-oligosaccharide 1,2-alpha-mannosidase IB | MA1A2_HUMAN | O60476 | NP_006690.1. NM_006699.3. |
| PLSCR3 | Phospholipid scramblase 3 | PLS3_HUMAN | Q9NRY6 | NP_001188505.1. NM_001201576.1. NP_065093.2. NM_020360.3. |
| PMVK | Phosphomevalonate kinase | PMVK_HUMAN | Q15126 | NP_006547.1. NM_006556.3. |
| PTTG1IP | Pituitary tumor-transforming gene 1 protein-interacting protein | PTTG_HUMAN | P53801 | NP_004330.1. NM_004339.3. |
| TMED2 | Transmembrane emp24 domain-containing protein 2 | TMED2_HUMAN | Q15363 | NP_006806.1. NM_006815.3. |
| VAMP1 | Vesicle-associated membrane protein 1 | VAMP1_HUMAN | P23763 | NP_055046.1. NM_014231.3. NP_058439.1. NM_016830.2. NP_954740.1. NM_199245.1. |
| VAMP7 | Vesicle-associated membrane protein 7 | VAMP7_HUMAN | P51809 | NP_001138621.1. NM_001145149.2. NP_001172112.1. NM_001185183.1. NP_005629.1. NM_005638.5. |
| ABHD12 | Monoacylglycerol lipase ABHD12 | ABD12_HUMAN | Q8N2K0 | NP_001035937.1. NM_001042472.2. NP_056415.1. NM_015600.4. |
| ALG5 | Dolichyl-phosphate beta-glucosyltransferase | ALG5_HUMAN | Q9Y673 | NP_001135836.1. NM_001142364.1. NP_037470.1. NM_013338.4. |
| ALOX12B | Arachidonate 12-lipoxygenase, 12R-type | LX12B_HUMAN | O75342 | NP_001130.1. NM_001139.2. |
| AMPD3 | AMP deaminase 3 | AMPD3_HUMAN | Q01432 | NP_000471.1. NM_000480.2. NP_001020560.1. NM_001025389.1. NP_001020561.1. NM_001025390.1. NP_001165901.1. NM_001172430.1. NP_001165902.1. NM_001172431.1. |
| API5 | Apoptosis inhibitor 5 | API5_HUMAN | Q9BZZ5 | NP_001136402.1. NM_001142930.1. NP_001136403.1. NM_001142931.1. NP_001230676.1. NM_001243747.1. NP_006586.1. NM_006595.3. |
| ARMC10 | Armadillo repeat-containing protein | ARM10_HUMAN | Q8N2F6 | NP_001154481.1. NM_001161009.2. NP_001154482.1. NM_001161010.2. |

TABLE 2-continued

β-Cell Function Markers of the Invention.

| Marker Name | Protein Description | UNIPROT_ID | UNIPROT ACCESSION | GENBANK ACCESSION |
|---|---|---|---|---|
| | 10 | | | NP_001154483.1. NM_001161011.2. NP_001154484.1. NM_001161012.2. NP_001154485.1. NM_001161013.2. NP_114111.2. NM_031905.4. |
| ARMCX3 | Armadillo repeat-containing X-linked protein 3 | ARMX3_HUMAN | Q9UH62 | NP_057691.1. NM_016607.3. NP_808816.1. NM_177947.2. NP_808817.1. NM_177948.2. |
| ASPH | Aspartyl/asparaginyl beta-hydroxylase | ASPH_HUMAN | Q12797 | NP_001158222.1. NM_001164750.1. NP_001158223.1. NM_001164751.1. NP_001158225.1. NM_001164753.1. NP_001158227.1. NM_001164755.1. NP_001158228.1. NM_001164756.1. NP_004309.2. NM_004318.3. NP_064549.1. NM_020164.4. NP_115855.1. NM_032466.3. NP_115856.1. NM_032467.3. NP_115857.1. NM_032468.4. |
| ATAD3A | ATPase family AAA domain-containing protein 3A | ATD3A_HUMAN | Q9NVI7 | NP_001164006.1. NM_001170535.1. NP_001164007.1. NM_001170536.1. NP_060658.3. NM_018188.3. |
| ATAD3B | ATPase family AAA domain-containing protein 3B | ATD3B_HUMAN | Q5T9A4 | NP_114127.3. NM_031921.4. |
| ATAD3C | ATPase family AAA domain-containing protein 3C | ATD3C_HUMAN | Q5T2N8 | NP_001034300.2. NM_001039211.2. |
| BRP44 | Mitochondrial pyruvate carrier 2 | MPC2_HUMAN | O95563 | NP_001137146.1. NM_001143674.2. NP_056230.1. NM_015415.3. |
| C19orf68 | Uncharacterized protein C19orf68 | CS068_HUMAN | Q86XI8 | BC043386 AAH43386.1. |
| CCDC56 | Cytochrome C oxidase assembly factor 3 homolog, mitochondrial | COA3_HUMAN | Q9Y2R0 | NP_001035521.1. NM_001040431.1. |
| CEACAM7 | Carcinoembryonic antigen-related cell adhesion molecule 7 | CEAM7_HUMAN | Q14002 | NP_008821.1. NM_006890.3. |
| CISD2 | CDGSH iron-sulfur domain-containing protein 2 | CISD2_HUMAN | Q8N5K1 | NP_001008389.1. NM_001008388.4. |
| CPM | Carboxypeptidase M | CBPM_HUMAN | P14384 | NP_001005502.1. NM_001005502.2. NP_001865.1. NM_001874.4. NP_938079.1. NM_198320.3. |
| CTBP1 | C-terminal-binding protein 1 | CTBP1_HUMAN | Q13363 | NP_001012632.1. NM_001012614.1. NP_001319.1. NM_001328.2. |
| CTBP2 | C-terminal-binding protein 2 | CTBP2_HUMAN | P56545 | NP_001077383.1. NM_001083914.1. NP_001320.1. NM_001329.2. NP_073713.2. NM_022802.2. |
| CUZD1 | CUB and zona pellucida-like domain-containing protein 1 | CUZD1_HUMAN | Q86UP6 | NP_071317.2. NM_022034.5. |
| DDRGK1 | DDRGK domain-containing protein 1 | DDRGK_HUMAN | Q96HY6 | NP_076424.1. NM_023935.1. |
| DHRS7B | Dehydrogenase/reductase SDR family member 7B | DRS7B_HUMAN | Q6IAN0 | NP_056325.2. NM_015510.4. |
| EDF1 | Endothelial differentiation-related factor 1 | EDF1_HUMAN | O60869 | NP_003783.1. NM_003792.2. NP_694880.1. NM_153200.1. |
| ELMOD2 | ELMO domain-containing protein 2 | ELMD2_HUMAN | Q8IZ81 | NP_714913.1. NM_153702.3. |
| ENAH | Protein enabled homolog | ENAH_HUMAN | Q8N8S7 | NP_001008493.1. NM_001008493.1. NP_060682.2. NM_018212.4. |
| FAM174A | Membrane protein FAM174A | F174A_HUMAN | Q8TBP5 | NP_940909.1. NM_198507.1. |
| FAP | Seprase | SEPR_HUMAN | Q12884 | NP_004451.2. NM_004460.2. |
| FER | Tyrosine-protein kinase Fer | FER_HUMAN | P16591 | NP_005237.2. NM_005246.2. |
| GAD2 | Glutamate decarboxylase 2 | DCE2_HUMAN | Q05329 | NP_000809.1. NM_000818.2. NP_001127838.1. NM_001134366.1. |
| GAPDHS | Glyceraldehyde-3-phosphate dehydrogenase, testis-specific | G3PT_HUMAN | O14556 | NP_055179.1. NM_014364.4. |

TABLE 2-continued

β-Cell Function Markers of the Invention.

| Marker Name | Protein Description | UNIPROT_ID | UNIPROT ACCESSION | GENBANK ACCESSION |
|---|---|---|---|---|
| HK2 | Hexokinase-2 | HXK2_HUMAN | P52789 | NP_000180.2. NM_000189.4. |
| HK3 | Hexokinase-3 | HXK3_HUMAN | P52790 | NP_002106.2. NM_002115.2. |
| HKDC1 | Putative hexokinase HKDC1 | HKDC1_HUMAN | Q2TB90 | NP_079406.3. NM_025130.3. |
| HSD17B2 | Estradiol 17-beta-dehydrogenase 2 | DHB2_HUMAN | P37059 | NP_002144.1. NM_002153.2. |
| HSF2BP | Heat shock factor 2-binding protein | HSF2B_HUMAN | O75031 | NP_008962.1. NM_007031.1. |
| IFNGR1 | Interferon gamma receptor 1 | INGR1_HUMAN | P15260 | NP_000407.1. NM_000416.2. |
| ILF2 | Interleukin enhancer-binding factor 2 | ILF2_HUMAN | Q12905 | NP_001254738.1. NM_001267809.1. NP_004506.2. NM_004515.3. |
| ITGB6 | Integrin beta-6 | ITB6_HUMAN | P18564 | NP_000879.2. NM_000888.3. |
| KIAA0090 | ER membrane protein complex subunit 1 | EMC1_HUMAN | Q8N766 | NP_001258356.1. NM_001271427.1. NP_001258357.1. NM_001271428.1. NP_001258358.1. NM_001271429.1. NP_055862.1. NM_015047.2. |
| KIAA0776 | E3 UFM1-protein ligase 1 | UFL1_HUMAN | O94874 | NP_056138.1. NM_015323.4. |
| KIAA2013 | Uncharacterized protein KIAA2013 | K2013_HUMAN | Q8IYS2 | NP_612355.1. NM_138346.2. |
| KLRAQ1 | Protein phosphatase 1 regulatory subunit 21 | PPR21_HUMAN | Q6ZMI0 | NP_001129101.1. NM_001135629.2. NP_001180404.1. NM_001193475.1. NP_694539.1. NM_152994.4. |
| LAMTOR1 | Ragulator complex protein LAMTOR1 | LTOR1_HUMAN | Q6IAA8 | NP_060377.1. NM_017907.2. |
| LAMTOR2 | Ragulator complex protein LAMTOR2 | LTOR2_HUMAN | Q9Y2Q5 | NP_001138736.1. NM_001145264.1. NP_054736.1. NM_014017.3. |
| LAMTOR3 | Ragulator complex protein LAMTOR3 | LTOR3_HUMAN | Q9UHA4 | NP_068805.1. NM_021970.3. |
| LRRC63 | Leucine-rich repeat-containing protein 63 | LRC63_HUMAN | Q05C16 | CAI12166.2. BC030276 AAH30276.1. |
| MFN2 | Mitofusin-2 | MFN2_HUMAN | O95140 | NP_001121132.1. NM_001127660.1. NP_055689.1. NM_014874.3. |
| MGAT4B | Alpha-1,3-mannosyl-glycoprotein 4-beta acetylglucosaminyl transferase B | MGT4B_HUMAN | Q9UQ53 | NP_055090.1. NM_014275.4. NP_463459.1. NM_054013.3. |
| MLF2 | Myeloid leukemia factor 2 | MLF2_HUMAN | Q15773 | NP_005430.1. NM_005439.2. |
| MOGS | Mannosyl-oligosaccharide glucosidase | MOGS_HUMAN | Q13724 | NP_001139630.1. NM_001146158.1. NP_006293.2. NM_006302.2. |
| MTMR11 | Myotubularin-related protein 11 | MTMRB_HUMAN | A4FU01 | NP_001139334.1. NM_001145862.1. NP_870988.2. NM_181873.3. |
| MTX1 | Metaxin-1 | MTX1_HUMAN | Q13505 | NP_002446.2. NM_002455.3. NP_942584.1. NM_198883.2. |
| NCEH1 | Neutral cholesterol ester hydrolase 1 | NCEH1_HUMAN | Q6PIU2 | NP_001139748.1. NM_001146276.1. NP_001139749.1. NM_001146277.1. NP_001139750.1. NM_001146278.1. NP_065843.3. NM_020792.4. |
| OCIAD2 | OCIA domain-containing protein 2 | OCAD2_HUMAN | Q56VL3 | NP_001014446.1. NM_001014446.1. NP_689611.1. NM_152398.2. |
| PDE8B | High affinity cAMP-specific and IBMX-insensitive 3',5'-cyclic phosphodiesterase 8B | PDE8B_HUMAN | O95263 | NP_001025022.1. NM_001029851.2. NP_001025023.1. NM_001029852.2. NP_001025024.1. NM_001029853.2. NP_001025025.1. NM_001029854.2. NP_003710.1. NM_003719.3. |
| PFKFB1 | 6-phosphofructo-2-kinase/fructose-2,6-bisphosphatase 1 | F261_HUMAN | P16118 | NP_002616.2. NM_002625.2. |
| PIGK | GPI-anchor transamidase | GPI8_HUMAN | Q92643 | NP_005473.1. NM_005482.2. |
| PLEKHH2 | Pleckstrin homology domain-containing family H member 2 | PKHH2_HUMAN | Q8IVE3 | NP_742066.2. NM_172069.3. |
| PRUNE2 | Protein prune homolog 2 | PRUN2_HUMAN | Q8WUY3 | NP_056040.2. NM_015225.2. |
| RDH11 | Retinol | RDH11_HUMAN | Q8TC12 | NP_057110.3. NM_016026.3. |

TABLE 2-continued

β-Cell Function Markers of the Invention.

| Marker Name | Protein Description | UNIPROT_ID | UNIPROT ACCESSION | GENBANK ACCESSION |
|---|---|---|---|---|
| | dehydrogenase 11 | | | |
| RIC8A | Synembryn-A | RIC8A_HUMAN | Q9NPQ8 | NP_068751.4. NM_021932.4. |
| RUFY3 | Protein RUFY3 | RUFY3_HUMAN | Q7L099 | NP_001032519.1. NM_001037442.2. NP_001124181.1. NM_001130709.1. NP_055776.1. NM_014961.3. |
| SDK1 | Protein sidekick-1 | SDK1_HUMAN | Q7Z5N4 | NP_689957.3. NM_152744.3. |
| SORCS3 | VPS10 domain-containing receptor SorCS3 | SORC3_HUMAN | Q9UPU3 | NP_055793.1. NM_014978.1. |
| SPTLC1 | Serine palmitoyltransferase 1 | SPTC1_HUMAN | O15269 | NP_006406.1. NM_006415.2. NP_847894.1. NM_178324.1. |
| STOML3 | Stomatin-like protein 3 | STML3_HUMAN | Q8TAV4 | NP_001137505.1. NM_001144033.1. NP_660329.1. NM_145286.2. |
| STX1B | Syntaxin-1B | STX1B_HUMAN | P61266 | NP_443106.1. NM_052874.3. |
| SYT5 | Synaptotagmin-5 | SYT5_HUMAN | O00445 | NP_003171.2. NM_003180.2. |
| TBL2 | Transducin beta-like protein 2 | TBL2_HUMAN | Q9Y4P3 | NP_036585.1. NM_012453.2. |
| TGOLN2 | Trans-Golgi network integral membrane protein 2 | TGON2_HUMAN | O43493 | NP_001193769.1. NM_001206840.1. NP_001193770.1. NM_001206841.1. NP_001193773.1. NM_001206844.1. NP_006455.2. NM_006464.3. |
| THSD7A | Thrombospondin type-1 domain-containing protein 7A | THS7A_HUMAN | Q9UPZ6 | NP_056019.1. NM_015204.2. |
| TMCO1 | Transmembrane and coiled-coil domain-containing protein 1 | TMCO1_HUMAN | Q9UM00 | NP_061899.2. NM_019026.4. |
| TMEM123 | Porimin | PORIM_HUMAN | Q8N131 | NP_443164.2. NM_052932.2. |
| TMPRSS13 | Transmembrane protease serine 13 | TMPSD_HUMAN | Q9BYE2 | NP_001193719.1. NM_001206790.1. NP_001231924.1. NM_001244995.1. |
| TMX4 | Thioredoxin-related transmembrane protein 4 | TMX4_HUMAN | Q9H1E5 | NP_066979.2. NM_021156.2. |
| TNPO2 | Transportin-2 | TNPO2_HUMAN | O14787 | NP_001129667.1. NM_001136195.1. NP_001129668.1. NM_001136196.1. NP_038461.2. NM_013433.4. |
| TPBG | Trophoblast glycoprotein | TPBG_HUMAN | Q13641 | NP_001159864.1. NM_001166392.1. NP_006661.1. NM_006670.4. |
| TRIM42 | Tripartite motif-containing protein 42 | TRI42_HUMAN | Q8IWZ5 | NP_689829.3. NM_152616.4. |
| TTC37 | Tetratricopeptide repeat protein 37 | TTC37_HUMAN | Q6PGP7 | NP_055454.1. NM_014639.3. |
| USP9X | Probable ubiquitin carboxyl-terminal hydrolase FAF-X | USP9X_HUMAN | Q93008 | NP_001034679.2. NM_001039590.2. NP_001034680.2. NM_001039591.2. |
| VAPB | Vesicle-associated membrane protein-associated protein B/C | VAPB_HUMAN | O95292 | NP_001182606.1. NM_001195677.1. NP_004729.1. NM_004738.4. |
| VNN2 | Vascular non-inflammatory molecule 2 | VNN2_HUMAN | O95498 | NP_001229279.1. NM_001242350.1. NP_004656.2. NM_004665.2. NP_511043.1. NM_078488.1. |
| VPS26B | Vacuolar protein sorting-associated protein 26B | VP26B_HUMAN | Q4G0F5 | NP_443107.1. NM_052875.3. |
| YTHDF2 | YTH domain family protein 2 | YTHD2_HUMAN | Q9Y5A9 | NP_001166299.1. NM_001172828.1. NP_001166599.1. NM_001173128.1. NP_057342.2. NM_016258.2. |
| ZFPL1 | Zinc finger protein-like 1 | ZFPL1_HUMAN | O95159 | NP_006773.2. NM_006782.3. |

TABLE 3

Therapeutic Efficacy Markers of the Invention.

| Marker Name | Protein Description | UNIPROT_ID | UNIPROT ACCESSION | GENBANK ACCESSION |
|---|---|---|---|---|
| A2M | Alpha-2-macroglobulin | A2MG_HUMAN | P01023 | NP_000005.2<br>NM_000014.4 |
| ABI3BP | Target of Nesh-SH3 | TARSH_HUMAN | Q7Z7G0 | NP_056244.2<br>NM_015429.3 |
| ACE | Angiotensin-converting enzyme | ACE_HUMAN | P12821 | NP_000780.1<br>NM_000789.3<br>NP_001171528.1<br>NM_001178057.1<br>NP_690043.1<br>NM_152830.2 |
| ACTN1 | Alpha-actinin-1 | ACTN1_HUMAN | P12814 | NP_001093.1<br>NM_001102.3<br>NP_001123476.1<br>NM_001130004.1<br>NP_001123477.1<br>NM_001130005.1 |
| AFM | Afamin | AFAM_HUMAN | P43652 | NP_001124.1<br>NM_001133.2 |
| AGT | Angiotensinogen | ANGT_HUMAN | P01019 | NP_000020.1<br>NM_000029.3 |
| ALCAM | CD166 antigen | CD166_HUMAN | Q13740 | NP_001230209.1<br>NM_001243280.1<br>NP_001618.2<br>NM_001627.3 |
| ALDOB | Fructose-bisphosphate aldolase B | ALDOB_HUMAN | P05062 | NP_000026.2<br>NM_000035.3 |
| AMBP | Protein AMBP | AMBP_HUMAN | P02760 | NP_001624.1<br>NM_001633.3 |
| ANPEP | Aminopeptidase N | AMPN_HUMAN | P15144 | NP_001141.2<br>NM_001150.2 |
| AOC3 | Membrane primary amine oxidase | AOC3_HUMAN | Q16853 | NP_003725.1<br>NM_003734.2 |
| APOA1 | Apolipoprotein A-I | APOA1_HUMAN | P02647 | NP_000030.1<br>NM_000039.1 |
| APOA2 | Apolipoprotein A-II | APOA2_HUMAN | P02652 | NP_001634.1<br>NM_001643.1 |
| APOA4 | Apolipoprotein A-IV | APOA4_HUMAN | P06727 | M13654; ; AAA51744.1;<br>X13629; CAA31955.1;<br>BC074764; AAH74764.1;<br>BC113594; AAI13595.1;<br>BC113596; AAI13597.1;<br>M14566; AAA51748.1 |
| APOB | Apolipoprotein B-100 | APOB_HUMAN | P04114 | NP_000375.2<br>NM_000384.2 |
| APOC2 | Apolipoprotein C-II | APOC2_HUMAN | P02655 | NP_000474.2<br>NM_000483.4 |
| APOC3 | Apolipoprotein C-III | APOC3_HUMAN | P02656 | NP_000031.1<br>NM_000040.1 |
| APOC4 | Apolipoprotein C-IV | APOC4_HUMAN | P55056 | NP_001637.1<br>NM_001646.2 |
| APOE | Apolipoprotein E | APOE_HUMAN | P02649 | NP_000032.1<br>NM_000041.2 |
| ARHGDIA | Rho GDP-dissociation inhibitor 1 | GDIR1_HUMAN | P52565 | NP_001172006.1<br>NM_001185077.1<br>NP_001172007.1<br>NM_001185078.1<br>NP_004300.1<br>NM_004309.4 |
| ARHGDIB | Rho GDP-dissociation inhibitor 2 | GDIR2_HUMAN | P52566 | NP_001166.3<br>NM_001175.4 |
| ATRN | Attractin | ATRN_HUMAN | O75882 | NP_001193976.1<br>NM_001207047.1<br>NP_647537.1<br>NM_139321.2<br>NP_647538.1<br>NM_139322.2. |
| AZGP1 | Zinc-alpha-2-glycoprotein | ZA2G_HUMAN | P25311 | NP_001176.1<br>NM_001185.3 |
| B2M | Beta-2-microglobulin | B2MG_HUMAN | P61769 | NP_004039.1<br>NM_004048.2 |
| BST1 | ADP-ribosyl cyclase 2 | BST1_HUMAN | Q10588 | NP_004325.2<br>NM_004334.2 |
| BTD | Biotinidase | BTD_HUMAN | P43251 | NP_000051.1 |

TABLE 3-continued

Therapeutic Efficacy Markers of the Invention.

| Marker Name | Protein Description | UNIPROT_ID | UNIPROT ACCESSION | GENBANK ACCESSION |
|---|---|---|---|---|
| C1RL | Complement C1r subcomponent-like protein | C1RL_HUMAN | Q9NZP8 | NM_000060.2<br>NP_057630.2<br>NM_016546.2 |
| C4BPA | C4b-binding protein alpha chain | C4BPA_HUMAN | P04003 | NP_000706.1<br>NM_000715.3 |
| C9 | Complement component C9 | CO9_HUMAN | P02748 | NP_001728.1<br>NM_001737.3 |
| CA2 | Carbonic anhydrase 2 | CAH2_HUMAN | P00918 | NP_000058.1<br>NM_000067.2 |
| CACNA2D1 | Voltage-dependent calcium channel subunit alpha-2/delta-1 | CA2D1_HUMAN | P54289 | NP_000713.2<br>NM_000722.2 |
| CAP1 | Adenylyl cyclase-associated protein 1 | CAP1_HUMAN | Q01518 | NP_001099000.1<br>NM_001105530.1<br>NP_006358.1<br>NM_006367.3 |
| CD14 | Monocyte differentiation antigen CD14 | CD14_HUMAN | P08571 | NP_000582.1<br>NM_000591.3<br>NP_001035110.1<br>NM_001040021.2<br>NP_001167575.1<br>NM_001174104.1<br>NP_001167576.1<br>NM_001174105.1 |
| CD163 | Scavenger receptor cysteine-rich type 1 protein M130 | C163A_HUMAN | Q86VB7 | NP_004235.4<br>NM_004244.5<br>NP_981961.2<br>NM_203416.3 |
| CD5L | CD5 antigen-like | CD5L_HUMAN | O43866 | NP_005885.1<br>NM_005894.2 |
| CDH5 | Cadherin-5 | CADH5_HUMAN | P33151 | NP_001786.2<br>NM_001795.3 |
| CFD | Complement factor D | FAD_HUMAN | P00746 | NP_001919.2<br>NM_001928.2 |
| CLEC3B | Tetranectin | TETN_HUMAN | P05452 | NP_003269.2<br>NM_003278.2 |
| CLSTN1 | Calsyntenin-1 | CSTN1_HUMAN | O94985 | NP_001009566.1<br>NM_001009566.1<br>NP_055759.3<br>NM_014944.3 |
| CNDP1 | Beta-Ala-His dipeptidase | CNDP1_HUMAN | Q96KN2 | NP_116038.4<br>NM_032649.5 |
| CNN2 | Calponin-2 | CNN2_HUMAN | Q99439 | NP_004359.1<br>NM_004368.2<br>NP_958434.1<br>NM_201277.1 |
| COL6A1 | Collagen alpha-1(VI) chain | CO6A1_HUMAN | P12109 | NP_001839.2<br>NM_001848.2 |
| COL6A3 | Collagen alpha-3(VI) chain | CO6A3_HUMAN | P12111 | NP_004360.2<br>NM_004369.3<br>NP_476505.3<br>NM_057164.4<br>NP_476508.2<br>NM_057167.3 |
| CORO1A | Coronin-1A | COR1A_HUMAN | P31146 | NP_001180262.1<br>NM_001193333.2<br>NP_009005.1<br>NM_007074.3 |
| CPB2 | Carboxypeptidase B2 | CBPB2_HUMAN | Q96IY4 | NP_001863.2<br>NM_001872.3 |
| CRP | C-reactive protein | CRP_HUMAN | P02741 | NP_000558.2<br>NM_000567.2 |
| CRTAC1 | Cartilage acidic protein 1 | CRAC1_HUMAN | Q9NQ79 | NP_001193457.1<br>NM_001206528.2<br>NP_060528.3<br>NM_018058.6 |
| CTBS | Di--acetylchitobiase | DIAC_HUMAN | Q01459 | NP_004379.1<br>NM_004388.2 |
| DBH | Dopamine beta-hydroxylase | DOPO_HUMAN | P09172 | NP_000778.3<br>NM_000787.3 |
| DBNL | Drebrin-like protein | DBNL_HUMAN | Q9UJU6 | NP_001014436.1<br>NM_001014436.2<br>NP_001116428.1 |

TABLE 3-continued

Therapeutic Efficacy Markers of the Invention.

| Marker Name | Protein Description | UNIPROT_ID | UNIPROT ACCESSION | GENBANK ACCESSION |
|---|---|---|---|---|
| | | | | NM_001122956.1 |
| | | | | NP_054782.2 |
| | | | | NM_014063.6 |
| DPEP2 | Dipeptidase 2 | DPEP2_HUMAN | Q9H4A9 | NP_071750.1 |
| | | | | NM_022355.3 |
| ECM1 | Extracellular matrix protein 1 | ECM1_HUMAN | Q16610 | NP_001189787.1 |
| | | | | NM_001202858.1 |
| | | | | NP_004416.2 |
| | | | | NM_004425.3 |
| | | | | NP_073155.2 |
| | | | | NM_022664.2 |
| EFEMP1 | EGF-containing fibulin-like extracellular matrix protein 1 | FBLN3_HUMAN | Q12805 | NP_001034437.1 |
| | | | | NM_001039348.2 |
| | | | | NP_001034438.1 |
| | | | | NM_001039349.2 |
| ENPP2 | Ectonucleotide pyrophosphatase/ phosphodiesterase family member 2 | ENPP2_HUMAN | Q13822 | NP_001035181.1 |
| | | | | NM_001040092.2 |
| | | | | NP_001124335.1 |
| | | | | NM_001130863.2 |
| | | | | NP_006200.3 |
| | | | | NM_006209.4 |
| ERP29 | Endoplasmic reticulum resident protein 29 | ERP29_HUMAN | P30040 | NP_006808.1 |
| | | | | NM_006817.3 |
| F10 | Coagulation factor X | FA10_HUMAN | P00742 | NP_000495.1 |
| | | | | NM_000504.3 |
| F11 | Coagulation factor XI | FA11_HUMAN | P03951 | NP_000119.1 |
| | | | | NM_000128.3 |
| F12 | Coagulation factor XII | FA12_HUMAN | P00748 | NP_000496.2 |
| | | | | NM_000505.3 |
| F13B | Coagulation factor XIII B chain | F13B_HUMAN | P05160 | NP_001985.2 |
| | | | | NM_001994.2 |
| F9 | Coagulation factor IX | FA9_HUMAN | P00740 | NP_000124.1 |
| | | | | NM_000133.3 |
| FAM3B | Protein FAM3B | FAM3B_HUMAN | P58499 | NP_478066.3 |
| | | | | NM_058186.3 |
| | | | | NP_996847.1 |
| | | | | NM_206964.1 |
| FBLN1 | Fibulin-1 | FBLN1_HUMAN | P23142 | NP_001987.2 |
| | | | | NM_001996.3 |
| | | | | NP_006476.2 |
| | | | | NM_006485.3 |
| | | | | NP_006477.2 |
| | | | | NM_006486.2 |
| | | | | NP_006478.2 |
| | | | | NM_006487.2 |
| FCGBP | IgGFc-binding protein | FCGBP_HUMAN | Q9Y6R7 | NP_003881.2 |
| | | | | NM_003890.2 |
| FERMT3 | Fermitin family homolog 3 | URP2_HUMAN | Q86UX7 | NP_113659.3 |
| | | | | NM_031471.5 |
| | | | | NP_848537.1 |
| | | | | NM_178443.2 |
| FETUB | Fetuin-B | FETUB_HUMAN | Q9UGM5 | NP_055190.2 |
| | | | | NM_014375.2 |
| FLNA | Filamin-A | FLNA_HUMAN | P21333 | NP_001104026.1 |
| | | | | NM_001110556.1 |
| | | | | NP_001447.2 |
| | | | | NM_001456.3 |
| FN1 | Fibronectin | FINC_HUMAN | P02751 | NP_002017.1 |
| | | | | NM_002026.2 |
| | | | | NP_473375.2 |
| | | | | NM_054034.2 |
| | | | | NP_997639.1 |
| | | | | NM_212474.1 |
| | | | | NP_997641.1 |
| | | | | NM_212476.1 |
| | | | | NP_997643.1 |
| | | | | NM_212478.1 |
| | | | | NP_997647.1 |
| | | | | NM_212482.1 |
| FTH1 | Ferritin heavy chain | FRIH_HUMAN | P02794 | NP_002023.2 |
| | | | | NM_002032.2 |
| FTL | Ferritin light chain | FRIL_HUMAN | P02792 | NP_000137.2 |
| | | | | NM_000146.3 |
| GAPDH | Glyceraldehyde-3- | G3P_HUMAN | P04406 | NP_001243728.1 |

TABLE 3-continued

Therapeutic Efficacy Markers of the Invention.

| Marker Name | Protein Description | UNIPROT_ID | UNIPROT ACCESSION | GENBANK ACCESSION |
|---|---|---|---|---|
| | phosphate dehydrogenase | | | NM_001256799.1<br>NP_002037.2<br>NM_002046.4 |
| GPLD1 | Phosphatidylinositol-glycan-specific phospholipase D | PHLD_HUMAN | P80108 | NP_001494.2<br>NM_001503.3 |
| GPX3 | Glutathione peroxidase 3 | GPX3_HUMAN | P22352 | NP_002075.2<br>NM_002084.3 |
| GSN | Gelsolin | GELS_HUMAN | P06396 | NP_000168.1<br>NM_000177.4<br>NP_001121134.1<br>NM_001127662.1<br>NP_001121135.2<br>NM_001127663.1<br>NP_001121136.1<br>NM_001127664.1<br>NP_001121137.1<br>NM_001127665.1<br>NP_001121138.1<br>NM_001127666.1<br>NP_001121139.1<br>NM_001127667.1<br>NP_001244958.1<br>NM_001258029.1<br>NP_937895.1<br>NM_198252.2 |
| GSTP1 | Glutathione S-transferase P | GSTP1_HUMAN | P09211 | NP_000843.1<br>NM_000852.3 |
| HABP2 | Hyaluronan-binding protein 2 | HABP2_HUMAN | Q14520 | NP_001171131.1<br>NM_001177660.1<br>NP_004123.1<br>NM_004132.3 |
| HBA1 and HBA2 | Hemoglobin subunit alpha | HBA_HUMAN | P69905 | NP_000508.1<br>NM_000517.4<br>NP_000549.1<br>NM_000558.3 |
| HBD | Hemoglobin subunit delta | HBD_HUMAN | P02042 | NP_000510.1<br>NM_000519.3 |
| HGFAC | Hepatocyte growth factor activator | HGFA_HUMAN | Q04756 | NP_001519.1<br>NM_001528.2 |
| HPR | Haptoglobin-related protein | HPTR_HUMAN | P00739 | NP_066275.3<br>NM_020995.3 |
| HSPA8 | Heat shock cognate 71 kDa protein | HSP7C_HUMAN | P11142 | NP_006588.1<br>NM_006597.4<br>NP_694881.1<br>NM_153201.2 |
| HSPB1 | Heat shock protein beta-1 | HSPB1_HUMAN | P04792 | NP_001531.1<br>NM_001540.3 |
| HSPG2 | Basement membrane-specific heparan sulfate proteoglycan core protein | PGBM_HUMAN | P98160 | NP_005520.4<br>NM_005529.5 |
| IGF2 | Insulin-like growth factor II | IGF2_HUMAN | P01344 | NP_000603.1<br>NM_000612.4<br>NP_001007140.2<br>NM_001007139.4 |
| IGF2R | Cation-independent mannose-6-phosphate receptor | MPRI_HUMAN | P11717 | NP_000867.2<br>NM_000876.2 |
| IGFALS | Insulin-like growth factor-binding protein complex acid labile subunit | ALS_HUMAN | P35858 | NP_004961.1<br>NM_004970.2 |
| IGFBP3 | Insulin-like growth factor-binding protein 3 | IBP3_HUMAN | P17936 | NP_000589.2<br>NM_000598.4<br>NP_001013416.1<br>NM_001013398.1 |
| IGFBP4 | Insulin-like growth factor-binding protein 4 | P4_HUMAN | P22692 | NP_001543.2<br>NM_001552.2 |
| IGLL5 | Immunoglobulin lambda-like | IGLL5_HUMAN | B9A064 | NP_001171597.1<br>NM_001178126.1 |

TABLE 3-continued

Therapeutic Efficacy Markers of the Invention.

| Marker Name | Protein Description | UNIPROT_ID | UNIPROT ACCESSION | GENBANK ACCESSION |
|---|---|---|---|---|
| IL18BP | polypeptide 5 Interleukin-18-binding protein | I18BP_HUMAN | O95998 | NP_001034748.1<br>NM_001039659.1<br>NP_001034749.1<br>NM_001039660.1<br>NP_001138527.1<br>NM_001145055.1<br>NP_001138529.1<br>NM_001145057.1<br>NP_005690.2<br>NM_005699.3<br>NP_766630.2<br>NM_173042.2<br>NP_766632.2<br>NM_173044.2 |
| IL1RAP | Interleukin-1 receptor accessory protein | IL1AP_HUMAN | Q9NPH3 | NP_001161400.1<br>NM_001167928.1<br>NP_001161401.1<br>NM_001167929.1<br>NP_001161402.1<br>NM_001167930.1<br>NP_001161403.1<br>NM_001167931.1<br>NP_002173.1<br>NM_002182.3<br>NP_608273.1<br>NM_134470.3 |
| ILK | Integrin-linked protein kinase | ILK_HUMAN | Q13418 | NP_001014794.1.<br>NM_001014794.1.<br>NP_001014795.1.<br>NM_001014795.1.<br>NP_004508.1.<br>NM_004517.2. |
| ISLR | Immunoglobulin superfamily containing leucine-rich repeat protein | ISLR_HUMAN | O14498 | NP_005536.1<br>NM_005545.3<br>NP_958934.1<br>NM_201526.1 |
| ITIH3 | Inter-alpha-trypsin inhibitor heavy chain H3 | ITIH3_HUMAN | Q06033 | NP_002208.3<br>NM_002217.3 |
| ITIH4 | Inter-alpha-trypsin inhibitor heavy chain H3 | ITIH3_HUMAN | Q14624 | NP_002208.3<br>NM_002217.3 |
| LBP | Lipopolysaccharide-binding protein | LBP_HUMAN | P18428 | NP_004130.2<br>NM_004139.3 |
| LCAT | Phosphatidylcholine-sterol acyltransferase | LCAT_HUMAN | P04180 | NP_000220.1<br>NM_000229.1 |
| LRG1 | Leucine-rich alpha-2-glycoprotein | A2GL_HUMAN | P02750 | NP_443204.1<br>NM_052972.2 |
| LUM | Lumican | LUM_HUMAN | P51884 | NP_002336.1<br>NM_002345.3 |
| LYVE1 | Lymphatic vessel endothelial hyaluronic acid receptor 1 | LYVE1_HUMAN | Q9Y5Y7 | NP_006682.2<br>NM_006691.3 |
| MASP1 | Mannan-binding lectin serine protease 1 | MASP1_HUMAN | P48740 | NP_001027019.1<br>NM_001031849.2<br>NP_001870.3<br>NM_001879.5<br>NP_624302.1<br>NM_139125.3 |
| MBL2 | Mannose-binding protein C | MBL2_HUMAN | P11226 | NP_000233.1<br>NM_000242.2 |
| MCAM | Cell surface glycoprotein MUC18 | MUC18_HUMAN | P43121 | NP_006491.2<br>NM_006500.2 |
| MINPP1 | Multiple inositol polyphosphate phosphatase 1 | MINP1_HUMAN | Q9UNW1 | NP_001171588.1<br>NM_001178117.1<br>NP_001171589.1<br>NM_001178118.1<br>NP_004888.2<br>NM_004897.4 |
| MST1 | Hepatocyte growth factor-like protein | HGFL_HUMAN | P26927 | NP_066278.3<br>NM_020998.3 |

TABLE 3-continued

Therapeutic Efficacy Markers of the Invention.

| Marker Name | Protein Description | UNIPROT_ID | UNIPROT ACCESSION | GENBANK ACCESSION |
|---|---|---|---|---|
| NID1 | Nidogen-1 | NID1_HUMAN | P14543 | NP_002499.2 NM_002508.2 |
| ORM1 | Alpha-1-acid glycoprotein 1 | A1AG1_HUMAN | P02763 | NP_000598.2 NM_000607.2 |
| ORM2 | Alpha-1-acid glycoprotein 2 | A1AG2_HUMAN | P19652 | NP_000599.1 NM_000608.2 |
| PCOLCE | Procollagen C-endopeptidase enhancer 1 | PCOC1_HUMAN | Q15113 | NP_002584.2 NM_002593.3 |
| PDIA3 | Protein disulfide-isomerase A3 | PDIA3_HUMAN | P30101 | NP_005304.3 NM_005313.4 |
| PDIA6 | Protein disulfide-isomerase A6 | PDIA6_HUMAN | Q15084 | NP_005733.1 NM_005742.2 |
| PDLIM1 | PDZ and LIM domain protein 1 | PDLI1_HUMAN | O00151 | NP_066272.1 NM_020992.3 |
| PEPD | Xaa-Pro dipeptidase | PEPD_HUMAN | P12955 | NP_000276.2 NM_000285.3 NP_001159528.1 NM_001166056.1 NP_001159529.1 NM_001166057.1 |
| PFN1 | Profilin-1 | PROF1_HUMAN | P07737 | NP_005013.1 NM_005022.3 |
| PGLYRP2 | N-acetylmuramoyl-L-alanine amidase | PGRP2_HUMAN | Q96PD5 | NP_443122.3 NM_052890.3 |
| PKM2 | Pyruvate kinase isozymes M1/M2 | KPYM_HUMAN | P14618 | NP_001193725.1 NM_001206796.1 NP_001193726.1 NM_001206797.1 NP_001193727.1 NM_001206798.1 NP_001193728.1 NM_001206799.1 NP_002645.3 NM_002654.4 NP_872270.1 NM_182470.2 NP_872271.1 NM_182471.2 |
| PLEK | Pleckstrin | PLEK_HUMAN | P08567 | NP_002655.2 NM_002664.2 |
| PPIA | Peptidyl-prolyl cis-trans isomerase A | PPIA_HUMAN | P62937 | NP_066953.1 NM_021130.3 |
| PRDX2 | Peroxiredoxin-2 | PRDX2_HUMAN | P32119 | NP_005800.3 NM_005809.4 NP_859428.1 NM_181738.1 |
| PROCR | Endothelial protein C receptor | EPCR_HUMAN | Q9UNN8 | NP_006395.2 NM_006404.3 |
| PROS1 | Vitamin K-dependent protein S | PROS_HUMAN | P07225 | NP_000304.2 NM_000313.3 |
| PROZ | Vitamin K-dependent protein Z | PROZ_HUMAN | P22891 | NP_001243063.1 NM_001256134.1 NP_003882.1 NM_003891.2 |
| QSOX1 | Sulfhydryl oxidase 1 | QSOX1_HUMAN | O00391 | NP_001004128.1 NM_001004128.2 NP_002817.2 NM_002826.4 |
| RNASE1 | Ribonuclease pancreatic | RNAS1_HUMAN | P07998 | NP_002924.1 NM_002933.4 NP_937875.1 NM_198232.2 NP_937877.1 NM_198234.2 NP_937878.1 NM_198235.2 |
| S100A9 | Protein S100-A9 | S10A9_HUMAN | P06702 | NP_002956.1 NM_002965.3 |
| SAA4 | Serum amyloid A-4 protein | SAA4_HUMAN | P35542 | NP_006503.2 NM_006512.3 |
| SELL | L-selectin | LYAM1_HUMAN | P14151 | NP_000646.2 NM_000655.4 |
| SERPINA1 | Alpha-1-antitrypsin | A1AT_HUMAN | P01009 | NP_000286.3 NM_000295.4 |

TABLE 3-continued

Therapeutic Efficacy Markers of the Invention.

| Marker Name | Protein Description | UNIPROT_ID | UNIPROT ACCESSION | GENBANK ACCESSION |
|---|---|---|---|---|
| | | | | NP_001002235.1 |
| | | | | NM_001002235.2 |
| | | | | NP_001002236.1 |
| | | | | NM_001002236.2 |
| | | | | NP_001121172.1 |
| | | | | NM_001127700.1 |
| | | | | NP_001121173.1 |
| | | | | NM_001127701.1 |
| | | | | NP_001121174.1 |
| | | | | NM_001127702.1 |
| | | | | NP_001121175.1 |
| | | | | NM_001127703.1 |
| | | | | NP_001121176.1 |
| | | | | NM_001127704.1 |
| | | | | NP_001121177.1 |
| | | | | NM_001127705.1 |
| | | | | NP_001121178.1 |
| | | | | NM_001127706.1 |
| | | | | NP_001121179.1 |
| | | | | NM_001127707.1 |
| SERPINA4 | Kallistatin | KAIN_HUMAN | P29622 | NP_006206.2 |
| | | | | NM_006215.2 |
| SERPINA6 | Corticosteroid-binding globulin | CBG_HUMAN | P08185 | NP_001747.2 |
| | | | | NM_001756.3 |
| SERPINA7 | Thyroxine-binding globulin | THBG_HUMAN | P05543 | NP_000345.2 |
| | | | | NM_000354.5 |
| SERPIND1 | Heparin cofactor 2 | HEP2_HUMAN | P05546 | NP_000176.2 |
| | | | | NM_000185.3 |
| SLC3A2 | 4F2 cell-surface antigen heavy chain | 4F2_HUMAN | P08195 | NP_001012680.1 |
| | | | | NM_001012662.2 |
| | | | | NP_001012682.1 |
| | | | | NM_001012664.2 |
| | | | | NP_001013269.1 |
| | | | | NM_001013251.2 |
| | | | | NP_002385.3 |
| | | | | NM_002394.5 |
| SNCA | Alpha-synuclein | SYUA_HUMAN | P37840 | NP_000336.1 |
| | | | | NM_000345.3 |
| | | | | NP_001139526.1 |
| | | | | NM_001146054.1 |
| | | | | NP_001139527.1 |
| | | | | NM_001146055.1 |
| | | | | NP_009292.1 |
| | | | | NM_007308.2 |
| SOD3 | Extracellular superoxide dismutase [Cu—Zn] | SODE_HUMAN | P08294 | NP_003093.2 |
| | | | | NM_003102.2 |
| SPP2 | Secreted phosphoprotein 24 | SPP24_HUMAN | Q13103 | NP_008875.1 |
| | | | | NM_006944.2 |
| TAGLN2 | Transgelin-2 | TAGL2_HUMAN | P37802 | NP_003555.1 |
| | | | | NM_003564.1 |
| TF | Serotransferrin | TRFE_HUMAN | P02787 | NP_001054.1 |
| | | | | NM_001063.3 |
| THBS1 | Thrombospondin-1 | TSP1_HUMAN | P07996 | NP_003237.2 |
| | | | | NM_003246.2 |
| TLN1 | Talin-1 | TLN1_HUMAN | Q9Y490 | NP_006280.3 |
| | | | | NM_006289.3 |
| TNC | Tenascin | TENA_HUMAN | P24821 | NP_002151.2 |
| | | | | NM_002160.3 |
| TNXB | Tenascin-X | TENX_HUMAN | P22105 | NP_061978.6 |
| | | | | NM_019105.6 |
| | | | | NP_115859.2 |
| | | | | NM_032470.3 |
| TPM1 | Tropomyosin alpha-1 chain | TPM1_HUMAN | P09493 | NP_000357.3 |
| | | | | NM_000366.5 |
| | | | | NP_001018005.1 |
| | | | | NM_001018005.1 |
| | | | | NP_001018006.1 |
| | | | | NM_001018006.1 |
| | | | | NP_001018007.1 |
| | | | | NM_001018007.1 |
| | | | | NP_001018008.1 |
| | | | | NM_001018008.1 |
| TPM3 | Tropomyosin alpha-3 chain | TPM3_HUMAN | P06753 | NP_001036816.1 |
| | | | | NM_001043351.1 |

TABLE 3-continued

Therapeutic Efficacy Markers of the Invention.

| Marker Name | Protein Description | UNIPROT_ID | UNIPROT ACCESSION | GENBANK ACCESSION |
|---|---|---|---|---|
| | | | | NP_001036817.1 |
| | | | | NM_001043352.1 |
| | | | | NP_689476.2 |
| | | | | NM_152263.2 |
| | | | | NP_705935.1 |
| | | | | NM_153649.3 |
| TPM4 | Tropomyosin alpha-4 chain | TPM4_HUMAN | P67936 | NP_001138632.1 |
| | | | | NM_001145160.1 |
| | | | | NP_003281.1 |
| | | | | NM_003290.2 |
| TTR | Transthyretin | TTHY_HUMAN | P02766 | NP_000362.1- |
| | | | | NM_000371.3 |
| VCAM1 | Vascular cell adhesion protein 1 | VCAM1_HUMAN | P19320 | NP_001069.1 |
| | | | | NM_001078.3 |
| | | | | NP_001186763.1 |
| | | | | NM_001199834.1 |
| | | | | NP_542413.1 |
| | | | | NM_080682.2 |
| VCL | Vinculin | VINC_HUMAN | P18206 | NP_003364.1 |
| | | | | NM_003373.3 |
| | | | | NP_054706.1 |
| | | | | NM_014000.2 |
| VWF | von Willebrand factor | VWF_HUMAN | P04275 | NP_000543.2 |
| | | | | NM_000552.3 |
| YWHAZ | 14-3-3 protein zeta/delta | 1433Z_HUMAN | P63104 | NP_001129171.1 |
| | | | | NM_001135699.1 |
| | | | | NP_001129172.1 |
| | | | | NM_001135700.1 |
| | | | | NP_001129173.1 |
| | | | | NM_001135701.1 |
| | | | | NP_001129174.1 |
| | | | | NM_001135702.1 |
| | | | | NP_003397.1 |
| | | | | NM_003406.3 |
| | | | | NP_663723.1 |
| | | | | NM_145690.2 |
| FGG | Fibrinogen gamma chain | FIBG_HUMAN | P02679 | NP_000500.2 |
| | | | | NM_000509.4 |
| | | | | NP_068656.2 |
| | | | | NM_021870.2 |
| NEO1 | Neogenin | NEO1_HUMAN | Q92859 | NP_001166094.1 |
| | | | | NM_001172623.1 |
| | | | | NP_002490.2 |
| | | | | NM_002499.3 |
| FAM20C | Extracellular serine/threonine protein kinase Fam20C | DMP4_HUMAN | Q8IXL6 | NP_064608.2 |
| | | | | NM_020223.3 |
| NCAM1 | Neural cell adhesion molecule 1 | NCAM1_HUMAN | P13591 | NP_000606.3 |
| | | | | NM_000615.6 |
| | | | | NP_001070150.1 |
| | | | | NM_001076682.3 |
| | | | | NP_001229537.1 |
| | | | | NM_001242608.1 |
| | | | | NP_851996.2 |
| | | | | NM_181351.4 |
| PTPRJ | Receptor-type tyrosine-protein phosphatase eta | PTPRJ_HUMAN | Q12913 | NP_001091973.1 |
| | | | | NM_001098503.1 |
| | | | | NP_002834.3 |
| | | | | NM_002843.3 |

In certain aspects of the invention, a single marker (e.g., any one of the markers listed in Tables 1-3) may be used in the methods and compositions of the invention. For example, in one embodiment, the marker for use in the methods and compositions of the invention is USP9X. In one embodiment, the marker is SEPT3. In one embodiment, the marker is DAG1. In one embodiment, the marker is PTPRJ. In one embodiment, the marker is CPM. In one embodiment, the marker is SERPINB13. In one embodiment, the marker is LDLR. In one embodiment, the marker is MMP7. In one embodiment, the marker is BTC. In one embodiment, the marker is PPY. In one embodiment, the marker is INS.

In some embodiments, the methods may further comprise determining the level of a marker selected from the group consisting of the markers listed in Table 1-3. In other embodiments, the methods may further comprise determining the level of a marker selected from the group consisting of CSTF3, NELL1, SLIT3, LAMTOR2, MGAT4B, TMPRSS11F, ATAD3B, PTPRN, WNT9B, FUT6, B4GALT1, FAM20C, CNTN1, MGAT1, STX1A, NMU, CD59, CASR, and CPE.

In other aspects of the invention, more than one marker, e.g., a plurality of markers, e.g., two, three, four, five, six, seven, eight, nine, ten, eleven, or more markers, may be used in the methods and compositions of the invention. For example, in one embodiment, the markers for use in the methods and compositions of the invention include USP9X and SEPT3. In one embodiment, the markers include USP9X and INS. In one embodiment, the markers include SEPT3 and INS. In one embodiment, the markers include, SERPINB13 and INS. In one embodiment, the markers include PPY and DAG1. In one embodiment, the markers include PPY and BTC. In one embodiment, the markers include USP9X, SEPT3, and DAG1. In one embodiment, the markers include USP9X, SEPT3, and PTPRJ. In one embodiment, the markers include USP9X, SEPT3, and CPM. In one embodiment, the markers include USP9X, SEPT3, and SERPINB13. In one embodiment, the markers include USP9X, SEPT3, and LDLR. In one embodiment, the markers include USP9X, SEPT3, and MMP7. In one embodiment, the markers include USP9X, SEPT3, and BTC. In one embodiment, the markers include USP9X, SEPT3, and PPY. In one embodiment, the markers include USP9X, SEPT3, and INS. In one embodiment, the markers include BTC, MMP7, and PPY. In one embodiment, the markers include PPY, SEPT3, and PTPRJ. In one embodiment, the markers include CPM, INS, MMP7, and LDLR.

In some embodiments, the methods may further comprise determining the level of a marker selected from the group consisting of the markers listed in Table 1-3. In other embodiments, the methods may further comprise determining the level of a marker selected from the group consisting of CSTF3, NELL1, SLIT3, LAMTOR2, MGAT4B, TMPRSS11F, ATAD3B, PTPRN, WNT9B, FUT6, B4GALT1, FAM20C, CNTN1, MGAT1, STX1A, NMU, CD59, CASR, and CPE. For example, in one embodiment, the markers for use in the methods and compositions of the invention include USP9X, SEPT3, and CSTF3. In one embodiment, the markers include USP9X, SEPT3, and NELL1. In one embodiment, the markers include USP9X, SEPT3, and SLIT3. In one embodiment, the markers include USP9X, SEPT3, and LAMTOR2. In one embodiment, the markers include USP9X, SEPT3, and MGAT4B. In one embodiment, the markers include USP9X, SEPT3, and TMPRSS11F. In one embodiment, the markers include USP9X, SEPT3, and, ATAD3B. In one embodiment, the markers include USP9X, SEPT3, and PTPRN. In one embodiment, the markers include USP9X, SEPT3, and WNT9B. In one embodiment, the markers include USP9X, SEPT3, and FUT6. In one embodiment, the markers include USP9X, SEPT3, and B4GALT1. In one embodiment, the markers include USP9X, SEPT3, and FAM20C. In one embodiment, the markers include USP9X, SEPT3, and CNTN1. In one embodiment, the markers include USP9X, SEPT3, and MGAT1. In one embodiment, the markers include USP9X, SEPT3, and STX1A. In one embodiment, the markers include USP9X, SEPT3, and NMU. In one embodiment, the markers include USP9X, SEPT3, and CD59. In one embodiment, the markers include USP9X, SEPT3, and CASR. In one embodiment, the markers include USP9X, SEPT3, and CPE. In one embodiment, the markers include USP9X, INS, and CSTF3. In one embodiment, the markers include USP9X, INS, and NELL1. In one embodiment, the markers include USP9X, INS, and SLIT3. In one embodiment, the markers include USP9X, INS, and LAMTOR2. In one embodiment, the markers include USP9X, INS, and MGAT4B. In one embodiment, the markers include USP9X, INS, and TMPRSS11F. In one embodiment, the markers include USP9X, INS, and, ATAD3B. In one embodiment, the markers include USP9X, INS, and PTPRN. In one embodiment, the markers include USP9X, INS, and WNT9B. In one embodiment, the markers include USP9X, INS, and FUT6. In one embodiment, the markers include USP9X, INS, and B4GALT1. In one embodiment, the markers include USP9X, INS, and FAM20C. In one embodiment, the markers include USP9X, INS, and CNTN1. In one embodiment, the markers include USP9X, INS, and MGAT1. In one embodiment, the markers include USP9X, INS, and STX1A. In one embodiment, the markers include USP9X, INS, and NMU. In one embodiment, the markers include USP9X, INS, and CD59. In one embodiment, the markers include USP9X, INS, and CASR. In one embodiment, the markers include USP9X, INS, and CPE. In one embodiment, the markers include SEPT3, INS, and CSTF3. In one embodiment, the markers include SEPT3, INS, and NELL1. In one embodiment, the markers include SEPT3, INS, and SLIT3. In one embodiment, the markers include SEPT3, INS, and LAMTOR2. In one embodiment, the markers include SEPT3, INS, and MGAT4B. In one embodiment, the markers include SEPT3, INS, and TMPRSS11F. In one embodiment, the markers include SEPT3, INS, and, ATAD3B. In one embodiment, the markers include SEPT3, INS, and PTPRN. In one embodiment, the markers include SEPT3, INS, and WNT9B. In one embodiment, the markers include SEPT3, INS, and FUT6. In one embodiment, the markers include SEPT3, INS, and B4GALT1. In one embodiment, the markers include SEPT3, INS, and FAM20C. In one embodiment, the markers include SEPT3, INS, and CNTN1. In one embodiment, the markers include SEPT3, INS, and MGAT1. In one embodiment, the markers include SEPT3, INS, and STX1A. In one embodiment, the markers include SEPT3, INS, and NMU. In one embodiment, the markers include SEPT3, INS, and CD59. In one embodiment, the markers include SEPT3, INS, and CASR. In one embodiment, the markers include SEPT3, INS, and CPE. In one embodiment, the markers include SERPINB13, INS, and CSTF3. In one embodiment, the markers include SERPINB13, INS, and NELL1. In one embodiment, the markers include SERPINB13, INS, and SLIT3. In one embodiment, the markers include SERPINB13, INS, and LAMTOR2. In one embodiment, the markers include SERPINB13, INS, and MGAT4B. In one embodiment, the markers include SERPINB13, INS, and TMPRSS11F. In one embodiment, the markers include SERPINB13, INS, and, ATAD3B. In one embodiment, the markers include SERPINB13, INS, and PTPRN. In one embodiment, the markers include SERPINB13, INS, and WNT9B. In one embodiment, the markers include SERPINB13, INS, and FUT6. In one embodiment, the markers include SERPINB13, INS, and B4GALT1. In one embodiment, the markers include SERPINB13, INS, and FAM20C. In one embodiment, the markers include SERPINB13, INS, and CNTN1. In one embodiment, the markers include SERPINB13, INS, and MGAT1. In one embodiment, the markers include SERPINB13, INS, and STX1A. In one embodiment, the markers include SERPINB13, INS, and NMU. In one embodiment, the markers include SERPINB13, INS, and CD59. In one embodiment, the markers include SERPINB13, INS, and CASR. In one embodiment, the markers include SERPINB13, INS, and CPE. In one embodiment, the markers include PPY, DAG1, and CSTF3. In one embodiment, the markers include PPY, DAG1, and NELL1. In one embodiment, the markers include PPY, DAG1, and SLIT3. In one embodiment, the markers include PPY, DAG1, and LAMTOR2. In one embodiment, the markers include PPY, DAG1, and MGAT4B. In one embodiment, the markers include PPY, DAG1, and TMPRSS11F. In one embodiment, the markers include PPY, DAG1, and, ATAD3B. In one embodiment, the markers include PPY, DAG1, and PTPRN. In one embodiment, the markers include PPY, DAG1, and WNT9B. In one embodiment, the markers include PPY, DAG1, and FUT6. In one embodiment, the markers include PPY, DAG1, and B4GALT1. In one embodiment, the markers include PPY, DAG1, and FAM20C. In one embodiment, the markers include PPY, DAG1, and CNTN1. In one embodiment, the markers include PPY, DAG1, and MGAT1. In one embodiment, the markers include PPY, DAG1, and STX1A. In one embodiment, the markers include PPY, DAG1, and NMU. In one embodiment, the markers include PPY, DAG1, and CD59. In one embodiment, the markers include PPY, DAG1, and CASR. In one embodiment, the markers include PPY, DAG1, and CPE. In one embodiment, the markers include PPY, BTC, and CSTF3. In one embodiment, the markers include PPY, BTC, and NELL1. In one embodiment, the markers include PPY, BTC, and SLIT3. In one embodiment, the markers include PPY, BTC, and LAMTOR2. In one embodiment, the markers include PPY, BTC, and MGAT4B. In one embodiment, the markers include PPY, BTC, and TMPRSS11F. In one embodiment, the markers include PPY, BTC, and, ATAD3B. In one embodiment, the markers include PPY, BTC, and PTPRN. In one embodiment, the markers include PPY, BTC, and WNT9B. In one embodiment, the markers include PPY, BTC, and FUT6. In one embodiment, the markers include PPY, BTC, and B4GALT1. In one embodiment, the markers include PPY, BTC, and FAM20C. In one embodiment, the markers include PPY, BTC, and CNTN1. In one embodiment, the markers include PPY, BTC, and MGAT1. In one embodiment, the markers include PPY, BTC, and STX1A. In one embodiment, the markers include PPY, BTC, and NMU. In one embodiment, the markers include PPY, BTC, and CD59. In one embodiment, the markers include PPY, BTC, and CASR. In one embodiment, the markers include PPY, BTC, and CPE. In one embodiment, the markers include USP9X, SEPT3, DAG1, and CSTF3. In one embodiment, the markers include USP9X, SEPT3, DAG1, and NELL1. In one embodiment, the markers include USP9X, SEPT3, DAG1, and SLIT3. In one embodiment, the markers include USP9X, SEPT3, DAG1, and LAMTOR2. In one embodiment, the markers include USP9X, SEPT3, DAG1, and MGAT4B. In one embodiment, the markers include USP9X, SEPT3, DAG1, and TMPRSS11F. In one embodiment, the markers include USP9X, SEPT3, DAG1, and, ATAD3B. In one embodiment, the markers include USP9X, SEPT3, DAG1, and PTPRN. In one embodiment, the markers include USP9X, SEPT3, DAG1, and WNT9B. In one embodiment, the markers include USP9X, SEPT3, DAG1, and FUT6. In one embodiment, the markers include USP9X, SEPT3, DAG1, and B4GALT1. In one embodiment, the markers include USP9X, SEPT3, DAG1, and FAM20C. In one embodiment, the markers include USP9X, SEPT3, DAG1, and CNTN1. In one embodiment, the markers include USP9X, SEPT3, DAG1, and MGAT1. In one embodiment, the markers include USP9X, SEPT3, DAG1, and STX1A. In one embodiment, the markers include USP9X, SEPT3, DAG1, and NMU. In one embodiment, the markers include USP9X, SEPT3, DAG1, and CD59. In one embodiment, the markers include USP9X, SEPT3, DAG1, and CASR. In one embodiment, the markers include USP9X, SEPT3, DAG1, and CPE. In one embodiment, the markers include USP9X, SEPT3, PTPRJ, and CSTF3. In one embodiment, the markers include USP9X, SEPT3, PTPRJ, and NELL1. In one embodiment, the markers include USP9X, SEPT3, PTPRJ, and SLIT3. In one embodiment, the markers include USP9X, SEPT3, PTPRJ, and LAMTOR2. In one embodiment, the markers include USP9X, SEPT3, PTPRJ, and MGAT4B. In one embodiment, the markers include USP9X, SEPT3, PTPRJ, and TMPRSS11F. In one embodiment, the markers include USP9X, SEPT3, PTPRJ, and, ATAD3B. In one embodiment, the markers include USP9X, SEPT3, PTPRJ, and PTPRN. In one embodiment, the markers include USP9X, SEPT3, PTPRJ, and WNT9B. In one embodiment, the markers include USP9X, SEPT3, PTPRJ, and FUT6. In one embodiment, the markers include USP9X, SEPT3, PTPRJ, and B4GALT1. In one embodiment, the markers include USP9X, SEPT3, PTPRJ, and FAM20C. In one embodiment, the markers include USP9X, SEPT3, PTPRJ, and CNTN1. In one embodiment, the markers include USP9X, SEPT3, PTPRJ, and MGAT1. In one embodiment, the markers include USP9X, SEPT3, PTPRJ, and STX1A. In one embodiment, the markers include USP9X, SEPT3, PTPRJ, and NMU. In one embodiment, the markers include USP9X, SEPT3, PTPRJ, and CD59. In one embodiment, the markers include USP9X, SEPT3, PTPRJ, and CASR. In one embodiment, the markers include USP9X, SEPT3, PTPRJ, and CPE. In one embodiment, the markers include USP9X, SEPT3, CPM, and CSTF3. In one embodiment, the markers include USP9X, SEPT3, CPM, and NELL1. In one embodiment, the markers include USP9X, SEPT3, CPM, and SLIT3. In one embodiment, the markers include USP9X, SEPT3, CPM, and LAMTOR2. In one embodiment, the markers include USP9X, SEPT3, CPM, and MGAT4B. In one embodiment, the markers include USP9X, SEPT3, CPM, and TMPRSS11F. In one embodiment, the markers include USP9X, SEPT3, CPM, and, ATAD3B. In one embodiment, the markers include USP9X, SEPT3, CPM, and PTPRN. In one embodiment, the markers include USP9X, SEPT3, CPM, and WNT9B. In one embodiment, the markers include USP9X, SEPT3, CPM, and FUT6. In one embodiment, the markers include USP9X, SEPT3, CPM, and B4GALT1. In one embodiment, the markers include USP9X, SEPT3, CPM, and FAM20C. In one embodiment, the markers include USP9X, SEPT3, CPM, and CNTN1. In one embodiment, the markers include USP9X, SEPT3, CPM, and MGAT1. In one embodiment, the markers include USP9X, SEPT3, CPM, and STX1A. In one embodiment, the markers include USP9X, SEPT3, CPM, and NMU. In one embodiment, the markers include USP9X, SEPT3, CPM, and CD59. In one embodiment, the markers include USP9X, SEPT3, CPM, and CASR. In one embodiment, the markers include USP9X, SEPT3, CPM, and CPE. In one embodiment, the markers include USP9X, SEPT3, SERPINB13, and CSTF3. In one embodiment, the markers include USP9X, SEPT3, SERPINB13, and NELL1. In one embodiment, the markers include USP9X, SEPT3, SERPINB13, and SLIT3. In one embodiment, the markers include USP9X, SEPT3, SERPINB13, and LAMTOR2. In one embodiment, the markers include USP9X, SEPT3, SERPINB13, and MGAT4B. In one embodiment, the markers include USP9X, SEPT3, SERPINB13, and TMPRSS11F. In one embodiment, the markers include USP9X, SEPT3, SERPINB13, and, ATAD3B. In one embodiment, the markers include USP9X, SEPT3, SERPINB13, and PTPRN. In one embodiment, the markers include USP9X, SEPT3, SERPINB13, and WNT9B. In one embodiment, the markers include USP9X, SEPT3, SERPINB13, and FUT6. In one embodiment, the markers include USP9X, SEPT3, SERPINB13, and B4GALT1. In one embodiment, the markers include USP9X, SEPT3, SERPINB13, and FAM20C. In one embodiment, the markers include USP9X, SEPT3, SERPINB13, and CNTN1. In one embodiment, the markers include USP9X, SEPT3, SERPINB13, and MGAT1. In one embodiment, the markers include USP9X, SEPT3, SERPINB13, and STX1A. In one embodiment, the markers include USP9X, SEPT3, SERPINB13, and NMU. In one embodiment, the markers include USP9X, SEPT3, SERPINB13, and CD59. In one embodiment, the markers include USP9X, SEPT3, SERPINB13, and CASR. In one embodiment, the markers include USP9X, SEPT3, SERPINB13, and CPE. In one embodiment, the markers include USP9X, SEPT3, LDLR, and CSTF3. In one embodiment, the markers include USP9X, SEPT3, LDLR, and NELL1. In one embodiment, the markers include USP9X, SEPT3, LDLR, and SLIT3. In one embodiment, the markers include USP9X, SEPT3, LDLR, and LAMTOR2. In one embodiment, the markers include USP9X, SEPT3, LDLR, and MGAT4B. In one embodiment, the markers include USP9X, SEPT3, LDLR, and TMPRSS11F. In one embodiment, the markers include USP9X, SEPT3, LDLR, and, ATAD3B. In one embodiment, the markers include USP9X, SEPT3, LDLR, and PTPRN. In one embodiment, the markers include USP9X, SEPT3, LDLR, and WNT9B. In one embodiment, the markers include USP9X, SEPT3, LDLR, and FUT6. In one embodiment, the markers include USP9X, SEPT3, LDLR, and B4GALT1. In one embodiment, the markers include USP9X, SEPT3, LDLR, and FAM20C. In one embodiment, the markers include USP9X, SEPT3, LDLR, and CNTN1. In one embodiment, the markers include USP9X, SEPT3, LDLR, and MGAT1. In one embodiment, the markers include USP9X, SEPT3, LDLR, and STX1A. In one embodiment, the markers include USP9X, SEPT3, LDLR, and NMU. In one embodiment, the markers include USP9X, SEPT3, LDLR, and CD59. In one embodiment, the markers include USP9X, SEPT3, LDLR, and CASR. In one embodiment, the markers include USP9X, SEPT3, LDLR, and CPE. In one embodiment, the markers include USP9X, SEPT3, MMP7, and CSTF3. In one embodiment, the markers include USP9X, SEPT3, MMP7, and NELL1. In one embodiment, the markers include USP9X, SEPT3, MMP7, and SLIT3. In one embodiment, the markers include USP9X, SEPT3, MMP7, and LAMTOR2. In one embodiment, the markers include USP9X, SEPT3, MMP7, and MGAT4B. In one embodiment, the markers include USP9X, SEPT3, MMP7, and TMPRSS11F. In one embodiment, the markers include USP9X, SEPT3, MMP7, and, ATAD3B. In one embodiment, the markers include USP9X, SEPT3, MMP7, and PTPRN. In one embodiment, the markers include USP9X, SEPT3, MMP7, and WNT9B. In one embodiment, the markers include USP9X, SEPT3, MMP7, and FUT6. In one embodiment, the markers include USP9X, SEPT3, MMP7, and B4GALT1. In one embodiment, the markers include USP9X, SEPT3, MMP7, and FAM20C. In one embodiment, the markers include USP9X, SEPT3, MMP7, and CNTN1. In one embodiment, the markers include USP9X, SEPT3, MMP7, and MGAT1. In one embodiment, the markers include USP9X, SEPT3, MMP7, and STX1A. In one embodiment, the markers include USP9X, SEPT3, MMP7, and NMU. In one embodiment, the markers include USP9X, SEPT3, MMP7, and CD59. In one embodiment, the markers include USP9X, SEPT3, MMP7, and CASR. In one embodiment, the markers include USP9X, SEPT3, MMP7, and CPE. In one embodiment, the markers include USP9X, SEPT3, BTC, and CSTF3. In one embodiment, the markers include USP9X, SEPT3, BTC, and NELL1. In one embodiment, the markers include USP9X, SEPT3, BTC, and SLIT3. In one embodiment, the markers include USP9X, SEPT3, BTC, and LAMTOR2. In one embodiment, the markers include USP9X, SEPT3, BTC, and MGAT4B. In one embodiment, the markers include USP9X, SEPT3, BTC, and TMPRSS11F. In one embodiment, the markers include USP9X, SEPT3, BTC, and, ATAD3B. In one embodiment, the markers include USP9X, SEPT3, BTC, and PTPRN. In one embodiment, the markers include USP9X, SEPT3, BTC, and WNT9B. In one embodiment, the markers include USP9X, SEPT3, BTC, and FUT6. In one embodiment, the markers include USP9X, SEPT3, BTC, and B4GALT1. In one embodiment, the markers include USP9X, SEPT3, BTC, and FAM20C. In one embodiment, the markers include USP9X, SEPT3, BTC, and CNTN1. In one embodiment, the markers include USP9X, SEPT3, BTC, and MGAT1. In one embodiment, the markers include USP9X, SEPT3, BTC, and STX1A. In one embodiment, the markers include USP9X, SEPT3, BTC, and NMU. In one embodiment, the markers include USP9X, SEPT3, BTC, and CD59. In one embodiment, the markers include USP9X, SEPT3, BTC, and CASR. In one embodiment, the markers include USP9X, SEPT3, BTC, and CPE. In one embodiment, the markers include USP9X, SEPT3, PPY, and CSTF3. In one embodiment, the markers include USP9X, SEPT3, PPY, and NELL1. In one embodiment, the markers include USP9X, SEPT3, PPY, and SLIT3. In one embodiment, the markers include USP9X, SEPT3, PPY, and LAMTOR2. In one embodiment, the markers include USP9X, SEPT3, PPY, and MGAT4B. In one embodiment, the markers include USP9X, SEPT3, PPY, and TMPRSS11F. In one embodiment, the markers include USP9X, SEPT3, PPY, and, ATAD3B. In one embodiment, the markers include USP9X, SEPT3, PPY, and PTPRN. In one embodiment, the markers include USP9X, SEPT3, PPY, and WNT9B. In one embodiment, the markers include USP9X, SEPT3, PPY, and FUT6. In one embodiment, the markers include USP9X, SEPT3, PPY, and B4GALT1. In one embodiment, the markers include USP9X, SEPT3, PPY, and FAM20C. In one embodiment, the markers include USP9X, SEPT3, PPY, and CNTN1. In one embodiment, the markers include USP9X, SEPT3, PPY, and MGAT1. In one embodiment, the markers include USP9X, SEPT3, PPY, and STX1A. In one embodiment, the markers include USP9X, SEPT3, PPY, and NMU. In one embodiment, the markers include USP9X, SEPT3, PPY, and CD59. In one embodiment, the markers include USP9X, SEPT3, PPY, and CASR. In one embodiment, the markers include USP9X, SEPT3, PPY, and CPE. In one embodiment, the markers include USP9X, SEPT3, INS, and CSTF3. In one embodiment, the markers include USP9X, SEPT3, INS, and NELL1. In one embodiment, the markers include USP9X, SEPT3, INS, and SLIT3. In one embodiment, the markers include USP9X, SEPT3, INS, and LAMTOR2. In one embodiment, the markers include USP9X, SEPT3, INS, and MGAT4B. In one embodiment, the markers include USP9X, SEPT3, INS, and TMPRSS11F. In one embodiment, the markers include USP9X, SEPT3, INS, and, ATAD3B. In one embodiment, the markers include USP9X, SEPT3, INS, and PTPRN. In one embodiment, the markers include USP9X, SEPT3, INS, and WNT9B. In one embodiment, the markers include USP9X, SEPT3, INS, and FUT6. In one embodiment, the markers include USP9X, SEPT3, INS, and B4GALT1. In one embodiment, the markers include USP9X, SEPT3, INS, and FAM20C. In one embodiment, the markers include USP9X, SEPT3, INS, and CNTN1. In one embodiment, the markers include USP9X, SEPT3, INS, and MGAT1. In one embodiment, the markers include USP9X, SEPT3, INS, and STX1A. In one embodiment, the markers include USP9X, SEPT3, INS, and NMU. In one embodiment, the markers include USP9X, SEPT3, INS, and CD59. In one embodiment, the markers include USP9X, SEPT3, INS, and CASR. In one embodiment, the markers include USP9X, SEPT3, INS, and CPE. In one embodiment, the markers include BTC, MMP7, PPY, and CSTF3. In one embodiment, the markers include BTC, MMP7, PPY, and NELL1. In one embodiment, the markers include BTC, MMP7, PPY, and SLIT3. In one embodiment, the markers include BTC, MMP7, PPY, and LAMTOR2. In one embodiment, the markers include BTC, MMP7, PPY, and MGAT4B. In one embodiment, the markers include BTC, MMP7, PPY, and TMPRSS11F. In one embodiment, the markers include BTC, MMP7, PPY, and, ATAD3B. In one embodiment, the markers include BTC, MMP7, PPY, and PTPRN. In one embodiment, the markers include BTC, MMP7, PPY, and WNT9B. In one embodiment, the markers include BTC, MMP7, PPY, and FUT6. In one embodiment, the markers include BTC, MMP7, PPY, and B4GALT1. In one embodiment, the markers include BTC, MMP7, PPY, and FAM20C. In one embodiment, the markers include BTC, MMP7, PPY, and CNTN1. In one embodiment, the markers include BTC, MMP7, PPY, and MGAT1. In one embodiment, the markers include BTC, MMP7, PPY, and STX1A. In one embodiment, the markers include BTC, MMP7, PPY, and NMU. In one embodiment, the markers include BTC, MMP7, PPY, and CD59. In one embodiment, the markers include BTC, MMP7, PPY, and CASR. In one embodiment, the markers include BTC, MMP7, PPY, and CPE. In one embodiment, the markers include PPY, SEPT3, PTPRJ, and CSTF3. In one embodiment, the markers include PPY, SEPT3, PTPRJ, and NELL1. In one embodiment, the markers include PPY, SEPT3, PTPRJ, and SLIT3. In one embodiment, the markers include PPY, SEPT3, PTPRJ, and LAMTOR2. In one embodiment, the markers include PPY, SEPT3, PTPRJ, and MGAT4B. In one embodiment, the markers include PPY, SEPT3, PTPRJ, and TMPRSS11F. In one embodiment, the markers include PPY, SEPT3, PTPRJ, and, ATAD3B. In one embodiment, the markers include PPY, SEPT3, PTPRJ, and PTPRN. In one embodiment, the markers include PPY, SEPT3, PTPRJ, and WNT9B. In one embodiment, the markers include PPY, SEPT3, PTPRJ, and FUT6. In one embodiment, the markers include PPY, SEPT3, PTPRJ, and B4GALT1. In one embodiment, the markers include PPY, SEPT3, PTPRJ, and FAM20C. In one embodiment, the markers include PPY, SEPT3, PTPRJ, and CNTN1. In one embodiment, the markers include PPY, SEPT3, PTPRJ, and MGAT1. In one embodiment, the markers include PPY, SEPT3, PTPRJ, and STX1A. In one embodiment, the markers include PPY, SEPT3, PTPRJ, and NMU. In one embodiment, the markers include PPY, SEPT3, PTPRJ, and CD59. In one embodiment, the markers include PPY, SEPT3, PTPRJ, and CASR. In one embodiment, the markers include PPY, SEPT3, PTPRJ, and CPE. In one embodiment, the markers include CPM, INS, MMP7, LDLR, and CSTF3. In one embodiment, the markers include CPM, INS, MMP7, LDLR, and NELL1. In one embodiment, the markers include CPM, INS, MMP7, LDLR, and SLIT3. In one embodiment, the markers include CPM, INS, MMP7, LDLR, and LAMTOR2. In one embodiment, the markers include CPM, INS, MMP7, LDLR, and MGAT4B. In one embodiment, the markers include CPM, INS, MMP7, LDLR, and TMPRSS11F. In one embodiment, the markers include CPM, INS, MMP7, LDLR, and, ATAD3B. In one embodiment, the markers include CPM, INS, MMP7, LDLR, and PTPRN. In one embodiment, the markers include CPM, INS, MMP7, LDLR, and WNT9B. In one embodiment, the markers include CPM, INS, MMP7, LDLR, and FUT6. In one embodiment, the markers include CPM, INS, MMP7, LDLR, and B4GALT1. In one embodiment, the markers include CPM, INS, MMP7, LDLR, and FAM20C. In one embodiment, the markers include CPM, INS, MMP7, LDLR, and CNTN1. In one embodiment, the markers include CPM, INS, MMP7, LDLR, and MGAT1. In one embodiment, the markers include CPM, INS, MMP7, LDLR, and STX1A. In one embodiment, the markers include CPM, INS, MMP7, LDLR, and NMU. In one embodiment, the markers include CPM, INS, MMP7, LDLR, and CD59. In one embodiment, the markers include CPM, INS, MMP7, LDLR, and CASR. In one embodiment, the markers include CPM, INS, MMP7, LDLR, and CPE.

II. Methods of the Invention

A. Diagnostic and Prognostic Methods

In certain aspects, the present invention provides diagnostic methods. For example, in one aspect, the present invention provides methods for determining whether a subject has impaired glucose tolerance. The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject has impaired glucose tolerance. In another aspect, the present invention provides methods for determining whether a subject has type 2 diabetes. The methods include determining the level of one or more markers of the invention in a sample(s) from the subject with a level of the one or more markers in a control sample(s). A difference in the level (e.g., higher or lower) of one or more markers in the sample(s) from the subject as compared to the level of the one or more markers in the control sample indicates that the subject has type 2 diabetes.

The present invention also provides prognostic methods. For example, in one aspect, the present invention provides methods for determining whether a subject will develop impaired glucose tolerance. The methods include determining the level of one or more markers of the invention in a sample(s) from the subject with a level of the one or more markers in a control sample(s). A difference in the level (e.g., higher or lower) of one or more markers in the sample(s) from the subject as compared to the level of the one or more markers in the control sample indicates that the subject will develop impaired glucose tolerance.

In another aspect, the present invention provides methods for determining whether a subject will develop type 2 diabetes. The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject will develop type 2 diabetes. Numerous complications have been associated with impaired glucose tolerance and/or type 2 diabetes, especially prolonged impaired glucose tolerance and/or type 2 diabetes. For example, such subjects have a two to four times the risk of cardiovascular disease, including ischemic heart disease and stroke, a 20-fold increase in lower limb amputations, and increased rates of hospitalizations. Type 2 diabetes is also the largest cause of non-traumatic blindness and nephropathy including kidney failure and has been associated with an increased risk of cognitive dysfunction and dementia through disease processes such as Alzheimer's disease and vascular dementia. Other complications include, for example, neuropathy, acanthosis nigricans, sexual dysfunction, and frequent infections.

As the markers of the present invention have been shown to be differentially expressed in subjects newly diagnosed with type 2 diabetes and those having established type 2 diabetes, e.g., those subjects having prolonged impaired glucose tolerance and/or type 2 diabetes, the present invention also provides methods for determining whether a subject will develop a type 2 diabetes-associated complication. The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject will respond to a diabetic therapy.

In another aspect the present invention provides methods for determining whether a subject having impaired glucose tolerance and/or type 2 diabetes will respond to a treatment regime. The methods include determining the level of one or more markers of the invention in a sample(s) from the subject with a level of the one or more markers in a control sample(s). A difference in the level (e.g., higher or lower) of the one or more markers in the sample(s) from the subject as compared to the level of the one or more markers in the control sample indicates that the subject will respond to a treatment.

Numerous diabetic therapies are known in the art and include, for example, insulin sensitizers, such as biguanides (e.g., metformin) and thiazolidinediones (e.g., rosiglitazone, pioglitazone, troglitazone); secretagogues, such as the sulfonylureas (e.g., glyburide, glipizide, glimepiride, tolbutamide, acetohexamide, tolazamide, chlorpropamide, gliclazide, glycopyamide, gliquidone), the nonsulfonylurea secretagogues, e.g., meglitinide derivatives (e.g., repaglinide, nateglinide); the dipeptidyl peptidase IV inhibitors (e.g., sitagliptin, saxagliptin, linagliptin, vildagliptin, allogliptin, septagliptin); alpha-glucosidase inhibitors (e.g., acarbose, miglitol, voglibose); amylinomimetics (e.g., pramlintide acetate); incretin mimetics (e.g., exenatide, liraglutide, taspoglutide); insulin and its analogues (e.g., rapid acting, slow acting, and intermediate acting); bile acid sequestrants (e.g., colesevelam); and dopamine agonists (e.g., bromocriptine), alone or in combinations.

In certain embodiments of the invention, the treatment comprises an insulin sensitizer. In another embodiment, the treatment comprises an insulin sensitizer and a secretagogue. In yet another embodiment, the treatment comprises an insulin sensitizer, a secretagogue, and insulin.

The methods of the present invention can be practiced in conjunction with any other method(s) used by the skilled practitioner to diagnose, prognose, and/or monitor impaired glucose tolerance and/or type 2 diabetes in a subject and/or a type 2 diabetes complication and/or response to trreatment. For example, the methods of the invention may be performed in conjunction with any clinical measurement of glucose tolerance, obesity, and/or diabetes known in the art including serological, cytological and/or detection (and quantification, if appropriate) of other molecular markers.

In any of the methods (and kits) of the invention, the level of a marker(s) of the invention in a sample obtained from a subject may be determined by any of a wide variety of well-known techniques and methods, which transform a marker of the invention within the sample into a moiety that can be detected and quantified. Non-limiting examples of such methods include analyzing the sample using immunological methods for detection of proteins, protein purification methods, protein function or activity assays, nucleic acid hybridization methods, nucleic acid reverse transcription methods, and nucleic acid amplification methods, immunoblotting, Western blotting, Northern blotting, electron microscopy, mass spectrometry, e.g., MALDI-TOF and SELDI-TOF, immunoprecipitations, immunofluorescence, immunohistochemistry, enzyme linked immunosorbent assays (ELISAs), e.g., amplified ELISA, quantitative blood based assays, e.g., serum ELISA, quantitative urine based assays, flow cytometry, Southern hybridizations, array analysis, and the like, and combinations or sub-combinations thereof.

For example, an mRNA sample may be obtained from the sample from the subject (e.g., bronchial lavage, mouth swab, biopsy, or peripheral blood mononuclear cells, by standard methods) and expression of mRNA(s) encoding a marker of the invention in the sample may be detected and/or determined using standard molecular biology techniques, such as PCR analysis. A preferred method of PCR analysis is reverse transcriptase-polymerase chain reaction (RT-PCR). Other suitable systems for mRNA sample analysis include microarray analysis (e.g., using Affymetrix's microarray system or Illumina's BeadArray Technology).

It will be readily understood by the ordinarily skilled artisan that essentially any technical means established in the art for detecting the level a marker of the invention at either the nucleic acid or protein level, can be used to determine the level a marker of the invention as discussed herein.

In one embodiment, the level of a marker of the invention in a sample is determined by detecting a transcribed polynucleotide, or portion thereof, e.g., mRNA, or cDNA, of a marker of the invention gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis.

In one embodiment, the level of a marker of the invention is determined using a nucleic acid probe. The term "probe", as used herein, refers to any molecule that is capable of selectively binding to a specific marker of the invention. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to a marker mRNA. The nucleic acid probe can be, for example, a full-length cDNA, or a portion thereof, such as an oligonucleotide of at least about 7, 10, 15, 20, 25, 30, 35, 40, 45, 50, 100, 250 or about 500 nucleotides in length and sufficient to specifically hybridize under stringent conditions to marker genomic DNA.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of a marker of the invention mRNA.

An alternative method for determining the level of a marker of the invention in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self-sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of a marker of the invention is determined by quantitative fluorogenic RT-PCR (i.e., the TaqMan™ System). Such methods typically utilize pairs of oligonucleotide primers that are specific for a marker of the invention. Methods for designing oligonucleotide primers specific for a known sequence are well known in the art.

The level of a marker of the invention mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of a level of a marker of the invention may also comprise using nucleic acid probes in solution.

In one embodiment of the invention, microarrays are used to detect the level of a marker of the invention. Microarrays are particularly well suited for this purpose because of the reproducibility between different experiments. DNA microarrays provide one method for the simultaneous measurement of the levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, e.g., U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

In certain situations it may be possible to assay for the level of a marker of the invention at the protein level, using a detection reagent that detects the protein product encoded by the mRNA of a marker of the invention. For example, if an antibody reagent is available that binds specifically to a marker of the invention protein product to be detected, and not to other proteins, then such an antibody reagent can be used to detect the expression of a marker of the invention in a cellular sample from the subject, or a preparation derived from the cellular sample, using standard antibody-based techniques known in the art, such as FACS analysis, and the like.

Other known methods for detecting a marker of the invention at the protein level include methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, and Western blotting.

Proteins from samples can be isolated using techniques that are well known to those of skill in the art. The protein isolation methods employed can, for example, be those described in Harlow and Lane (Harlow and Lane, 1988, Antibodies: A Laboratory Manual, Cold Spring Harbor Laboratory Press, Cold Spring Harbor, N.Y.).

In one embodiment, antibodies, or antibody fragments, are used in methods such as Western blots or immunofluorescence techniques to detect the expressed proteins. Antibodies for determining the expression of a marker of the invention are commercially available and one of ordinary skill in the art can readily identify appropriate antibodies for use in the methods of the invention. Exemplary commercially available antibodies suitable for use in the claimed methods for determining the level of a marker of the invention are listed in the table below (Table 4).

TABLE 4

Commercially Available Antibodies

| Marker Name | Company Name | Catalog Number |
| --- | --- | --- |
| USP9X | Fitzgerald Industries International | 70R-9746 |
| | Abnova Corporation | H00008239-A01 |
| | LifeSpan BioSciences | LS-C143435 |
| | Bethyl Laboratories | A301-350A |
| | Abgent | AT4497a |
| DAG1 | antibodies-online | ABIN502745 |
| | GeneTex | GTX88089 |
| | Abnova Corporation | H00001605-M01 |
| | ProSci, Inc | 48-780 |
| | Proteintech Group Inc | 11017-1-AP |
| SEPT3 | Atlas Antibodies | HPA003548 |
| | LifeSpan BioSciences | LS-C120158 |
| | Sigma-Aldrich | HPA003548-100UL |
| | Abgent | AT3814a |
| | USCN Life Science, Inc. | E95863Hu |
| PTPRJ | GeneTex | GTX82145 |
| | Thermo Scientific Pierce Antibodies | PA1-27625 |
| | Abnova Corporation | H00005795-B01P |
| | LifeSpan BioSciences | LS-C40932 |
| | Novus Biologicals | H00005795-M01 |
| CPM | MyBioSource.com | MBS855861 |
| | Santa Cruz Biotechnology, Inc. | sc-98698 |
| | Abnova Corporation | H00001368-B01P |
| | Biorbyt | orb125616 |
| | USCN Life Science, Inc. | E92397Hu |

TABLE 4-continued

Commercially Available Antibodies

| Marker Name | Company Name | Catalog Number |
|---|---|---|
| SERPINB13 | Fitzgerald Industries International | 10R-5733 |
| | Proteintech Group Inc | 18045-1-AP |
| | Novus Biologicals | NBP2-01336 |
| | Sigma-Aldrich | SAB2104770-50UG |
| | Abnova Corporation | PAB1049 |
| LDLR | Atlas Antibodies | HPA009647 |
| | Santa Cruz Biotechnology, Inc. | sc-20744 |
| | Abgent | AP8960c |
| | Abnova Corporation | H00003949-A01 |
| | Acris Antibodies GmbH | BP5013 |
| MMP7 | GeneTex | GTX17854 |
| | GenWay Biotech, Inc. | GWB-5EF98D |
| | Abgent | AF1674a |
| | LifeSpan BioSciences | LS-C88495-20 |
| | R&D Systems | DMP700 |
| BTC | LifeSpan BioSciences | LS-C100871-100 |
| | Abgent | AP11669a |
| | Sigma-Aldrich | B2430 |
| | R&D Systems | AF-261-NA |
| | Creative Diagnostics | DEIA089 |
| PPY | Abnova Corporation | H00005539-B01 |
| | LifeSpan BioSciences | LS-C38055-200 |
| | GenWay Biotech, Inc. | GWB-C1C3DC |
| | R&D Systems | MAB6297 |
| | USCN Life Science, Inc. | E91265Hu |
| INS | Abgent | AM1985b |
| | antibodies-online | ABIN237690 |
| | GeneTex | GTX81555 |
| | Atlas Antibodies | HPA004932 |
| | EMD Millipore Corp | EZHIASF-14K |
| CSTF3 | Atlas Antibodies | HPA040168 |
| | Abnova Corporation | H00001479-A01 |
| | AbD Serotec | MCA3034Z |
| | Fitzgerald Industries International | 70R-4939 |
| | Abgent | AT1663a |
| NELL1 | GeneTex | GTX103819 |
| | Abnova Corporation | H00004745-A01 |
| | LifeSpan BioSciences | LS-C139121-100 |
| | AbD Serotec | MCA5151Z |
| | Abcam | ab55548 |
| SLIT3 | EMD Millipore | AB5703P |
| | Abnova Corporation | H00006586-A01 |
| | R&D Systems | AF3629 |
| | Sigma-Aldrich | WH0006586M4 |
| | Creative Biomart | CAB-4683MH |
| LAMTOR2 | Atlas Antibodies | HPA004126 |
| | Sigma-Aldrich | HPA004126 |
| | Cell Signaling Technology | 8145S |
| | Abgent | AP13338c |
| | Novus Biologicals | NBP1-71687 |
| MGAT4B | Abnova Corporation | H00011282-D01 |
| | Sigma-Aldrich | SAB1407130 |
| | Novus Biologicals | H00011282-B01P |
| | Creative Biomart | CPBT-40309MH |
| | Abcam | ab67394 |
| TMPRSS11F | Atlas Antibodies | HPA026911 |
| | Sigma-Aldrich | HPA026911 |
| | Abcam | ab59857 |
| | Novus Biologicals | NBP1-94000 |
| | Abnova Corporation | PAB21857 |
| ATAD3B | Abnova Corporation | H00083858-B01P |
| | Thermo Scientific Pierce Antibodies | PA5-21160 |
| | Novus Biologicals | H00083858-B01 |
| | Sigma-Aldrich | SAB1400727 |
| | Abcam | ab112563 |
| PTPRN | Atlas Antibodies | HPA007179 |
| | GeneTex | GTX82148 |
| | Thermo Scientific Pierce Antibodies | PA1-27627 |
| | Abnova Corporation | MAB2710 |
| | Novus Biologicals | H00005798-B02P |
| WNT9B | Abgent | AP16959c |
| | Aviva Systems Biology | ARP41243_T100 |
| | LifeSpan BioSciences | LS-C108128-100 |
| | Fitzgerald Industries International | 70R-7246 |
| | R&D Systems | AF3669 |
| FUT6 | Fitzgerald Industries International | 70R-5379 |
| | Abgent | AP4925c |
| | Thermo Scientific Pierce Antibodies | PA5-24850 |
| | Sigma-Aldrich | AV48467 |
| | Novus Biologicals | H00002528-B01P |
| B4GALT1 | Atlas Antibodies | HPA010806 |
| | GeneTex | GTX80958 |
| | Abnova Corporation | PAB20512 |
| | LifeSpan BioSciences | LS-C36410-100 |
| | Biorbyt | orb126744 |
| FAM20C | Atlas Antibodies | HPA019823 |
| | Santa Cruz Biotechnology, Inc. | sc-160322 |
| | Abnova Corporation | PAB21246 |
| | Fitzgerald Industries International | 70R-6353 |
| | LifeSpan BioSciences | LS-C82574-50 |
| CNTN1 | Fitzgerald Industries International | 70R-9772 |
| | Atlas Antibodies | HPA041060 |
| | antibodies-online | ABIN748823 |
| | LifeSpan BioSciences | LS-C116852-50 |
| | Abnova Corporation | PAB23744 |
| MGAT1 | Atlas Antibodies | HPA017432 |
| | antibodies-online | ABIN571229 |
| | Thermo Scientific Pierce Antibodies | PA5-12148 |
| | Abnova Corporation | PAB18956 |
| | LifeSpan BioSciences | LS-C99702-100 |
| STX1A | Abgent | AP9813a |
| | Fitzgerald Industries International | 70R-10562 |
| | Acris Antibodies GmbH | AP15806PU-M |
| | LifeSpan BioSciences | LS-C89914-100 |
| | Covance, Inc. | MMS-619R-500 |
| NMU | Atlas Antibodies | HPA025926 |
| | GeneTex | GTX87991 |
| | antibodies-online | ABIN461275 |
| | LifeSpan BioSciences | LS-C9258-50 |
| | Biorbyt | orb126042 |
| CD59 | antibodies-online | ABIN94204 |
| | Antigenix America Inc. | M590020 |
| | GeneTex | GTX74620 |
| | AbD Serotec | MCA1927T |
| | Thermo Scientific Pierce Antibodies | MA1-70058 |
| CASR | Atlas Antibodies | HPA039686 |
| | antibodies-online | ABIN460094 |
| | Spring Bioscience | E10624 |
| | Abnova Corporation | PAB18311 |
| | Acris Antibodies GmbH | AP20293PU-N |
| CPE | Santa Cruz Biotechnology, Inc. | sc-34321 |
| | LifeSpan BioSciences | LS-C119819-100 |
| | Proteintech Group Inc | 13710-1-AP |
| | R&D Systems | AF3587 |
| | Biorbyt | orb127922 |

It is generally preferable to immobilize either the antibody or proteins on a solid support for Western blots and immunofluorescence techniques. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means. Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

Other standard methods include immunoassay techniques which are well known to one of ordinary skill in the art and may be found in Principles And Practice Of Immunoassay, 2nd Edition, Price and Newman, eds., MacMillan (1997) and Antibodies, A Laboratory Manual, Harlow and Lane, eds., Cold Spring Harbor Laboratory, Ch. 9 (1988), each of which is incorporated herein by reference in its entirety.

Antibodies used in immunoassays to determine the level of a marker of the invention, may be labeled with a detectable label. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In one embodiment, the antibody is labeled, e.g. a radio-labeled, chromophore-labeled, fluorophore-labeled, or enzyme-labeled antibody. In another embodiment, an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a marker of the invention.

In one embodiment of the invention, proteomic methods, e.g., mass spectrometry, are used. Mass spectrometry is an analytical technique that consists of ionizing chemical compounds to generate charged molecules (or fragments thereof) and measuring their mass-to-charge ratios. In a typical mass spectrometry procedure, a sample is obtained from a subject, loaded onto the mass spectrometry, and its components (e.g., a marker of the invention) are ionized by different methods (e.g., by impacting them with an electron beam), resulting in the formation of charged particles (ions). The mass-to-charge ratio of the particles is then calculated from the motion of the ions as they transit through electromagnetic fields.

For example, matrix-associated laser desorption/ionization time-of-flight mass spectrometry (MALDI-TOF MS) or surface-enhanced laser desorption/ionization time-of-flight mass spectrometry (SELDI-TOF MS) which involves the application of a biological sample, such as serum, to a protein-binding chip (Wright, G. L., Jr., et al. (2002) *Expert Rev Mol Diagn* 2:549; Li, J., et al. (2002) *Clin Chem* 48:1296; Laronga, C., et al. (2003) *Dis Markers* 19:229; Petricoin, E. F., et al. (2002) 359:572; Adam, B. L., et al. (2002) *Cancer Res* 62:3609; Tolson, J., et al. (2004) *Lab Invest* 84:845; Xiao, Z., et al. (2001) *Cancer Res* 61:6029) can be used to determine the level of a marker of the invention.

Furthermore, in vivo techniques for determination of the level of a marker of the invention include introducing into a subject a labeled antibody directed against a marker of the invention, which binds to and transforms a marker of the invention into a detectable molecule. As discussed above, the presence, level, or even location of the detectable marker of the invention in a subject may be detected determined by standard imaging techniques.

In general, it is preferable that the difference between the level of a marker of the invention in a sample from a subject and the amount of a marker of the invention in a control sample, is as great as possible. Although this difference can be as small as the limit of detection of the method for determining the level of a marker it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the standard error of the assessment method.

B. Methods for Monitoring the Effectiveness of a Treatment

The present invention also provides methods for monitoring the effectiveness of a therapy or treatment regimen or any other therapeutic approach useful for inhibiting the development of impaired glucose tolerance and/or type 2 diabetes; reducing or slowing down the progression of normal glucose tolerance to impaired fasting glycaemia, to impaired glucose tolerance, and/or to diabetes; and/or reducing or inhibiting the development of complications associated with the disease in a subject. In these methods the level of one or more markers of the invention in a pair of samples (a first sample not subjected to the treatment regimen and a second sample subjected to at least a portion of the treatment regimen) is assessed. A modulation in the level of expression of the one or more markers in the first sample, relative to the second sample, is an indication that the therapy is effective for inhibiting the development of impaired glucose tolerance and/or type 2 diabetes; reduce or slow down the progression of normal glucose tolerance to impaired fasting glycaemia, to impaired glucose tolerance, and/or to diabetes; and/or reduce or inhibit the development of complications associated with the disease in a subject.

C. Screening Methods

Using the methods described herein, a variety of molecules, particularly molecules sufficiently small to be able to cross the cell membrane, may be screened in order to identify molecules which modulate, e.g., decrease or increase, the expression and/or activity of a marker(s) of the invention. Compounds so identified can be administered to a subject in order to inhibit the development of impaired glucose tolerance and/or type 2 diabetes; reduce or slow down the progression of normal glucose tolerance to impaired fasting glycaemia, to impaired glucose tolerance, and/or to diabetes; and/or reduce or inhibit the development of complications associated with the disease in a subject.

Accordingly, in one embodiment, the invention provides methods for identifying modulators, i.e., candidate or test compounds or agents (e.g., enzymes, peptides, peptidomimetics, small molecules, ribozymes, or marker antisense molecules) which bind to a marker polypeptide; have a stimulatory or inhibitory effect on a marker expression; marker processing; marker post-translational modification (e.g., glycosylation, ubiquitinization, or phosphorylation); marker activity; and/or have a stimulatory or inhibitory effect on the expression, processing or activity of a marker target molecule.

Methods for identifying a compound that can modulate the expression and/or activity of a marker in a cell (in vitro and/or in vivo), inhibit the development of impaired glucose tolerance and/or type 2 diabetes; reduce or slow down the progression of normal glucose tolerance to impaired fasting glycaemia, to impaired glucose tolerance, and/or to diabetes; and/or reduce or inhibit the development of complications associated with the disease in a subject (also referred to herein as screening assays) include separately contacting an aliquot of a sample (e.g., a sample from the subject) with each member of a library of compounds; determining the effect of a member of the library of compounds on the level of one or more marker(s) of the invention (or the activity of one or more marker(s) of the invention) in each of the aliquots; and selecting a member of the library of compounds which modulates the level of and/or the activity of the one or more marker(s) of the invention in an aliquot as compared to the level and/or activity of the one or more marker(s) of the invention in a control sample, thereby identifying a compound that can modulate the expression and/or activity of a marker in a cell, inhibit the development of impaired glucose tolerance and/or type 2 diabetes; reduce or slow down the progression of normal glucose tolerance to impaired fasting glycaemia, to impaired glucose tolerance, and/or to diabetes; and/or reduce or inhibit the development of complications associated with the disease in a subject.

As used interchangeably herein, the terms "marker activity" and "biological activity of a marker" include activities exerted by a marker(s) protein on marker responsive cell or tissue, or on marker(s) nucleic acid molecule or protein target molecule, as determined in vivo, and/or in vitro, according to standard techniques. A marker(s) activity can be a direct activity, such as an association with a marker-target molecule. Alternatively, marker(s) activity is an indirect activity, such as a downstream biological event mediated by interaction of the marker(s) protein with a marker-target molecule or other molecule in a signal-transduction pathway involving the marker(s). The biological activities of the markers of the invention are known in the art and can be found at, for example, the Uniprot database. The Uniprot Accession Numbers for each of the markers of the invention are provided in Tables 1-3. The entire contents of each of these Uniprot records is hereby incorporated by reference. Methods for determining the effect of a compound on the expression and/or activity of marker are known in the art and/or described herein.

A variety of test compounds can be evaluated using the screening assays described herein. The term "test compound" includes any reagent or test agent which is employed in the assays of the invention and assayed for its ability to influence the expression and/or activity of a marker. More than one compound, e.g., a plurality of compounds, can be tested at the same time for their ability to modulate the expression and/or activity of a marker in a screening assay. The term "screening assay" preferably refers to assays which test the ability of a plurality of compounds to influence the readout of choice rather than to tests which test the ability of one compound to influence a readout. Preferably, the subject assays identify compounds not previously known to have the effect that is being screened for. In one embodiment, high throughput screening can be used to assay for the activity of a compound.

Candidate/test compounds include, for example, 1) peptides such as soluble peptides, including Ig-tailed fusion peptides and members of random peptide libraries (see, e.g., Lam, K. S. et al. (1991) Nature 354:82-84; Houghten, R. et al. (1991) Nature 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) Cell 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), 6) mutant forms of marker(s) molecules, e.g., dominant negative mutant forms of the molecules, 7) nucleic acids, 8) carbohydrates, and 9) natural product extract compounds.

Test compounds can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds can be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner USP '409), plasmids (Cull et al. (1992) Proc Natl Acad Sci USA 89:1865-1869) or phage (Scott and Smith (1990) Science 249:386-390; Devlin (1990) Science 249: 404-406; Cwirla et al. (1990) Proc. Natl. Acad. Sci. 87:6378-6382; Felici (1991) J. Mol. Biol. 222:301-310; Ladner supra.).

Compounds identified in the screening assays can be used in methods of modulating one or more of the biological responses regulated by a marker, e.g., glucose tolerance. It will be understood that it may be desirable to formulate such compound(s) as pharmaceutical compositions prior to contacting them with cells.

Once a test compound is identified by one of the variety of methods described hereinbefore, the selected test compound (or "compound of interest") can then be further evaluated for its effect on cells, for example by contacting the compound of interest with cells either in vivo (e.g., by administering the compound of interest to a subject or animal model) or ex vivo (e.g., by isolating cells from the subject or animal model and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

Computer-based analysis of a marker with a known structure can also be used to identify molecules which will bind to a marker of the invention. Such methods rank molecules based on their shape complementary to a receptor site. For example, using a 3-D database, a program such as DOCK can be used to identify molecules which will bind to TLR9. See DesJarlias et al. (1988) J. Med. Chem. 31:722; Meng et al. (1992) J. Computer Chem. 13:505; Meng et al. (1993) Proteins 17:266; Shoichet et al. (1993) Science 259:1445. In addition, the electronic complementarity of a molecule to a marker can be analyzed to identify molecules which bind to the marker. This can be determined using, for example, a molecular mechanics force field as described in Meng et al. (1992) *J. Computer Chem.* 13:505 and Meng et al. (1993) *Proteins* 17:266. Other programs which can be used include CLIX which uses a GRID force field in docking of putative ligands. See Lawrence et al. (1992) *Proteins* 12:31; Goodford et al. (1985) *J. Med. Chem.* 28:849; Boobbyer et al. (1989) *J. Med. Chem.* 32:1083.

The instant invention also pertains to compounds identified using the foregoing screening assays.

D. Methods for Modulating the Expression and/or Activity of a Biomarker of the Invention Yet another aspect of the invention pertains to methods of modulating expression and/or activity of a marker in a cell. The modulatory methods of the invention involve contacting the cell with an agent that modulates the expression and/or activity of a marker such that the expression and/or activity of a marker in the cell is modulated. In order for the expression and/or activity of a marker to be modulated in a cell, the cell is contacted with a modulatory agent in an amount sufficient to modulate the expression and/or activity of a marker.

A "modulator" or "modulatory agent" is a compound or molecule that modulates, and may be, e.g., an agonist, antagonist, activator, stimulator, suppressor, or inhibitor. As used herein, the term "modulator" refers to any moiety which modulates activity of a marker(s), including moieties which modulates marker(s) expression or modulates marker(s) function. The modulator may act by modulating the activity of a marker polypeptide in the cell, (e.g., by contacting a cell with an agent that, e.g., interferes with the binding of a marker(s) to a molecule with which it interacts, changes the binding specificity of a marker(s), or post-translationally modifies a marker(s) or the expression of a marker(s), (e.g., by modulating transcription of the marker gene or translation of the marker mRNA). Accordingly, the invention features methods for modulating one or more biological responses regulated by a marker(s) by contacting the cells with a modulator of the expression and/or activity the marker(s) such that the biological response is modulated.

Representative modulators are described below and include, but are not limited to, proteins, nucleic acid molecules, antibodies, nucleic acids (e.g., antisense molecules, such as ribozymes and RNA interfering agents), immunoconjugates (e.g., an antibody conjugated to a therapeutic agent), small molecules, fusion proteins, adnectins, aptamers, anticalins, lipocalins, and marker-derived peptidic compounds.

As used herein, the term "contacting" (e.g., contacting a cell with a modulator) is intended to include incubating the modulator and the cell together in vitro (e.g., adding the modulator to cells in culture) or administering the modulator to a subject such that the modulator and cells of the subject are contacted in vivo. The term "contacting" is not intended to include exposure of cells to an agent that may occur naturally in a subject (i.e., exposure that may occur as a result of a natural physiological process).

In one embodiment, the modulatory methods of the invention are performed in vitro. In another embodiment, the modulatory methods of the invention are performed in vivo, e.g., in a subject, e.g., having impaired glucose tolerance, type 2 diabetes, that would benefit from modulation of the expression and/or activity of a marker of the invention.

Accordingly, the present invention also provides methods for inhibiting the development of impaired glucose tolerance and/or type 2 diabetes; reducing or slowing down the progression of normal glucose tolerance to impaired fasting glycaemia, to impaired glucose tolerance, and/or to diabetes; and/or reducing or inhibiting the development of complications associated with the disease in a subject The methods of "inhibiting", "slowing", and/or "treating" include administration of a marker modulator to a subject in order to cure or to prolong the health or survival of a subject beyond that expected in the absence of such treatment.

The terms "patient" or "subject" as used herein is intended to include human and veterinary patients. In a particular embodiment, the subject is a human. The term "non-human animal" includes all vertebrates, e.g., mammals and non-mammals, such as non-human primates, mice, rabbits, sheep, dog, cow, chickens, amphibians, and reptiles.

The methods of the invention also contemplate the use of marker(s) modulators in combination with other therapies, including life-style changes. Thus, in addition to the use of marker(s) modulators, the methods of the invention may also include administering to the subject one or more "standard" therapies. For example, the modulators can be administered in combination with (i.e., together with or linked to (i.e., an immunoconjugate)) cytotoxins, immunosuppressive agents, radiotoxic agents, and/or therapeutic antibodies. Particular co-therapeutics contemplated by the present invention include, but are not limited to, insulin sensitizers, secretagogues, dipeptidyl peptidase IV inhibitors, alpha-glucosidase inhibitors, amylinomimetics, incretin mimetics, insulin, bile acid sequestrants, dopamine agonists, statins.

Marker(s) modulators and the co-therapeutic agent or co-therapy can be administered in the same formulation or separately. In the case of separate administration, the marker(s) modulators can be administered before, after or concurrently with the co-therapeutic or co-therapy. One agent may precede or follow administration of the other agent by intervals ranging from minutes to weeks. In embodiments where two or more different kinds of therapeutic agents are applied separately to a subject, one would generally ensure that a significant period of time did not expire between the time of each delivery, such that these different kinds of agents would still be able to exert an advantageously combined effect on the target tissues or cells.

In one embodiment, the marker(s) modulators (e.g., an anti-marker(s) antibody) may be linked to a second binding molecule, such as an antibody (i.e., thereby forming a bispecific molecule) or other binding agent that, for example, binds to a different target or a different epitope on the marker(s).

The term "effective amount" as used herein, refers to that amount of marker(s) modulators, which is sufficient to inhibit the progression of fibrosis in a subject when administered to a subject. An effective amount will vary depending upon the subject and the severity of the disease and age of the subject, the manner of administration and the like, which can readily be determined by one of ordinary skill in the art. Marker(s) modulators dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of a marker(s) modulator. Dosage regimens may be adjusted to provide the optimum therapeutic response. An effective amount is also one in which any toxic or detrimental effects (i.e., side effects) of a marker(s) modulator are minimized and/or outweighed by the beneficial effects.

Actual dosage levels of the marker(s) modulators used in the methods of the present invention may be varied so as to obtain an amount of the active ingredient which is effective to achieve the desired response, e.g., inhibiting the progression of diabetes, for a particular patient, composition, and mode of administration, without being toxic to the patient. The selected dosage level will depend upon a variety of pharmacokinetic factors including the activity of the particular marker(s) modulator employed, or the ester, salt or amide thereof, the route of administration, the time of administration, the rate of excretion of the particular modulator being employed, the duration of the treatment, other drugs, compounds and/or materials used in combination with the particular modulator employed, the age, sex, weight, condition, general health and prior medical history of the patient being treated, and like factors well known in the medical arts. A physician or veterinarian having ordinary skill in the art can readily determine and prescribe the effective amount of the modulator required. For example, the physician or veterinarian could start doses of the modulator at levels lower than that required in order to achieve the desired therapeutic effect and gradually increase the dosage until the desired effect is achieved. In general, a suitable daily dose of a marker(s) modulator will be that amount which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a marker(s) modulator may be administered as two, three, four, five, six or more sub-doses administered separately at appropriate intervals throughout the day, optionally, in unit dosage forms. While it is possible for a marker(s) modulator of the present invention to be administered alone, it is preferable to administer the modulator as a pharmaceutical formulation (composition).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the marker(s) modulators used in the methods of the present invention may be administered once or twice weekly by subcutaneous injection or once or twice monthly by subcutaneous injection.

To administer a marker(s) modulator used in the methods of the present invention by certain routes of administration, it may be necessary to include the modulator in a formulation suitable for preventing its inactivation. For example, the marker(s) modulator may be administered to a subject in an appropriate carrier, for example, liposomes, or a diluent. Pharmaceutically acceptable diluents include saline and aqueous buffer solutions. Liposomes include water-in-oil-in-water CGF emulsions, as well as conventional liposomes (Strejan et al. (1984) *J. Neuroimmunol.* 7:27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active marker(s) modulator, use thereof in pharmaceutical compositions is contemplated. Supplementary active compounds can also be incorporated with the marker(s) modulator.

Marker(s) modulators used in the methods of the invention typically must be sterile and stable under the conditions of manufacture and storage. The modulator can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including an agent that delays absorption, for example, monostearate salts and gelatin.

Sterile injectable solutions can be prepared by incorporating the active modulator in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Marker(s) modulators that can be used in the methods of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the modulator which produces a therapeutic effect. Generally, out of one hundred percent, this amount will range from about 0.001% to about 90% of active ingredient, preferably from about 0.005% to about 70%, most preferably from about 0.01% to about 30%.

The phrases "parenteral administration" and "administered parenterally", as used herein, means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and non-aqueous carriers which may be employed along with the marker(s) modulators utilized in the methods of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Marker(s) modulatos may also be administered with adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When marker(s) modulators used in the methods of the present invention are administered to humans and animals, they can be given alone or as a pharmaceutical modulator containing, for example, 0.001 to 90% (more preferably, 0.005 to 70%, such as 0.01 to 30%) of active ingredient in combination with a pharmaceutically acceptable carrier.

Marker(s) modulators can be administered with medical devices known in the art. For example, in a preferred embodiment, a modulator can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

1. Inhibitory Agents

According to a modulatory method of the invention, the expression and/or activity of a marker(s) is inhibited in a cell or subject by contacting the cell with (or administering to a subject) an inhibitory agent. Inhibitory agents of the invention can be, for example, molecules that act to decrease or inhibit the expression and/or activity of the marker(s).

In one embodiment of the invention, the modulatory, e.g., therapeutic, and diagnostic methods described herein employ an antibody that binds, e.g., directly to or indirectly to, and inhibits marker(s) activity and/or down-modulates marker(s) expression.

The term "antibody" or "immunoglobulin," as used interchangeably herein, includes whole antibodies and any antigen binding fragment (i.e., "antigen-binding portion") or single chains thereof. An "antibody" comprises at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., a marker). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (Ward et al. (1989) Nature 341, 544-546), which consists of a $V_H$ domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242, 423-426; and Huston et al. (1988) Proc. Natl. Acad. Sci. USA 85, 5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "antibody", as used herein, includes polyclonal antibodies, monoclonal antibodies, chimeric antibodies, humanized antibodies, and human antibodies, and those that occur naturally or are recombinantly produced according to methods well known in the art.

In one embodiment, an antibody for use in the methods of the invention is a bispecific antibody. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) Clin. Exp. Immunol. 79, 315-321; Kostelny et al. (1992) J. Immunol. 148, 1547-1553.

In another embodiment, an antibody for use in the methods of the invention is a camelid antibody as described in, for example, PCT Publication WO 94/04678, the entire contents of which are incorporated herein by reference.

A region of the camelid antibody that is the small, single variable domain identified as $V_{HH}$ can be obtained by genetic engineering to yield a small protein having high affinity for a target, resulting in a low molecular weight, antibody-derived protein known as a "camelid nanobody". See U.S. Pat. No. 5,759,808; see also Stijlemans et al., 2004 J. Biol. Chem. 279: 1256-1261; Dumoulin et al., 2003 Nature 424: 783-788; Pleschberger et al., 2003 Bioconjugate Chem. 14: 440-448; Cortez-Retamozo et al., 2002 Int. J. Cancer 89: 456-62; and Lauwereys, et al., 1998 EMBO J. 17: 3512-3520. Engineered libraries of camelid antibodies and antibody fragments are commercially available, for example, from Ablynx, Ghent, Belgium. Accordingly, a feature of the present invention is a camelid nanobody having high affinity for a marker.

In other embodiments of the invention, an antibody for use in the methods of the invention is a diabody, a single chain diabody, or a di-diabody.

Diabodies are bivalent, bispecific molecules in which $V_H$ and $V_L$ domains are expressed on a single polypeptide chain, connected by a linker that is too short to allow for pairing between the two domains on the same chain. The $V_H$ and $V_L$ domains pair with complementary domains of another chain, thereby creating two antigen binding sites (see e.g., Holliger et al., 1993 Proc. Natl. Acad. Sci. USA 90:6444-6448; Poljak et al., 1994 Structure 2:1121-1123). Diabodies can be produced by expressing two polypeptide chains with either the structure $V_{HA}$-$V_{LB}$ and $V_{HB}$-$V_{LA}$ ($V_H$-$V_L$ configuration), or $V_{LA}$-$V_{HB}$ and $V_{LB}$-$V_{HA}$ ($V_L$-$V_H$ configuration) within the same cell. Most of them can be expressed in soluble form in bacteria.

Single chain diabodies (scDb) are produced by connecting the two diabody-forming polypeptide chains with linker of approximately 15 amino acid residues (see Holliger and Winter, 1997 Cancer Immunol. Immunother., 45(3-4):128-30; Wu et al., 1996 Immunotechnology, 2(1):21-36). scDb can be expressed in bacteria in soluble, active monomeric form (see Holliger and Winter, 1997 Cancer Immunol. Immunother., 45(34): 128-30; Wu et al., 1996 Immunotechnology, 2(1):21-36; Pluckthun and Pack, 1997 Immunotechnology, 3(2): 83-105; Ridgway et al., 1996 Protein Eng., 9(7):617-21).

A diabody can be fused to Fc to generate a "di-diabody" (see Lu et al., 2004 J. Biol. Chem., 279(4):2856-65).

Marker binding molecules that exhibit functional properties of antibodies but derive their framework and antigen binding portions from other polypeptides (e.g., polypeptides other than those encoded by antibody genes or generated by the recombination of antibody genes in vivo) may also be used in the methods of the present invention. The antigen binding domains (e.g., marker binding domains) of these binding molecules are generated through a directed evolution process. See U.S. Pat. No. 7,115,396. Molecules that have an overall fold similar to that of a variable domain of an antibody (an "immunoglobulin-like" fold) are appropriate scaffold proteins. Scaffold proteins suitable for deriving antigen binding molecules include fibronectin or a fibronectin dimer, tenascin, N-cadherin, E-cadherin, ICAM, titin, GCSF-receptor, cytokine receptor, glycosidase inhibitor, antibiotic chromoprotein, myelin membrane adhesion molecule P0, CD8, CD4, CD2, class I MHC, T-cell antigen receptor, CD1, C2 and I-set domains of VCAM-1, I-set immunoglobulin domain of myosin-binding protein C, I-set immunoglobulin domain of myosin-binding protein H, I-set immunoglobulin domain of telokin, NCAM, twitchin, neuroglian, growth hormone receptor, erythropoietin receptor, prolactin receptor, interferon-gamma receptor, β-galactosidase/glucuronidase, β-glucuronidase, transglutaminase, T-cell antigen receptor, superoxide dismutase, tissue factor domain, cytochrome F, green fluorescent protein, GroEL, and thaumatin.

To generate non-antibody binding molecules, a library of clones is created in which sequences in regions of the scaffold protein that form antigen binding surfaces (e.g., regions analogous in position and structure to CDRs of an antibody variable domain immunoglobulin fold) are randomized Library clones are tested for specific binding to the antigen of interest (e.g., TLR9) and for other functions (e.g., inhibition of biological activity of TLR9). Selected clones can be used as the basis for further randomization and selection to produce derivatives of higher affinity for the antigen.

High affinity binding molecules are generated, for example, using the tenth module of fibronectin III ($^{10}$Fn3) as the scaffold, described in U.S. Pat. Nos. 6,818,418 and 7,115,396; Roberts and Szostak, 1997 Proc. Natl. Acad. Sci USA 94:12297; U.S. Pat. Nos. 6,261,804; 6,258,558; and Szostak et al. WO98/31700, the entire contents of each of which are incorporated herein by reference.

Non-antibody binding molecules can be produced as dimers or multimers to increase avidity for the target antigen. For example, the antigen binding domain is expressed as a fusion with a constant region (Fc) of an antibody that forms Fc-Fc dimers. See, e.g., U.S. Pat. No. 7,115,396, the entire contents of which are incorporated herein by reference.

The therapeutic methods of the invention also may be practiced through the use of antibody fragments and antibody mimetics. As detailed below, a wide variety of antibody fragment and antibody mimetic technologies have now been developed and are widely known in the art. While a number of these technologies, such as domain antibodies, Nanobodies, and UniBodies make use of fragments of, or other modifications to, traditional antibody structures, there are also alternative technologies, such as Adnectins, Affibodies, DARPins, Anticalins, Avimers, and Versabodies that employ binding structures that, while they mimic traditional antibody binding, are generated from and function via distinct mechanisms. Some of these alternative structures are reviewed in Gill and Damle (2006) 17: 653-658.

Domain Antibodies (dAbs) are the smallest functional binding units of antibodies, corresponding to the variable regions of either the heavy (VH) or light (VL) chains of human antibodies. Domantis has developed a series of large and highly functional libraries of fully human VH and VL dAbs (more than ten billion different sequences in each library), and uses these libraries to select dAbs that are specific to therapeutic targets. In contrast to many conventional antibodies, domain antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; U.S. Serial No. 2004/0110941; European patent application No. 1433846 and European Patents 0368684 & 0616640; WO05/035572, WO04/101790, WO04/081026, WO04/058821, WO04/003019 and WO03/002609, the contents of each of which is herein incorporated by reference in its entirety.

Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3). Importantly, the cloned and isolated VHH domain is a perfectly stable polypeptide harboring the full antigen-binding capacity of the original heavy-chain antibody. Nanobodies have a high homology with the VH domains of human antibodies and can be further humanized without any loss of activity.

Nanobodies are encoded by single genes and are efficiently produced in almost all prokaryotic and eukaryotic hosts, e.g., *E. coli* (see, e.g., U.S. Pat. No. 6,765,087, which is herein incorporated by reference in its entirety), molds (for example *Aspergillus* or *Trichoderma*) and yeast (for example *Saccharomyces, Kluyveromyces, Hansenula* or *Pichia*) (see, e.g., U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see, e.g., WO 06/079372, which is herein incorporated by reference in its entirety) is a proprietary method for generating Nanobodies against a desired target, based on automated high-throughout selection of B-cells and could be used in the context of the instant invention.

UniBodies are another antibody fragment technology, however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. Further details of UniBodies may be obtained by reference to patent application WO2007/059782, which is herein incorporated by reference in its entirety.

Adnectin molecules are engineered binding proteins derived from one or more domains of the fibronectin protein. In one embodiment, adnectin molecules are derived from the fibronectin type 21 domain by altering the native protein which is composed of multiple beta strands distributed between two beta sheets. Depending on the originating tissue, fibronectin may contain multiple type 21 domains which may be denoted, e.g., $^1$Fn3, $^2$Fn3, $^3$Fn3, etc. Adnectin molecules may also be derived from polymers of $^{10}$Fn3 related molecules rather than a simple monomeric $^{10}$Fn3 structure.

Although the native $^{10}$Fn3 domain typically binds to integrin, $^{10}$Fn3 proteins adapted to become adnectin molecules are altered so to bind antigens of interest, e.g., a marker(s). In one embodiment, the alteration to the $^{10}$Fn3 molecule comprises at least one mutation to a beta strand. In a preferred embodiment, the loop regions which connect the beta strands of the $^{10}$Fn3 molecule are altered to bind to an antigen of interest, e.g., a marker(s).

The alterations in the $^{10}$Fn3 may be made by any method known in the art including, but not limited to, error prone PCR, site-directed mutagenesis, DNA shuffling, or other types of recombinational mutagenesis which have been referenced herein. In one example, variants of the DNA encoding the $^{10}$Fn3 sequence may be directly synthesized in vitro, and later transcribed and translated in vitro or in vivo. Alternatively, a natural $^{10}$Fn3 sequence may be isolated or cloned from the genome using standard methods (as performed, e.g., in U.S. Pat. Application No. 20070082365), and then mutated using mutagenesis methods known in the art.

An aptamer is another type of antibody-mimetic which may be used in the methods of the present invention. Aptamers are typically small nucleotide polymers that bind to specific molecular targets. Aptamers may be single or double stranded nucleic acid molecules (DNA or RNA), although DNA based aptamers are most commonly double stranded. There is no defined length for an aptamer nucleic acid; however, aptamer molecules are most commonly between 15 and 40 nucleotides long.

Aptamers may be generated using a variety of techniques, but were originally developed using in vitro selection (Ellington and Szostak. (1990) *Nature.* 346(6287):818-22) and the SELEX method (systematic evolution of ligands by exponential enrichment) (Schneider et al. 1992. *J Mol Biol.* 228(3):862-9) the contents of which are incorporated herein by reference. Other methods to make and uses of aptamers have been published including Klussmann. The Aptamer Handbook: Functional Oligonucleotides and Their Applications. ISBN: 978-3-527-31059-3; Ulrich et al. 2006. *Comb Chem High Throughput Screen* 9(8):619-32; Cerchia and de Franciscis. 2007. *Methods Mol Biol.* 361:187-200; Ireson and Kelland. 2006. *Mol Cancer Ther.* 2006 5(12):2957-62; U.S. Pat. Nos. 5,582,981; 5,840,867; 5,756,291; 6,261,783; 6,458,559; 5,792,613; 6,111,095; and U.S. patent application Ser. Nos. 11/482,671; 11/102,428; 11/291,610; and 10/627,543 which are all incorporated herein by reference.

Aptamer molecules made from peptides instead of nucleotides may also be used in the methods of the invention. Peptide aptamers share many properties with nucleotide aptamers (e.g., small size and ability to bind target molecules with high affinity) and they may be generated by selection methods that have similar principles to those used to generate nucleotide aptamers, for example Baines and Colas. 2006. *Drug Discov Today.* 11(7-8):334-41; and Bickle et al. 2006. *Nat Protoc.* 1(3):1066-91 which are incorporated herein by reference.

Affibody molecules represent a class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, et al. *Nat Biotechnol* 1997; 15:772-7.

Ronmark J, et al., *Eur J Biochem* 2002; 269:2647-55). Further details of Affibodies and methods of production thereof may be obtained by reference to U.S. Pat. No. 5,831,012 which is herein incorporated by reference in its entirety.

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

Additional information regarding DARPins and other DRP technologies can be found in U.S. Patent Application Publication No. 2004/0132028 and International Patent Application Publication No. WO 02/20565, both of which are hereby incorporated by reference in their entirety.

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved ß-barrel which supports four loops at one terminus of the protein. These loops form the entrance to a binding pocket and conformational differences in this part of the molecule account for the variation in binding specificity between individual lipocalins.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Additional information regarding Anticalins can be found in U.S. Pat. No. 7,250,297 and International Patent Application Publication No. WO 99/16873, both of which are hereby incorporated by reference in their entirety.

Another antibody mimetic technology useful in the context of the instant invention are Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in U.S. Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that could be used in the context of the instant invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

Additional information regarding Versabodies can be found in U.S. Patent Application Publication No. 2007/0191272 which is hereby incorporated by reference in its entirety.

SMIPs™ (Small Modular ImmunoPharmaceuticals-Trubion Pharmaceuticals) engineered to maintain and optimize target binding, effector functions, in vivo half-life, and expression levels. SMIPS consist of three distinct modular domains. First they contain a binding domain which may consist of any protein which confers specificity (e.g., cell surface receptors, single chain antibodies, soluble proteins, etc). Secondly, they contain a hinge domain which serves as a flexible linker between the binding domain and the effector domain, and also helps control multimerization of the SMIP drug. Finally, SMIPS contain an effector domain which may be derived from a variety of molecules including Fc domains or other specially designed proteins. The modularity of the design, which allows the simple construction of SMIPs with a variety of different binding, hinge, and effector domains, provides for rapid and customizable drug design.

More information on SMIPs, including examples of how to design them, may be found in Zhao et al. (2007) Blood 110:2569-77 and the following U.S. Pat. App. Nos. 20050238646; 20050202534; 20050202028; 20050202023; 20050202012; 20050186216; 20050180970; and 20050175614.

In another aspect, the methods of the present invention employ immunoconjugate agents that target a marker(s) and which inhibit or down-modulate the marker(s). Agents that can be targeted to a marker(s) include, but are not limited to, cytotoxic agents, anti-inflammatory agents, e.g., a steroidal or nonsteroidal inflammatory agent, or a cytotoxin antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In another embodiment, marker(s) modulator employed in the methods of the invention are small molecules. As used herein, the term "small molecule" is a term of the art and includes molecules that are less than about 7500, less than about 5000, less than about 1000 molecular weight or less than about 500 molecular weight, and inhibit marker(s) activity. Exemplary small molecules include, but are not limited to, small organic molecules (e.g., Cane et al. 1998. *Science* 282:63), and natural product extract libraries. In another embodiment, the compounds are small, organic non-peptidic compounds. Like antibodies, these small molecule inhibitors indirectly or directly inhibit the activity of a marker(s).

In another embodiment, the marker(s) modulator employed in the methods of the present invention is an antisense nucleic acid molecule that is complementary to a gene encoding a marker(s) or to a portion of that gene, or a recombinant expression vector encoding the antisense nucleic acid molecule. As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

The use of antisense nucleic acids to down-modulate the expression of a particular protein in a cell is well known in the art (see e.g., Weintraub, H. et al., Antisense RNA as a molecular tool for genetic analysis, *Reviews—Trends in Genetics*, Vol. 1(1) 1986; Askari, F. K. and McDonnell, W. M. (1996) *N. Eng. J. Med.* 334:316-318; Bennett, M. R. and Schwartz, S. M. (1995) *Circulation* 92:1981-1993; Mercola, D. and Cohen, J. S. (1995) *Cancer Gene Ther.* 2:47-59; Rossi, J. J. (1995) *Br. Med. Bull.* 51:217-225; Wagner, R. W. (1994) *Nature* 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Antisense nucleic acids can be designed according to the rules of Watson and Crick base pairing. The antisense nucleic acid molecule can be complementary to the entire coding region of marker(s) mRNA, but more preferably is an oligonucleotide which is antisense to only a portion of the coding or noncoding region of marker(s) mRNA. For example, the antisense oligonucleotide can be complementary to the region surrounding the translation start site of marker(s) mRNA. An antisense oligonucleotide can be, for example, about 5, 10, 15, 20, 25, 30, 35, 40, 45 or 50 nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules that can be utilized in the methods of the present invention are typically administered to a subject or generated in situ such that they hybridize with or bind to cellular mRNA and/or genomic DNA encoding a marker(s) to thereby inhibit expression by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using vectors well known in the art and described in, for example, US20070111230 the entire contents of which are incorporated herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule employed by the methods of the present invention can include an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In another embodiment, an antisense nucleic acid used in the methods of the present invention is a compound that mediates RNAi. RNA interfering agents include, but are not limited to, nucleic acid molecules including RNA molecules which are homologous to a marker(s) or a fragment thereof, "short interfering RNA" (siRNA), "short hairpin" or "small hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999)). The process occurs when an endogenous ribonuclease cleaves the longer dsRNA into shorter, 21- or 22-nucleotide-long RNAs, termed small interfering RNAs or siRNAs. The small RNA segments then mediate the degradation of the target mRNA. Kits for synthesis of RNAi are commercially available from, e.g., New England Biolabs and Ambion. In one embodiment one or more of the chemistries described above for use in antisense RNA can be employed.

In still another embodiment, an antisense nucleic acid is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988, *Nature* 334:585-591) can be used to catalytically cleave marker(s) mRNA transcripts to thereby inhibit translation of the marker(s) mRNA.

Alternatively, gene expression can be inhibited by targeting nucleotide sequences complementary to the regulatory region of a marker(s) (e.g., the promoter and/or enhancers) to form triple helical structures that prevent transcription of the marker(s) gene. See generally, Helene, C., 1991, *Anticancer Drug Des.* 6(6):569-84; Helene, C. et al., 1992, *Ann. N.Y. Acad. Sci.* 660:27-36; and Maher, L. J., 1992, *Bioassays* 14(12):807-15.

In another embodiment, the marker(s) modulator used in the methods of the present invention is a fusion protein or peptidic compound derived from the marker(s) amino acid sequence. In particular, the inhibitory compound comprises a fusion protein or a portion of a marker(s) (or a mimetic thereof) that mediates interaction of the marker(s) with a target molecule such that contact of the marker(s) with this fusion protein or peptidic compound competitively inhibits the interaction of the marker(s) with the target molecule. Such fusion proteins and peptidic compounds can be made using standard techniques known in the art. For example, peptidic compounds can be made by chemical synthesis using standard peptide synthesis techniques and then introduced into cells by a variety of means known in the art for introducing peptides into cells (e.g., liposome and the like).

The in vivo half-life of the fusion protein or peptidic compounds of the invention can be improved by making peptide modifications, such as the addition of N-linked glycosylation sites into the marker(s) or conjugating the marker(s) to poly(ethylene glycol) (PEG; pegylation), e.g., via lysine-monopegylation. Such techniques have proven to be beneficial in prolonging the half-life of therapeutic protein drugs. It is expected that pegylation of marker(s) polypeptides of the invention may result in similar pharmaceutical advantages.

In addition, pegylation can be achieved in any part of a polypeptide of the invention by the introduction of a nonnatural amino acid. Certain nonnatural amino acids can be introduced by the technology described in Deiters et al., *J Am Chem Soc* 125:11782-11783, 2003; Wang and Schultz, *Science* 301:964-967, 2003; Wang et al., *Science* 292:498-500, 2001; Zhang et al., *Science* 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the nonnatural amino acid of choice. Particular nonnatural amino acids that are beneficial for purpose of conjugating moieties to the polypeptides of the invention include those with acetylene and azido side chains. Marker(s) polypeptides containing these novel amino acids can then be pegylated at these chosen sites in the protein.

2. Stimulatory Agents

According to a modulatory method of the invention, the expression and/or activity of a marker(s) is stimulated in a cell or subject by contacting the cell with (or administering to a subject) a stimulatory agent. Stimulatory agents of the invention can be, for example, molecules that act to stimulate or increase the expression and/or activity of the marker(s).

Examples of such stimulatory agents include active marker(s) polypeptide and nucleic acid molecules encoding the marker(s) that are introduced into the cell to increase expression and/or activity of the marker in the cell. A preferred stimulatory agent is a nucleic acid molecule encoding a marker(s) polypeptide, wherein the nucleic acid molecule is introduced into the cell in a form suitable for expression of the active marker(s) polypeptide in the cell. To express a marker(s) polypeptide in a cell, typically a marker(s)-encoding cDNA (full length or partial cDNA sequence) is first introduced into a recombinant expression vector using standard molecular biology techniques, and the vector may be transfected into cells using standard molecular biology techniques. A cDNA can be obtained, for example, by amplification using the polymerase chain reaction (PCR), using primers based on the marker(s) nucleotide sequence or by screening an appropriate cDNA library.

The nucleic acids for use in the methods of the invention can also be prepared, e.g., by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

In one embodiment, a nucleic acid molecule encoding a marker(s) may be present in an inducible construct. In another embodiment, a nucleic acid molecule encoding marker(s) may be present in a construct which leads to constitutive expression. In one embodiment, a nucleic acid molecule encoding marker(s) may be delivered to cells, or to subjects, in the absence of a vector.

A nucleic acid molecule encoding marker(s) may be delivered to cells or to subjects using a viral vector, preferably one whose use for gene therapy is well known in the art. Techniques for the formation of vectors or virions are generally described in "Working Toward Human Gene Therapy," Chapter 28 in Recombinant DNA, 2nd Ed., Watson, J. D. et al., eds., New York: Scientific American Books, pp. 567-581 (1992). An overview of suitable viral vectors or virions is provided in Wilson, J. M., Clin. Exp. Immunol. 107(Suppl. 1):31-32 (1997), as well as Nakanishi, M., Crit. Rev. Therapeu. Drug Carrier Systems 12:263-310 (1995); Robbins, P. D., et al., Trends Biotechnol. 16:35-40 (1998); Zhang, J., et al., Cancer Metastasis Rev. 15:385-401(1996); and Kramm, C. M., et al., Brain Pathology 5:345-381 (1995). Such vectors may be derived from viruses that contain RNA (Vile, R. G., et al., Br. Med Bull. 51:12-30 (1995)) or DNA (Ali M., et al., Gene Ther. 1:367-384 (1994)).

Examples of viral vector systems utilized in the gene therapy art and, thus, suitable for use in the present invention, include the following: retroviruses (Vile, R. G., supra; U.S. Pat. Nos. 5,741,486 and 5,763,242); adenoviruses (Brody, S. L., et al., Ann. N.Y. Acad. Sci. 716: 90-101 (1994); Heise, C. et al., Nat. Med. 3:639-645 (1997)); adenoviral/retroviral chimeras (Bilbao, G., et al., FASEB J. 11:624-634 (1997); Feng, M., et al., Nat. Biotechnol. 15:866-870 (1997)); adeno-associated viruses (Flotte, T. R. and Carter, B. J., Gene Ther. 2:357-362 (1995); U.S. Pat. No. 5,756,283); herpes simplex virus I or II (Latchman, D. S., Mol. Biotechnol. 2:179-195 (1994); U.S. Pat. No. 5,763,217; Chase, M., et al., *Nature* Biotechnol. 16:444-448 (1998)); parvovirus (Shaughnessy, E., et al., Semin Oncol. 23:159-171 (1996)); reticuloendotheliosis virus (Donburg, R., Gene Therap. 2:301-310 (1995)). Extrachromosomal replicating vectors may also be used in the gene therapy methods of the present invention. Such vectors are described in, for example, Calos, M. P. (1996) Trends Genet. 12:463-466, the entire contents of which are incorporated herein by reference. Other viruses that can be used as vectors for gene delivery include poliovirus, papillomavirus, vaccinia virus, lentivirus, as well as hybrid or chimeric vectors incorporating favorable aspects of two or more viruses (Nakanishi, M. (1995) Crit. Rev. Therapeu. Drug Carrier Systems 12:263-310; Zhang, J., et al. (1996) Cancer Metastasis Rev. 15:385-401; Jacoby, D. R., et al. (1997) Gene Therapy 4:1281-1283).

The term "AAV vector" refers to a vector derived from an adeno-associated virus serotype, including without limitation, AAV-1, AAV-2, AAV-3, AAV-4, AAV-5, or AAVX7. "rAAV vector" refers to a vector that includes AAV nucleotide sequences as well as heterologous nucleotide sequences. rAAV vectors require only the 145 base terminal repeats in cis to generate virus. All other viral sequences are dispensable and may be supplied in trans (Muzyczka (1992) Curr. Topics Microbiol. Immunol. 158:97). Typically, the rAAV vector genome will only retain the inverted terminal repeat (ITR) sequences so as to maximize the size of the transgene that can be efficiently packaged by the vector. The ITRs need not be the wild-type nucleotide sequences, and may be altered, e.g., by the insertion, deletion or substitution of nucleotides, as long as the sequences provide for functional rescue, replication and packaging. In particular embodiments, the AAV vector is an AAV2/5 or AAV2/8 vector. Suitable AAV vectors are described in, for example, U.S. Pat. No. 7,056,502 and Yan et al. (2002) J. Virology 76(5): 2043-2053, the entire contents of which are incorporated herein by reference.

As used herein, the term "lentivirus" refers to a group (or genus) of retroviruses that give rise to slowly developing disease. Viruses included within this group include HIV (human immunodeficiency virus; including but not limited to HIV type 1 and HIV type 2), the etiologic agent of the human acquired immunodeficiency syndrome (AIDS); visna-maedi, which causes encephalitis (visna) or pneumonia (maedi) in sheep; the caprine arthritis-encephalitis virus, which causes immune deficiency, arthritis, and encephalopathy in goats; equine infectious anemia virus (EIAV), which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells). In one embodiment of the invention, the lentivirus is not HIV.

As used herein, the term "adenovirus" ("Ad") refers to a group of double-stranded DNA viruses with a linear genome of about 36 kb. See, e.g., Berkner et al., Curr. Top. Microbiol. Immunol., 158: 39-61 (1992). In some embodiments, the adenovirus-based vector is an Ad-2 or Ad-5 based vector. See, e.g., Muzyczka, Curr. Top. Microbiol. Immunol., 158: 97-123, 1992; Ali et al., 1994 Gene Therapy 1: 367-384; U.S. Pat. Nos. 4,797,368, and 5,399,346. Suitable adenovirus vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types. Additionally, introduced adenovirus DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenovirus genome for foreign DNA is large (up to 8 kilobases) relative to other gene delivery vectors (Haj-Ahmand et al. J. Virol. 57, 267-273 [1986]).

In one embodiment, an adenovirus is a replication defective adenovirus. Most replication-defective adenoviral vectors currently in use have all or parts of the viral E1 and E3 genes deleted but retain as much as 80% of the adenovirus genetic material. Adenovirus vectors deleted for all viral coding regions are also described by Kochanek et al. and Chamberlain et al. (U.S. Pat. Nos. 5,985,846 and 6,083,750). Such viruses are unable to replicate as viruses in the absence of viral products provided by a second virus, referred to as a "helper" virus.

In one embodiment, an adenoviral vector is a "gutless" vector. Such vectors contain a minimal amount of adenovirus DNA and are incapable of expressing any adenovirus antigens (hence the term "gutless"). The gutless replication defective Ad vectors provide the significant advantage of accommodating large inserts of foreign DNA while completely eliminating the problem of expressing adenoviral genes that result in an immunological response to viral proteins when a gutless replication defective Ad vector is used in gene therapy. Methods for producing gutless replication defective Ad vectors have been described, for example, in U.S. Pat. No. 5,981,225 to Kochanek et al., and U.S. Pat. Nos. 6,063,622 and 6,451,596 to Chamberlain et al; Parks et al., PNAS 93:13565 (1996) and Lieber et al., J. Virol. 70:8944-8960 (1996).

In another embodiment, an adenoviral vector is a "conditionally replicative adenovirus" ("CRAds"). CRAds are genetically modified to preferentially replicate in specific cells by either (i) replacing viral promoters with tissue specific promoters or (ii) deletion of viral genes important for replication that are compensated for by the target cells only. The skilled artisan would be able to identify epithelial cell specific promoters.

Other art known adenoviral vectors may be used in the methods of the invention. Examples include Ad vectors with recombinant fiber proteins for modified tropism (as described in, e.g., van Beusechem et al., 2000 Gene Ther. 7: 1940-1946), protease pre-treated viral vectors (as described in, e.g., Kuriyama et al., 2000 Hum. Gene Ther. 11: 2219-2230), E2a temperature sensitive mutant Ad vectors (as described in, e.g., Engelhardt et al., 1994 Hum. Gene Ther. 5: 1217-1229), and "gutless" Ad vectors (as described in, e.g., Armentano et al., 1997 J. Virol. 71: 2408-2416; Chen et al., 1997 Proc. Nat. Acad. Sci. USA 94: 1645-1650; Schieder et al., 1998 Nature Genetics 18: 180-183).

The vector will include one or more promoters or enhancers, the selection of which will be known to those skilled in the art. Suitable promoters include, but are not limited to, the retroviral long terminal repeat (LTR), the SV40 promoter, the human cytomegalovirus (CMV) promoter, and other viral and eukaryotic cellular promoters known to the skilled artisan.

Guidance in the construction of gene therapy vectors and the introduction thereof into affected subjects for therapeutic purposes may be obtained in the above-referenced publications, as well as in U.S. Pat. Nos. 5,631,236, 5,688,773, 5,691,177, 5,670,488, 5,529,774, 5,601,818, and PCT Publication No. WO 95/06486, the entire contents of which are incorporated herein by reference.

Generally, methods are known in the art for viral infection of the cells of interest. The virus can be placed in contact with the cell of interest or alternatively, can be injected into a subject suffering from a retinal disorder, for example, as described in U.S. Provisional Patent Application No. 61/169,835 and PCT Application No. PCT/US09/053730, the contents of each of which are incorporated by reference.

Gene therapy vectors comprising a nucleic acid molecule encoding a marker(s) can be delivered to a subject or a cell by any suitable method in the art, for example, intravenous injection, local administration, e.g., application of the nucleic acid in a gel, oil, or cream, (see, e.g., U.S. Pat. No. 5,328,470), stereotactic injection (see, e.g., Chen et al. (1994) Proc. Natl. Acad. Sci. U.S.A. 91:3054), gene gun, or by electroporation (see, e.g., Matsuda and Cepko (2007) Proc. Natl. Acad. Sci. U.S.A. 104:1027), using lipid-based transfection reagents, or by any other suitable transfection method.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAM-FECT™ (OZ Biosciences, France) and the like), or electroporation (e.g., in vivo electroporation). Suitable methods for transforming or transfecting host cells can be found in Sambrook, et al. (Molecular Cloning: A Laboratory Manual. 2nd, ed., Cold Spring harbor Laboratory, Cold Spring Harbor Laboratory Press, Cold Spring Harbor, N.Y., 1989), and other laboratory manuals.

In one embodiment, a marker(s) is delivered to a subject or cells in the form of a peptide or protein. In order to produce such peptides or proteins, recombinant expression vectors of the invention can be designed for expression of one or more marker(s) proteins, and/or portion(s) thereof in prokaryotic or eukaryotic cells. For example, one or more glucose transporter proteins and/or portion(s) thereof can be expressed in bacterial cells such as $E.\ coli$, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

In one embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include retinal cell-type-specific promoters (e.g., rhodopsin regulatory sequences, Cabp5, Cralbp, Nrl, Crx, Ndrg4, clusterin, Rax, Hest and the like (Matsuda and Cepko, supra)), the albumin promoter (liver-specific, Pinkert et al. (1987) Genes Dev. 1:268), neuron-specific promoters (e.g., the neurofilament promoter; Byrne and Ruddle (1989) Proc. Natl. Acad. Sci. U.S.A. 86:5473). Developmentally-regulated promoters are also encompassed, for example the α-fetoprotein promoter (Campes and Tilghman (1989) Genes Dev. 3:537).

Application of the methods of the invention for the treatment and/or prevention of a retinal disorder can result in curing the disorder, decreasing at least one symptom associated with the disorder, either in the long term or short term or simply a transient beneficial effect to the subject. Accordingly, as used herein, the terms "treat," "treatment" and "treating" include the application or administration of agents, as described herein, to a subject who is suffering from a retinal disorder, or who is susceptible to such conditions with the purpose of curing, healing, alleviating, relieving, altering, remedying, ameliorating, improving or affecting such conditions or at least one symptom of such conditions. As used herein, the condition is also "treated" if recurrence of the condition is reduced, slowed, delayed or prevented.

A modulatory agent, such as a chemical compound, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described above.

E. Methods of Identifying Type 2 Diabetes Biomarkers

The present invention further provides methods for identifying type 2 diabetes biomarkers useful as markers for, e.g., disease (prognostics and diagnostics), therapeutic effectiveness of a drug (theranostics) and of drug toxicity. For example, as described above, the markers described herein and the markers identified using the methods for biomarker discovery are useful for, e.g., determining whether a subject has or will develop impaired glucose tolerance; determining whether a subject has or will develop type 2 diabetes; determining whether a subject having type 2 diabetes will respond to a diabetic therapy; monitoring the effectiveness of a therapy for inhibiting the development of impaired glucose tolerance and/or type 2 diabetes, reducing or slowing down the progression of normal glucose tolerance to impaired fasting glycaemia, to impaired glucose tolerance, and/or to diabetes, and/or reducing or inhibiting the development of complications associated with the disease in a subject; in screening assays to identify molecules which modulate, e.g., decrease or increase, the expression and/or activity of a marker(s) of the invention for e.g., use as therapeutics.

Methods for identifying a type 2 diabetes marker are described in the working examples and include identifying proteins in the secretory vesicles of two or more organs from two or more species under steady state conditions, identifying proteins in the secretory vesicles of pancreatic β cells thereby generating a provisional list of steady state markers, identifying the markers in the provisional list of steady state markers from the two or more organs from the two or more species common to the markers in the secretory vesicles of pancreatic β cells and removing those markers from the provisional list of steady state markers, thereby generating a list of β cell mass markers; identifying proteins in the secretory vesicles of pancreatic β cells under dysfunctional conditions, identifying proteins in the secretory vesicles of pancreatic β cells under normal conditions, identifying the proteins that were differentially expressed under dysfunctional conditions and under normal conditions, thereby generating a provisional list of β cell function markers, determining the level of a β cell mass marker and/or a β cell function marker in a sample form a control subject, e.g., a having normal glucose tolerance, determining the level of the marker in a test sample from a subject having, e.g., impaired glucose tolerance and/or type 2 diabetes. A difference in the level of a marker in the control sample as compared to the level in the test sample, e.g., a statistically significant level, identifies the marker as a type 2 diabetes biomarker.

A type 2 diabetes marker may also be identified by determining the level of a protein in a first sample obtained from a subject having type 2 diabetes prior to providing at least a portion of a therapy to the subject, and determining the level of a protein in a second sample obtained from the subject following provision of at least a portion of the therapy. A difference in the level of expression of the protein in the second sample relative to the first sample, e.g., a statistically significant level, identifies the protein as a type 2 diabetes marker.

IV. Kits of the Invention

The invention also provides kits for determining whether a subject has or will develop impaired glucose tolerance and/or whether a subject has or will develop type 2 diabetes. Kits to determine whether a subject will develop type 2 diabetes complications, to determine whether a treatment will be efficacious for treating a subject having impaired glucose tolerance and/or type 2 diabetes and kits for monitoring the effectiveness of a treatment are also provided.

These kits include means for determining the level of one or more markers of the invention and instructions for use of the kit.

The kits of the invention may optionally comprise additional components useful for performing the methods of the invention. By way of example, the kits may comprise reagents for obtaining a biological sample from a subject, a control sample, one or more sample compartments, a diabetic therapeutic, an instructional material which describes performance of a method of the invention and tissue specific controls/standards.

The reagents for determining the level of one or more marker(s) can include, for example, buffers or other reagents for use in an assay for evaluating the level of one or more markers, e.g., expression level (e.g., at either the mRNA or protein level). The instructions can be, for example, printed instructions for performing the assay for evaluating the level of one or more marker(s) of the invention.

The reagents for isolating a biological sample from a subject can comprise one or more reagents that can be used to obtain a fluid or tissue from a subject, such as means for obtaining a saliva or blood.

The kits of the invention may further comprise reagents for culturing a sample obtained from a subject.

Preferably, the kits are designed for use with a human subject.

The present invention is further illustrated by the following examples which should not be construed as further limiting. The contents of all references, patents and published patent applications cited throughout this application, as well as the Figures, are expressly incorporated herein by reference in their entirety.

EXAMPLES

Example I. Biomarker Identification

Materials and Methods

Candidate biomarkers were identified by evaluating proteins known or suspected to be secreted by pancreatic beta islets.

Three in vitro systems were used to identify secretory protein candidate biomarkers, primary human islets and 2 pancreatic ß-cell lines. The primary human islets were obtained from donors lacking major medical problems. Table 5 lists the characteristics of the donors. The cell lines used were the rat INS832/13 and the mouse MIN6. The experimental systems were analyzed using two conditions, steady state, and during an experimental dysfunctional state designed to mimic the pancreatic beta cell dysfunction observed in type 2 diabetes.

TABLE 5

Pancreatic islet donor characteristics.

| Donor | VP146 | VP149 | VP151 | VP152 | Paraskevas | VP157 | VP166 | VP167 |
|---|---|---|---|---|---|---|---|---|
| Gender | F | F | M | F | M | F | M | F |
| Age | 43 | 44 | 59 | 35 | 29 | 26 | 59 | 50 |
| Ethnicity | Caucasian | African American | Caucasian | Caucasian | Caucasian | African American | Caucasian | African American |
| Ht (cm) | 172.5 | 149.9 cm | 175 | 157.5 | | 1.59 | 170 | 157.5 |
| Wt (kg) | 104 kg | 66.8 kg | 84.5 | 80.6 | | 84 | 61.8 | 93 |
| BMI | 34.9 | 29.6 | 27 | 31.6 | 22.1 | 33 | 20.7 | 36.3 |
| Cause of death | Anoxic brain injury | ICH | Head trauma | Head trauma | Anoxic brain injury | HT/BI secondary to MVA | CVA/ICH | CVA/ICH |
| Smoking | no | quit 13 y ago | Occasional (cigar) | Yes (1 ppd) | ? | <1 ppd | Occasional (cigar) | No |
| EtOH | 2-3/wk | 1 glass wive/day | Occasional | No | ? | rare, <1 month | Occasional | No |
| Serologies | Neg | Neg | CMV+ | CMV+, EBV+ | None | Neg | EBV+ | Neg |
| Medicines | None | None | None | None | None | None | None | None |
| Disease | None | None | None | None | None | None | None | None |

ICH; Intracerebral hemorrhage.,
HT/BI; Head Trauma/brain injury
MVA; Motor vehicle accident.,
EBV+; Epstein-Barr virus positive,
CMV; Cytomegalovirus positive For identification of proteins secreted during steady state, the cell lines were cultivated in RPMI containing 5 mM glucose and the primary human islets were kept in saline at 4° C. until secretory vesicle sample preparation. For identification of proteins secreted during a dysfunctional state, the experimental systems were incubated with 20 mM glucose/0.4 mM palmitate or with 25 mM glucose/0.4 mM palmitate (El-Assaad et al. (2010) *Endocrinology* 151:3061-73) until insulin production was reduced by at least 30% and programmed cell death was induced, events that typically occurred between 16-24 hours for the cell lines and between 36-72 hours for the primary islets.

Secretory protein preparations from both steady state and dysfunctionalized islets and cell lines were made using the same process. At least 4 independent replicates were used per experimental system. The cultured cells were harvested by scraping, centrifuged for 5 minutes at 4° C. at 1400 rpm to remove debris and resuspended in homogenization buffer (250 mM sucrose/10 mM Tris pH 7.4/protease inhibitor EDTA-free cocktail). The islet or cell line suspensions were homogenized using a Dounce homogenizer. The homogenate was adjusted to 1.4M sucrose. A 14 ml SW40Ti ultra-clear centrifuge tube (Beckman Coulter #344060) was layered with homogenate followed by 4 ml of 1.2M sucrose and topped with 0.8M sucrose. The samples were centrifuged for 2 hours at 155,000 g at 4° C. and vesicles were harvested from the 0.8-1.2M interface. The vesicles were washed in 0.5M KCl followed by incubation in ammonium carbonate pH11. Vesicle content was separated from the vesicle membranes by centrifugation at 112,000 g. Protein yields were measured using the BCA Protein Assay (Pierce #23227). In instances where sample was limiting, the entire secretory vesicle was processed for mass spectrometry analysis. Western blot characterization of the starting cell line homogenates and secretory protein final products were done using antibodies against proteins expressed in specific subcellular compartments, such as the plasma membrane, endoplasmic reticulum (ER), Golgi apparatus, and mitochondria. Both membrane-bound and soluble proteins associated with these compartments were used, to assess the relative enrichment of potentially secreted proteins from the relevant subcellular compartments in the preparations. FIG. 1 depicts Western blots of starting materials (Hom), intermediate (SV) and final product (SC) preparations of secreted proteins from a rat cell line (A) and human primary islets (B).

An additional set of secretory protein samples were prepared from a selection of major organs or from organs known to become involved in diabetes disease progression and complications, using the process described above, substituting more robust mechanical tissue disruption for the more fibrous organs. To generate the human organ secretome dataset, secretory proteins from lung, breast, kidney, prostate, bladder, and colon were prepared. For the rat dataset, secretory proteins from heart, liver, kidney, skeletal muscle, subcutaneous fat, and whole pancreas were prepared. This experiment was done in order to identify the secretory proteins that can also be made by other tissues than the primary islets or the beta cell lines. Secretory proteins that can be made by multiple tissues would thus likely have relatively less tissue specificity, and would thus be de-prioritized as biomarker candidates.

Once the secretory protein samples were generated they were further processed for mass spectrometry data acquisition and peptide and protein identification. Briefly, the samples were digested with trypsin to generate peptides. The peptides were then separated by strong cation exchange chromatography (SCX) into three fractions. Each of the three fractions per sample was analyzed by reversed phase liquid chromatography, coupled by electrospray to a Waters QTOF mass spectrometer (LC-MS). Components were detected and matched across all samples and compared for relative peak intensity. Peak intensity was normalized to account for small differences in protein concentration between samples. ANOVA was then applied to identify peptides that were differentially expressed between the groups of interest in the samples derived from dysfunctionalized islets or cell lines. High stringency thresholds were used to ensure the statistical significance of the identified peptides. All intensity values were log (base e) transformed with values <0 replaced by 0. A subset of the samples was used to create an average sample (i.e., the Reference sample) against which all samples were then normalized. The normalization factors were chosen so that the median of log ratios between each sample and the Reference sample over all the peptides was adjusted to zero. Peptide identification was done with custom protein database using Mascot (Matrix Science) software. Candidate biomarker annotation was done using a combination of manual literature review and network and pathway analysis (Ingenuity).

Several thousand proteins were identified in the secretomes of the primary islets, cell lines, and organs in the steady state. The secretory proteins identified in the islets or cell lines that were also found in the organ secretomes were removed. The remaining proteins were ordered to identify which subset was expressed either in the primary human islets alone, or also in at least one of the cell lines. A total of 170 proteins met these criteria, and these proteins therefore constituted the initial steady state biomarker dataset.

A similar process was used to identify the initial dysfunctionalized biomarker dataset. An additional requirement to the two previously described criteria was that any of the candidate biomarkers also be differentially expressed by at least 1.5-fold in the dysfunctional state compared to control. A total of 245 proteins met the criteria and these proteins therefore constituted the initial dysfunctionalized biomarker dataset.

Subjects used for the plasma-based biomarker verification analyses are indicated in Tables 6 and 7. Plasma was processed using 3 different methods. First, common high abundance plasma proteins were removed using affinity chromatography methods. Removing the most abundant plasma proteins allowed less abundant plasma proteins to be more readily measured. Some of the biomarker candidates, however, were expected to be present beneath the current level of detection of the MRM-MS assays deployed. To measure candidates from this low abundance class of biomarkers commercially available ELISA kits were used. Lastly, plasma was processed to enrich for exosomes. Exosomes are small vesicles that are secreted whole by numerous cell types under normal and disease conditions. Originally described in immune and central nervous system interactions, exosomes have since been described to be produced by multiple tissue types, and are present in multiple different body fluids including plasma. Exosomes and are now understood to be part of a general, widely used secretion mechanism.

Sequential high speed centrifugation methods were used to enrich the exosomes present in blood (Graner M W et al. (2009) *FASEB J.* 23:1541), and this method was used to make exosome preparations from the majority of clinical samples obtained. Analysis of these preparations was expected to test the performance of biomarker that would not otherwise be detected, including low abundance proteins but also membrane associated proteins not expected to be readily solubilized in blood.

TABLE 6

Characteristics of subjects used for verification of BCM/BCF candidate biomarkers

| Cohort | Samples |
| --- | --- |
| Normoglycemic subject: NGT | 47 |
| Normoglycemic subject: IGT | 17 |
| Long term T1D (insulin > 5 yrs) | 19 |
| Long term T2D (insulin > 5 yrs) | 28 |

TABLE 7

Additional subjects used for verification of BCM/BCF/TEM candidate biomarkers ALL SUBJECTS

| | Number of subjects | Age range | Age median | BMI range | BMI median |
| --- | --- | --- | --- | --- | --- |
| Controls | 50 | 18-74 | 40 | 18-30 | 24 |
| Diabetics High BMI | 69 | 24-66 | 51 | 39-74 | 58 |
| Pre-Diabetics High BMI | 79 | 19-64 | 40 | 37-75 | 60 |
| Diabetics Lower BMI | 50 | 26-71 | 52 | 33-40 | 39 |
| Pre-Diabetics Lower BMI | 47 | 30-62 | 41 | 32-40 | 38 |

Results

A. Type 2 Diabetes Biomarker Identification

Three datasets were generated based on the methods described above. The first dataset was an extensive catalog of secretory vesicle content proteins prepared from 6 different human organs. The second dataset contained the corresponding list of secretory vesicle content proteins from 6 rat organs. The third dataset was a catalogue of the steady state secretory vesicle content proteins from each of the 3 experimental systems. The proteins common to the organ secretome database and to any one of the experimental systems were then removed from the experimental system datasets, leaving the secreted proteins more likely to be uniquely expressed by ß-cells or ß-islets. Over two thousand proteins were identified for each species, and on the order of one thousand proteins were identified from the secretory vesicle contents of the rodent ß-cell lines or primary human ß-islets. Between half and ⅔ of these proteins appeared to be also expressed by at least one of the organ secretomes. Removal of these commonly expressed proteins resulted in the ß-cell mass candidate biomarkers. These candidates were then examined in detail to prioritize them for further analysis.

The initial analysis indicated a modest overlap in the net secretome proteins identified from the 3 experimental systems, suggesting only a partial correspondence between the cell line systems and the primary islets. While that finding may not have been surprising, a similarly modest overlap observed between the two cell lines was not expected, and may indicate distinct physiological states for the cell lines.

The proteins identified were assessed for biological function and network and pathway connections through manual literature review and networking software analysis. Relatively stringent criteria were used to denote protein to protein relationships, such as a known direct link between any two proteins be already established, as well as statistical significance that the biological functions or pathways that appear to be over-represented be so by greater than chance alone. The dataset subset that met these criteria contained a considerable number of proteins (152).

Additional assessments for candidate biomarkers prioritization were to establish tissue specificity, which was done using histochemical assessment of the expression of the candidate biomarker proteins in the pancreas and in other organs. This analysis suggested that a significant proportion of the higher ranked candidate biomarkers identified had relatively restricted tissue expression, typically to pancreatic islets, or if they were also expressed in other tissues, they were found with typically lesser expression in the central nervous system. A subset of these markers had also been detected in human body fluids, indicating that these proteins were also secreted. At the end of the analysis, 200 proteins were prioritized and these candidate biomarkers are listed in Table 1 (β cell mass (BCM) markers).

Proteins secreted by the tissues of interest under steady state conditions may change under stress or under dysfunctional states. Secretion of particular proteins under these conditions may become upregulated or down regulated. Furthermore, proteins not normally secreted in steady state may become secreted under stress. Identification of these changes to define biomarker candidates associated with ß-cell and ß-islet function was also performed.

The ß-cell lines and primary human ß-islets were incubated with vehicle or with a glucolipotoxic treatment (described above) for defined periods till the dysfunction described earlier was obtained. Following the treatment, secretory vesicle content sample preparation and proteomic data acquisition and analysis was executed as above. Several hundred proteins that became differentially expressed after the glucolipotoxic treatment were identified. Subtraction of the proteins in common with the organ secretome left 326 non-redundant proteins that were differentially expressed in any of the three experimental systems. The three experimental systems continued to display minimal overlap, even though they were each treated with the same glucolipotoxic treatment and each developed a similar drop in insulin production and induction of apoptosis. After applying the prioritization strategy described above, 129 proteins were selected. The β-cell function (BCF) candidate biomarker proteins and their degree of change after treatment are listed in Table 2.

The pathway analysis supported the interpretation that the 3 experimental systems responded differently to the same stimulus. This indicated that the physiological relevance of the cell line systems might be insufficient to effectively model the human primary tissue. The response by the primary human islets to select the biomarker candidates associated with ß-cell dysfunction was therefore focused on.

A list of biomarker candidates in human plasma that were associated with response to treatment was also developed. All the subjects recruited for this part of the project had type 2 diabetes, and were about to initiate or switch treatment. Plasma was collected prior to the treatment initiation as well as 2 weeks after treatment was initiated. The subjects were then followed for at least 5 months to establish treatment response. A responder was defined as a subject who displayed by treatment's end glycated hemoglobin levels less than 7% without side effects, or had a 1.5% drop of glycated hemoglobin by treatment's end without side effects. Initially the objective was to assess metformin treatment only, which is the first line treatment for type 2 diabetes. The scope of the study was later expanded to allow subjects with other therapies to be included. The number of subjects and their treatment regimes at the time of recruitment are indicated in Table 8.

TABLE 8

Characteristics of subjects used for discovery of treatment monitoring candidate biomarkers

| Treatment option | Number of samples | | |
|---|---|---|---|
| | Baseline | Week_2 | Total |
| Metformin initiation | 12 | 12 | 24 |
| Metformin + Sulfonyurea | 12 | 11 | 23 |
| Metformin + Sulfonyurea + DPP4 inhibitor | 5 | 5 | 10 |
| Metformin + DPP4 inhibitor | 4 | 4 | 8 |
| Metformin + Sulfonyurea + Insulin | 9 | 9 | 18 |
| Total number of samples | 42 | 41 | 83 |

The plasma samples from these subjects were depleted of high abundance proteins and analyzed. The differentially expressed proteins identified were then associated with the available clinical data to identify protein biomarker candidates associated with prediction of response (analysis using the pre-dose samples) or monitoring of response (analysis using the post-treatment initiation samples). The therapeutic efficacy biomarker (TEM) candidates are listed in Table 3.

Approximately 150 proteins were identified that were significantly differentially expressed in at least one treatment response comparison. Differences were observed in the pre-dose samples of the eventual responders versus the eventual non-responders. Furthermore, the differences between responders and non-responders appear to become magnified during the treatment, as more proteins become differentially expressed in the eventual responders compared to the eventual non-responders once treatment has begun.

These analyses indicated that the changes between responders and non-responders become augmented after treatment began, both in the number of proteins differentially expressed per pathway, but also in the introduction of related pathways not induced in the pre-treatment samples.

B. Biomarker Validation

The biomarkers identified as described above were assessed in blood. Human plasma was processed by the three methods described earlier. An aliquot of each subject's plasma sample was depleted of high abundance proteins by affinity chromatography. The remaining material was digested with trypsin and analyzed by a multiplex MRM-MS assay. Another plasma aliquot was used to prepare plasma exosomes by sequential high speed centrifugation. The recovered material was analyzed using the same multiplex MRM-MS assay used on the depleted plasma Finally, a third aliquot of the plasma was used to assess the performance of 23 biomarker candidates by ELISA.

The clinical cohorts selected were designed to describe the spectrum of diabetes disease progression. The early stages of disease progression were represented by normoglycemic controls, which represent non-diabetic healthy subjects, and by subjects with impaired glucose tolerance, which corresponds to pre-diabetic individuals not yet formally diagnosed with type 2 diabetes. Diabetes disease was represented by subjects that have been diagnosed with type 2 diabetes within the last 1.5 years or at least 5 years previously. These two groups represent the early stage and advanced stage diabetics, respectively. Long term (>5 years since diagnosis) type 1 diabetics have also been included in this study. Study plasma was tested for insulin using a commercial ELISA kit. All the subjects had blood draws performed in the AM, after an overnight fast, and thus the insulin reactivity detected most likely represented endogenous levels. An increase in resting insulin concentration was observed in the impaired glucose tolerant, early stage, and advanced diabetics compared to the controls, consistent with type 2 diabetes disease progression.

In order to validate the biomarkers, the level of the biomarkers was determined in samples from subjects. The samples for the analysis were described in Table 7. They comprised morbidly obese individuals with metabolic syndrome, and candidates for bariatric surgery. A subset of these subjects have been diagnosed with T2D and were undergoing therapy at the time of the blood sampling, whereas others appeared to be in a pre-diabetic state. Metabolic syndrome is an umbrella term used to describe what is likely a variety of conditions that all have in common metabolic imbalance that frequently leads to obesity and is often a precursor to T2D. An analysis of these subjects was conducted to evaluate the performance of the candidate biomarkers in a background of extreme metabolic syndrome. The same type of analysis for the non-morbidly obese subjects was conducted (see Table 7): plasma samples were depleted of abundant proteins by chromatography and analyzed using a multiplex MRM-MS assay. Plasma exosome preparations were also made to assess detection of biomarker candidates that may have been beneath the level of detection of the multiplex MRM-MS assay in depleted plasma, and a selection of ELISA assays were performed as well. The performance of the candidate biomarkers is presented in Tables 9-12 which provide the DI value for each marker comparison. If the DI value is above 1 the level of the protein is upregulated for that particular comparison. If the DI value is less than 1, the level of the marker is downregulated for that particular comparison.

TABLE 9

MRM ANALYSIS OF HUMAN PLASMA SAMPLES OF BCM/BCF CANDIDATE BIOMARKERS *Differential expression (DE) thresholds: p-value < 0.05 | q-value < 0.05

| | Established T1D vs Control | | | Established T2D vs Control | | | New T2D vs Control | | |
|---|---|---|---|---|---|---|---|---|---|
| PROTEIN | DI | p-Value | q-Value | DI | p-Value | q-Value | DI | p-Value | q-Value |
| INS_HUMAN | 0.96 | 0.638 | 0.000 | 1.37 | 0.001 | 0.000 | 1.22 | 0.032 | 0.000 |
| USP9X_HUMAN | 1.18 | 0.170 | 0.000 | 0.76 | 0.020 | 0.000 | 0.88 | 0.290 | 0.000 |
| TRI42_HUMAN | 1.27 | 0.008 | 0.000 | 1.61 | 0.000 | 0.000 | 1.20 | 0.035 | 0.000 |
| B4GT1_HUMAN | 0.97 | 0.495 | 0.000 | 1.52 | 0.000 | 0.000 | 1.09 | 0.068 | 0.000 |
| MGAT1_HUMAN | 0.86 | 0.096 | 0.000 | 1.35 | 0.001 | 0.000 | 1.15 | 0.115 | 0.000 |
| ANAG_HUMAN | 0.99 | 0.866 | 0.000 | 0.99 | 0.878 | 0.000 | 1.31 | 0.002 | 0.000 |
| CHKA_HUMAN | 1.26 | 0.019 | 0.000 | 1.56 | 0.000 | 0.000 | 1.27 | 0.013 | 0.000 |
| CADM1_HUMAN | 1.07 | 0.447 | 0.031 | 1.11 | 0.205 | 0.031 | 1.14 | 0.115 | 0.031 |
| DAG1_HUMAN | 1.11 | 0.272 | 0.000 | 1.72 | 0.000 | 0.000 | 1.07 | 0.469 | 0.000 |
| CNTN1_HUMAN | 1.05 | 0.523 | 0.010 | 1.16 | 0.035 | 0.010 | 1.06 | 0.449 | 0.010 |
| SPRL1_HUMAN | 1.09 | 0.083 | 0.000 | 1.15 | 0.004 | 0.000 | 1.02 | 0.714 | 0.000 |
| NCAM1_HUMAN | 0.96 | 0.484 | 0.076 | 1.01 | 0.889 | 0.076 | 0.95 | 0.367 | 0.076 |
| ITM2B_HUMAN | 1.06 | 0.224 | 0.007 | 1.12 | 0.024 | 0.007 | 1.07 | 0.188 | 0.007 |
| DMP4_HUMAN | 0.97 | 0.630 | 0.000 | 1.15 | 0.013 | 0.000 | 1.21 | 0.001 | 0.000 |
| CD59_HUMAN | 0.99 | 0.919 | 0.000 | 1.81 | 0.000 | 0.000 | 1.18 | 0.043 | 0.000 |
| NEO1_HUMAN | 0.99 | 0.802 | 0.000 | 1.16 | 0.008 | 0.000 | 1.04 | 0.484 | 0.000 |
| PTPRJ_HUMAN | 0.99 | 0.881 | 0.004 | 1.06 | 0.148 | 0.004 | 1.08 | 0.053 | 0.004 |
| CBPM_HUMAN | 0.97 | 0.732 | 0.000 | 1.33 | 0.000 | 0.000 | 1.26 | 0.002 | 0.000 |
| SPIT1_HUMAN | 1.02 | 0.750 | 0.006 | 1.12 | 0.038 | 0.006 | 1.07 | 0.175 | 0.006 |
| PVR_HUMAN | 0.94 | 0.268 | 0.000 | 1.15 | 0.012 | 0.000 | 1.06 | 0.286 | 0.000 |
| QPCT_HUMAN | 1.05 | 0.578 | 0.000 | 1.33 | 0.000 | 0.000 | 1.10 | 0.245 | 0.000 |
| SDK1_HUMAN | 1.04 | 0.544 | 0.002 | 1.15 | 0.018 | 0.002 | 0.99 | 0.928 | 0.002 |
| NAAA_HUMAN | 0.99 | 0.913 | 0.020 | 1.09 | 0.105 | 0.020 | 1.02 | 0.735 | 0.020 |
| GALT2_HUMAN | 0.96 | 0.529 | 0.000 | 1.29 | 0.000 | 0.000 | 1.12 | 0.073 | 0.000 |
| LMAN2_HUMAN | 1.00 | 0.958 | 0.000 | 1.37 | 0.000 | 0.000 | 1.11 | 0.123 | 0.000 |
| A4_HUMAN | 1.15 | 0.079 | 0.015 | 1.05 | 0.534 | 0.015 | 1.13 | 0.123 | 0.015 |

TABLE 10

ELISA ANALYSIS OF HUMAN PLASMA SAMPLES OF BCM/BCF CANDIDATE BIOMARKERS Significance Thresholds: p-value < 0.05 | q-value < 0.05

| | IGT vs NGT | | New T2D vs NGT | | Est T2D vs NGT | | New T2D vs IGT | |
|---|---|---|---|---|---|---|---|---|
| PROTEIN | DI | p-Value | DI | p-Value | DI | p-Value | DI | p-Value |
| INS | 1.82 | 0.005 | 2.55 | 0.000 | 2.82 | 0.002 | 1.40 | 0.043 |
| PPY | 0.89 | 0.627 | 2.05 | 0.000 | 1.78 | 0.000 | 2.29 | 0.000 |
| FUT6 | 1.07 | 0.421 | 0.76 | 0.000 | 0.92 | 0.241 | 0.71 | 0.000 |
| CPM | 1.16 | 0.357 | 1.72 | 0.000 | 1.81 | 0.001 | 1.48 | 0.015 |
| SERPINB13 | 1.04 | 0.820 | 0.38 | 0.000 | 0.87 | 0.696 | 0.37 | 0.000 |
| WNT9B | 0.99 | 0.979 | 2.30 | 0.004 | 1.61 | 0.050 | 2.31 | 0.019 |
| STX1A | 1.46 | 0.408 | 3.38 | 0.038 | 1.72 | 0.228 | 2.31 | 0.175 |
| BTC | 0.34 | 0.084 | 1.87 | 0.044 | 0.96 | 0.894 | 5.47 | 0.002 |
| SNAP25 | 0.65 | 0.094 | 0.64 | 0.052 | 1.15 | 0.507 | 0.98 | 0.954 |
| MMP7 | 1.09 | 0.576 | 1.22 | 0.074 | 3.07 | 0.006 | 1.12 | 0.396 |
| CCL20 | 1.57 | 0.322 | 1.62 | 0.090 | 1.98 | 0.055 | 1.03 | 0.923 |
| IGFBP7 | 1.16 | 0.583 | 0.62 | 0.087 | 1.34 | 0.238 | 0.54 | 0.021 |
| SEPT3 | 1.82 | 0.163 | 0.69 | 0.115 | 0.59 | 0.018 | 0.38 | 0.031 |
| SCG5 | 1.74 | 0.121 | 1.81 | 0.125 | 2.86 | 0.089 | 1.04 | 0.917 |
| TNFSF11 | 4.23 | 0.132 | 2.66 | 0.140 | 1.81 | 0.522 | 0.63 | 0.489 |
| REG3A | 0.86 | 0.560 | 1.37 | 0.373 | 1.04 | 0.909 | 1.60 | 0.313 |
| PTPRN | 0.86 | 0.138 | 1.11 | 0.459 | 0.79 | 0.020 | 1.29 | 0.199 |

TABLE 10-continued

ELISA ANALYSIS OF HUMAN PLASMA SAMPLES OF BCM/BCF CANDIDATE
BIOMARKERS Significance Thresholds: p-value < 0.05 | q-value < 0.05

| | | | | | | | | |
|---|---|---|---|---|---|---|---|---|
| IAPP | 2.90 | 0.158 | 1.40 | 0.682 | 2.07 | 0.258 | 0.48 | 0.349 |
| CPE | 1.62 | 0.063 | 0.97 | 0.853 | 0.87 | 0.275 | 0.60 | 0.044 |

| | Est T2D vs IGT | | Est vs New T2D | | T1D vs NGT | | T1D vs IGT | |
|---|---|---|---|---|---|---|---|---|
| PROTEIN | DI | p-Value | DI | p-Value | DI | p-Value | DI | p-Value |
| INS | 1.55 | 0.181 | 1.11 | 0.598 | 0.19 | 0.000 | 0.10 | 0.000 |
| PPY | 1.99 | 0.000 | 0.87 | 0.123 | 1.64 | 0.017 | 1.83 | 0.022 |
| FUT6 | 0.86 | 0.072 | 1.22 | 0.003 | 0.86 | 0.043 | 0.81 | 0.013 |
| CPM | 1.56 | 0.028 | 1.06 | 0.663 | 1.28 | 0.081 | 1.10 | 0.495 |
| SERPINB13 | 0.83 | 0.676 | 2.25 | 0.112 | 1.56 | 0.435 | 1.50 | 0.576 |
| WNT9B | 1.63 | 0.108 | 0.70 | 0.094 | 2.25 | 0.011 | 2.26 | 0.043 |
| STX1A | 1.18 | 0.700 | 0.51 | 0.100 | 2.18 | 0.199 | 1.49 | 0.515 |
| BTC | 2.82 | 0.021 | 0.51 | 0.009 | 0.92 | 0.853 | 2.69 | 0.213 |
| SNAP25 | 1.77 | 0.103 | 1.80 | 0.028 | 1.05 | 0.834 | 1.61 | 0.242 |
| MMP7 | 2.81 | 0.041 | 2.51 | 0.006 | 1.03 | 0.850 | 0.95 | 0.806 |
| CCL20 | 1.26 | 0.564 | 1.22 | 0.448 | 1.05 | 0.897 | 0.67 | 0.355 |
| IGFBP7 | 1.15 | 0.598 | 2.15 | 0.004 | 2.19 | 0.004 | 1.88 | 0.037 |
| SEPT3 | 0.33 | 0.012 | 0.85 | 0.447 | 0.79 | 0.405 | 0.43 | 0.084 |
| SCG5 | 1.65 | 0.428 | 1.58 | 0.308 | 1.42 | 0.241 | 0.82 | 0.559 |
| TNFSF11 | 0.43 | 0.306 | 0.68 | 0.550 | 2.90 | 0.129 | 0.68 | 0.594 |
| REG3A | 1.21 | 0.644 | 0.76 | 0.425 | 1.28 | 0.433 | 1.49 | 0.311 |
| PTPRN | 0.91 | 0.476 | 0.71 | 0.021 | 0.82 | 0.185 | 0.96 | 0.816 |
| IAPP | 0.71 | 0.583 | 1.47 | 0.540 | 1.59 | 0.520 | 0.55 | 0.408 |
| CPE | 0.54 | 0.012 | 0.89 | 0.429 | 0.92 | 0.455 | 0.57 | 0.029 |

TABLE 11

MRM ANALYSIS OF HUMAN EXOSOME SAMPLES OF BCM/BCF CANDIDATE
BIOMARKERS *Differential expression (DE) thresholds: p-value < 0.05 | q-value < 0.05

| | T1D-Established vs Control | | | T2D-Established vs Control | | | T2D-New vs Control | | |
|---|---|---|---|---|---|---|---|---|---|
| PROTEIN | DI | p-value | q-value | DI | p-value | q-value | DI | p-value | q-value |
| EDF1_HUMAN | 128.37 | 0.000 | 0.000 | 0.24 | 0.136 | 0.341 | 33.68 | 0.001 | 0.001 |
| SNAPN_HUMAN | 34.25 | 0.000 | 0.000 | 0.36 | 0.116 | 0.316 | 8.43 | 0.009 | 0.007 |
| NXPH1_HUMAN | 31.14 | 0.000 | 0.000 | 0.45 | 0.324 | 0.505 | 5.19 | 0.080 | 0.035 |
| CDCP1_HUMAN | 18.20 | 0.000 | 0.000 | 5.82 | 0.011 | 0.047 | 8.00 | 0.008 | 0.007 |
| INGR1_HUMAN | 5.94 | 0.002 | 0.001 | 1.03 | 0.957 | 0.738 | 0.71 | 0.621 | 0.196 |
| BTC_HUMAN | 4.60 | 0.007 | 0.003 | 0.75 | 0.617 | 0.662 | 2.49 | 0.131 | 0.052 |
| NCAM1_HUMAN | 4.13 | 0.001 | 0.001 | 1.07 | 0.886 | 0.733 | 2.20 | 0.102 | 0.044 |
| RICBA_HUMAN | 2.98 | 0.002 | 0.001 | 0.99 | 0.986 | 0.742 | 3.28 | 0.002 | 0.002 |
| TM11F_HUMAN | 2.93 | 0.000 | 0.000 | 1.07 | 0.588 | 0.662 | 2.71 | 0.000 | 0.000 |
| MGT4B_HUMAN | 2.89 | 0.000 | 0.000 | 0.91 | 0.534 | 0.662 | 2.75 | 0.000 | 0.000 |
| ERO1B_HUMAN | 2.75 | 0.000 | 0.000 | 0.99 | 0.923 | 0.733 | 2.06 | 0.000 | 0.000 |
| PDYN_HUMAN | 2.57 | 0.000 | 0.000 | 0.85 | 0.237 | 0.419 | 2.24 | 0.000 | 0.000 |
| LTOR2_HUMAN | 2.24 | 0.000 | 0.000 | 0.95 | 0.669 | 0.671 | 2.06 | 0.000 | 0.000 |
| NELL1_HUMAN | 2.03 | 0.000 | 0.000 | 0.97 | 0.781 | 0.733 | 1.71 | 0.000 | 0.000 |
| TCO2_HUMAN | 1.96 | 0.000 | 0.000 | 1.12 | 0.406 | 0.555 | 1.42 | 0.022 | 0.014 |
| PTPRJ_HUMAN | 1.84 | 0.003 | 0.001 | 1.26 | 0.203 | 0.408 | 1.98 | 0.000 | 0.000 |
| CLLD6_HUMAN | 1.78 | 0.009 | 0.003 | 1.11 | 0.669 | 0.671 | 1.34 | 0.309 | 0.110 |
| ATD3B_HUMAN | 1.77 | 0.000 | 0.000 | 0.87 | 0.204 | 0.408 | 2.15 | 0.000 | 0.000 |
| NXPH2_HUMAN | 1.60 | 0.036 | 0.011 | 1.04 | 0.843 | 0.733 | 1.65 | 0.030 | 0.017 |
| VAV3_HUMAN | 1.51 | 0.014 | 0.005 | 0.34 | 0.007 | 0.045 | 1.43 | 0.057 | 0.029 |
| PLXC1_HUMAN | 0.45 | 0.019 | 0.006 | 1.12 | 0.590 | 0.662 | 0.53 | 0.070 | 0.033 |
| CSTF3_HUMAN | 0.34 | 0.000 | 0.000 | 1.04 | 0.744 | 0.722 | 0.71 | 0.020 | 0.013 |
| MCRS1_HUMAN | 1.00 | 0.998 | 0.173 | 0.38 | 0.004 | 0.037 | 0.87 | 0.670 | 0.200 |
| LDLR_HUMAN | 0.96 | 0.825 | 0.151 | 0.56 | 0.001 | 0.037 | 1.12 | 0.542 | 0.181 |
| GHRL_HUMAN | 1.22 | 0.101 | 0.025 | 0.56 | 0.006 | 0.043 | 0.42 | 0.001 | 0.001 |
| NMU_HUMAN | 1.14 | 0.406 | 0.078 | 0.60 | 0.004 | 0.037 | 1.06 | 0.739 | 0.215 |
| AMPD3_HUMAN | 0.29 | 0.067 | 0.018 | 0.62 | 0.401 | 0.555 | 0.38 | 0.156 | 0.060 |
| SLIT3_HUMAN | 1.58 | 0.061 | 0.017 | 0.99 | 0.927 | 0.733 | 2.06 | 0.000 | 0.000 |
| GP158_HUMAN | 1.24 | 0.142 | 0.033 | 0.70 | 0.010 | 0.047 | 1.63 | 0.013 | 0.009 |
| MGAT1_HUMAN | 0.85 | 0.241 | 0.050 | 0.88 | 0.336 | 0.505 | 0.64 | 0.008 | 0.007 |
| OLFM4_HUMAN | 1.51 | 0.234 | 0.050 | 0.035 | 0.126 | 0.03 | 2.07 | 0.033 | 0.018 |
| RENR_HUMAN | 1.25 | 0.030 | 0.010 | 1.19 | 0.107 | 0.316 | 0.80 | 0.039 | 0.021 |
| NAAA_HUMAN | 0.82 | 0.180 | 0.040 | 0.80 | 0.268 | 0.447 | 0.80 | 0.116 | 0.048 |
| MMP14_HUMAN | 1.48 | 0.243 | 0.050 | 1.50 | 0.155 | 0.358 | 0.83 | 0.587 | 0.191 |
| NCEH1_HUMAN | 1.34 | 0.520 | 0.098 | 1.27 | 0.609 | 0.662 | 0.81 | 0.657 | 0.200 |
| TTC37_HUMAN | 3.66 | 0.056 | 0.016 | 1.11 | 0.870 | 0.733 | 0.96 | 0.959 | 0.265 |
| MOGS_HUMAN | 1.57 | 0.115 | 0.028 | 0.66 | 0.228 | 0.419 | 1.07 | 0.843 | 0.239 |

TABLE 11-continued

MRM ANALYSIS OF HUMAN EXOSOME SAMPLES OF BCM/BCF CANDIDATE
BIOMARKERS *Differential expression (DE) thresholds: p-value < 0.05 | q-value < 0.05

| PROTEIN | T1D-Established vs Control | | | T2D-Established vs Control | | | T2D-New vs Control | | |
|---|---|---|---|---|---|---|---|---|---|
| | DI | p-value | q-value | DI | p-value | q-value | DI | p-value | q-value |
| CD59_HUMAN | 1.05 | 0.879 | 0.157 | 1.75 | 0.038 | 0.126 | 0.68 | 0.289 | 0.106 |
| B4GT1_HUMAN | 1.29 | 0.086 | 0.022 | 0.92 | 0.570 | 0.662 | 0.71 | 0.078 | 0.035 |
| USP9X_HUMAN | 1.35 | 0.369 | 0.073 | 0.93 | 0.823 | 0.733 | 0.69 | 0.351 | 0.121 |

TABLE 12

BCM and BCF candidate biomarkers in morbidly obese subjects
*Differential expression (DE) thresholds: p-value < 0.05 | q-value < 0.05

| Gene | BCM | BCF q-Value | High BMI Diabetics vs Pre-diabetics | | Low BMI Diabetics vs Pre-diabetics | |
|---|---|---|---|---|
| | | DI | p-Value | DI | p-Value |
| TRIM42 | 0.000 | 1.57 | 0.000 | 1.44 | 0.000 |
| CHKA | 0.000 | 1.58 | 0.000 | 1.52 | 0.000 |
| CNTN1 | 0.000 | 1.10 | 0.001 | 1.07 | 0.028 |
| PVR | 0.000 | 1.09 | 0.031 | 1.23 | 0.000 |
| INS | 0.000 | 2.13 | 0.009 | 2.98 | 0.002 |
| LCN2 | 0.000 | 0.86 | 0.000 | 1.03 | 0.541 |
| CD59 | 0.000 | 0.89 | 0.036 | 1.09 | 0.167 |
| NGRN | 0.000 | 0.59 | 0.035 | 1.03 | 0.922 |
| TMEM132A | 0.002 | 0.76 | 0.044 | 0.93 | 0.593 |
| B4GALT1 | 0.000 | 1.04 | 0.396 | 1.12 | 0.046 |
| CADM1 | 0.000 | 1.01 | 0.855 | 1.20 | 0.005 |
| CYFIP1 | 0.000 | 1.37 | 0.067 | 0.60 | 0.003 |
| CASC4 | 0.000 | 0.88 | 0.593 | 1.77 | 0.018 |
| STX2 | 0.000 | 1.21 | 0.061 | 1.04 | 0.726 |
| NCAM1 | 0.000 | 0.93 | 0.095 | 1.01 | 0.905 |
| SPINT1 | 0.004 | 1.13 | 0.106 | 1.12 | 0.205 |
| NEO1 | 0.000 | 1.06 | 0.119 | 1.07 | 0.105 |
| VAV3 | 0.000 | 1.30 | 0.136 | 0.97 | 0.872 |
| SV2A | 0.000 | 1.04 | 0.146 | 0.99 | 0.661 |
| USP9X | 0.000 | 0.88 | 0.178 | 0.90 | 0.361 |
| FAM20C | 0.000 | 1.26 | 0.191 | 1.05 | 0.831 |
| MICU1 | 0.004 | 0.83 | 0.214 | 0.92 | 0.636 |
| LAMTOR3 | 0.000 | 1.06 | 0.237 | 1.03 | 0.597 |
| IGFBP7 | 0.005 | 1.15 | 0.264 | 1.26 | 0.125 |
| LMAN2 | 0.000 | 0.85 | 0.284 | 1.02 | 0.912 |
| GALNT2 | 0.000 | 1.06 | 0.295 | 1.08 | 0.232 |
| MGAT1 | 0.000 | 0.96 | 0.312 | 1.05 | 0.370 |
| NAGLU | 0.007 | 1.03 | 0.327 | 0.98 | 0.645 |
| ERO1LB | 0.000 | 1.14 | 0.365 | 1.10 | 0.599 |
| MAP1B | 0.000 | 0.95 | 0.428 | 0.93 | 0.412 |
| MPP2 | 0.001 | 0.91 | 0.440 | 0.75 | 0.052 |
| PTPRJ | 0.000 | 0.98 | 0.448 | 1.04 | 0.304 |
| SFT2D3 | 0.000 | 1.12 | 0.481 | 0.99 | 0.947 |
| SHANK2 | 0.014 | 0.93 | 0.488 | 0.97 | 0.783 |
| ITM2B | 0.011 | 1.07 | 0.496 | 1.01 | 0.955 |
| ENPP4 | 0.000 | 1.14 | 0.500 | 1.09 | 0.713 |
| TLL2 | 0.000 | 0.95 | 0.600 | 0.91 | 0.443 |
| CFDP1 | 0.000 | 1.09 | 0.613 | 1.47 | 0.056 |
| NFASC | 0.000 | 1.08 | 0.620 | 1.17 | 0.407 |
| TMEM123 | 0.000 | 0.91 | 0.636 | 0.82 | 0.373 |
| NGRN | 0.001 | 0.94 | 0.642 | 0.84 | 0.293 |
| APOL2 | 0.001 | 1.01 | 0.666 | 1.06 | 0.070 |
| MGAT4B | 0.013 | 1.04 | 0.762 | 0.95 | 0.681 |
| FGF19 | 0.000 | 1.02 | 0.799 | 0.96 | 0.707 |
| TCN2 | 0.001 | 1.04 | 0.809 | 1.14 | 0.463 |
| PAM | 0.000 | 1.00 | 0.951 | 1.09 | 0.162 |
| SPARCL1 | 0.018 | 1.00 | 0.984 | 1.04 | 0.632 |
| PAPPA2 | 0.005 | 1.00 | 0.987 | 1.01 | 0.928 |
| MIA3 | 0.000 | 1.22 | 0.621 | 0.96 | 0.923 |
| MGAT1 | 0.000 | 1.09 | 0.653 | 0.75 | 0.116 |
| OLFM4 | 0.000 | 0.82 | 0.635 | 2.12 | 0.066 |
| PLSCR3 | 0.000 | 1.15 | 0.588 | 1.23 | 0.418 |
| CFDP1 | 0.000 | 1.09 | 0.722 | 0.80 | 0.347 |
| SHANK2 | 0.000 | 1.07 | 0.867 | 0.63 | 0.246 |
| CHGB | 0.000 | 0.91 | 0.750 | 0.74 | 0.317 |
| B4GALT1 | 0.000 | 1.35 | 0.077 | 1.14 | 0.437 |
| MBP | 0.000 | 0.84 | 0.575 | 0.62 | 0.133 |
| PAPPA2 | 0.000 | 2.10 | 0.099 | 2.16 | 0.087 |
| PAM | 0.000 | 0.73 | 0.052 | 0.76 | 0.083 |
| CD59 | 0.000 | 1.70 | 0.165 | 1.00 | 0.999 |
| LCN2 | 0.002 | 0.92 | 0.670 | 1.21 | 0.307 |
| SLC30A1 | 0.003 | 1.09 | 0.719 | 1.24 | 0.384 |
| SCAMP3 | 0.035 | 0.97 | 0.851 | 1.02 | 0.921 |
| CPE | 0.028 | 1.38 | 0.199 | 0.95 | 0.846 |
| GPRIN1 | 0.010 | 0.94 | 0.723 | 1.00 | 0.980 |
| VAV3 | 0.038 | 0.88 | 0.663 | 1.20 | 0.528 |
| NAGLU | 0.038 | 1.12 | 0.601 | 1.06 | 0.784 |
| USP9X | 0.016 | 1.81 | 0.539 | 0.45 | 0.402 |
| APP | 0.012 | 1.28 | 0.295 | 0.90 | 0.638 |
| PPY | 0.000 | 0.86 | 0.188 | 1.06 | 0.651 |
| CPM | 0.000 | 1.09 | 0.397 | 1.13 | 0.291 |
| BTC | 0.001 | 1.20 | 0.560 | 1.09 | 0.816 |

A subset of the biomarkers was identified to be differentially expressed in both this group of obese subjects and the less obese subjects in the initial verification analysis. There were, however, many biomarkers candidates that were not shared between these two groups. The impact of the excessive obesity was substantial. There were many more biomarker candidates differentially expressed in the morbidly obese to lean comparisons than it the morbidly obese diabetic to morbidly obese pre-diabetic comparisons. The level of the candidate biomarkers was also determined in samples from subjects having type 2 diabetes and about to begin or switch treatments (see Table 8).

Responsiveness to therapy was assessed by A1c levels and blood glucose levels. The 3 largest treatment groups were the subjects on metformin, on metformin and glyburide, and on metformin, glyburide and insulin, and these groups were used to assess the performance of the candidate biomarkers. Changes were identified between responders and non-responders for each treatment (Table 13). It was observed that the number of differentially expressed biomarker candidates increased with each added treatment. Twelve proteins were identified to be differentially expressed between metformin responders and non-responders, 15 in the same comparison for metformin and glyburide, and 21 for metformin, glyburide and insulin.

Worth noting is that insulin family proteins were observed to be differentially expressed between responders and non-responders only for those subjects on metformin, and not for any on the subsequent combination therapies. This results are consistent with advancing disease progression.

TABLE 13

TEM biomarkers on plasma of in morbidly obese subjects
*Differential expression (DE) thresholds: p-value < 0.05 | q-value < 0.05

| Gene | TEM q-Value | Met (Responders vs Non-responders) | | | Met + Gly (Responders vs Non-responders) | | | Met + Gly + Insulin (Responders vs Non-responders) | | |
|---|---|---|---|---|---|---|---|---|---|---|
| | | AUC | DI | p-Value | AUC | DI Median | p-Value | AUC | DI Median | p-Value |
| APOE | 0.000 | 0.66 | 0.77 | 0.027 | 0.72 | 0.70 | 0.034 | 0.64 | 0.78 | 0.105 |
| ACE | 0.002 | 0.75 | 1.54 | 0.011 | 0.57 | 1.04 | 0.859 | 0.78 | 1.56 | 0.044 |
| SAA4 | 0.000 | 0.64 | 0.69 | 0.019 | 0.52 | 0.76 | 0.215 | 0.73 | 0.64 | 0.029 |
| B2M | 0.000 | 0.70 | 1.20 | 0.032 | 0.63 | 1.10 | 0.424 | 0.77 | 1.39 | 0.002 |
| CACNA2D1 | 0.000 | 0.62 | 0.81 | 0.034 | 0.67 | 0.85 | 0.233 | 0.70 | 0.76 | 0.033 |
| DBH | 0.010 | 0.64 | 0.55 | 0.008 | 0.65 | 0.69 | 0.253 | 0.52 | 1.24 | 0.462 |
| CNN2 | 0.009 | 0.63 | 0.50 | 0.029 | 0.61 | 1.50 | 0.383 | .057 | 1.23 | 0.614 |
| LYVE1 | 0.020 | 0.65 | 1.42 | 0.012 | 0.57 | 1.12 | 0.588 | 0.55 | 0.92 | 0.650 |
| IGF2 | 0.029 | 0.71 | 1.37 | 0.031 | 0.58 | 0.95 | 0.804 | 0.51 | 0.95 | 0.791 |
| IGF2R | 0.003 | 0.63 | 1.26 | 0.031 | 0.58 | 0.59 | 0.470 | 0.59 | 0.83 | 0.176 |
| HGFAC | 0.013 | 0.66 | 1.18 | 0.036 | 0.64 | 0.92 | 0.433 | 0.73 | 1.21 | 0.053 |
| ITIH3 | 0.017 | 0.72 | 1.31 | 0.038 | 0.51 | 1.01 | 0.971 | 0.67 | 1.29 | 0.132 |
| ALDOB | 0.000 | 0.51 | 0.91 | 0.681 | 0.74 | 0.42 | 0.009 | 0.74 | 0.50 | 0.020 |
| GPX3 | 0.000 | 0.61 | 1.14 | 0.276 | 0.88 | 0.68 | 0.023 | 0.69 | 0.48 | 0.000 |
| F11 | 0.000 | 0.52 | 0.99 | 0.819 | 0.79 | 0.75 | 0.001 | 0.74 | 1.20 | 0.025 |
| C9 | 0.000 | 0.62 | 1.32 | 0.051 | 0.84 | 1.80 | 0.003 | 0.73 | 1.42 | 0.053 |
| TLN1 | 0.000 | 0.62 | 0.79 | 0.093 | 0.76 | 1.72 | 0.006 | 0.57 | 1.00 | 0.986 |
| PROZ | 0.004 | 0.68 | 1.19 | 0.217 | 0.86 | 0.64 | 0.028 | 0.52 | 0.92 | 0.667 |
| FGG | 0.000 | 0.56 | 1.13 | 0.468 | 0.86 | 2.54 | 0.000 | 0.57 | 0.90 | 0.624 |
| CDH5 | 0.008 | 0.59 | 1.34 | 0.473 | 0.74 | 0.26 | 0.020 | 0.58 | 0.72 | 0.526 |
| CNDP1 | 0.000 | 0.54 | 1.07 | 0.499 | 0.75 | 0.65 | 0.002 | 0.61 | 1.16 | 0.231 |
| FAM20C | 0.001 | 0.61 | 1.17 | 0.685 | 0.79 | 0.20 | 0.003 | 0.59 | 0.50 | 0.156 |
| CA2 | 0.024 | 0.53 | 1.02 | 0.897 | 0.67 | 0.59 | 0.042 | 0.56 | 0.84 | 0.452 |
| C4BPA | 0.006 | 0.53 | 1.06 | 0.583 | 0.71 | 1.38 | 0.048 | 0.63 | 1.16 | 0.326 |
| AFM | 0.004 | 0.54 | 0.96 | 0.655 | 0.71 | 0.72 | 0.027 | 0.61 | 0.88 | 0.337 |
| MASP1 | 0.008 | 0.51 | 0.98 | 0.687 | 0.70 | 0.83 | 0.030 | 0.56 | 0.95 | 0.474 |
| ITIH4 | 0.000 | 0.63 | 1.25 | 0.050 | 0.69 | 1.32 | 0.094 | 0.72 | 1.52 | 0.004 |
| APOB | 0.001 | 0.56 | 0.88 | 0.376 | 0.52 | 0.86 | 0.476 | 0.83 | 0.58 | 0.003 |
| SERPINA4 | 0.000 | 0.55 | 1.09 | 0.478 | 0.68 | 0.79 | 0.156 | 0.76 | 0.55 | 0.000 |
| MBL2 | 0.005 | 0.54 | 0.90 | 0.665 | 0.63 | 0.66 | 0.231 | 0.64 | 0.54 | 0.048 |
| PROCR | 0.020 | 0.52 | 0.94 | 0.702 | 0.57 | 0.89 | 0.638 | 0.51 | 0.61 | 0.025 |
| BTD | 0.005 | 0.51 | 1.03 | 0.846 | 0.71 | 0.61 | 0.356 | 0.61 | 0.54 | 0.004 |
| APOC4 | 0.000 | 0.56 | 0.96 | 0.862 | 0.63 | 0.58 | 0.132 | 0.82 | 0.23 | 0.000 |
| F10 | 0.002 | 0.53 | 0.98 | 0.901 | 0.70 | 0.78 | 0.244 | 0.62 | 0.60 | 0.009 |
| PGLYRP2 | 0.010 | 0.54 | 1.09 | 0.398 | 0.54 | 0.91 | 0.540 | 0.62 | 0.75 | 0.035 |
| ATRN | 0.008 | 0.54 | 1.07 | 0.484 | 0.52 | 0.98 | 0.893 | 0.57 | 0.75 | 0.021 |
| EFEMP1 | 0.002 | 0.61 | 1.09 | 0.489 | 0.61 | 1.22 | 0.264 | 0.83 | 1.46 | 0.018 |
| GPLD1 | 0.002 | 0.54 | 1.04 | 0.590 | 0.68 | 0.80 | 0.056 | 0.70 | 0.78 | 0.018 |
| COL6A3 | 0.000 | 0.63 | 1.05 | 0.618 | 0.61 | 1.21 | 0.164 | 0.76 | 1.45 | 0.003 |
| SERPINA7 | 0.008 | 0.53 | 1.02 | 0.861 | 0.60 | 1.15 | 0.331 | 0.58 | 0.76 | 0.034 |

Additional analyses of the markers identified 30 markers that have individual discrimination power, defined as being able to discriminate between two cohorts with an accuracy of 75% or greater. Specifically, and as described above, samples were obtained from control subjects (e.g., normal glucose tolerant (NGT) subjects, pre-diabetic subjects (e.g., subjects having impaired glucose tolerance), subjects diagnosed as having type 2 diabetes in the previous 18 months (nT2D) and subjects having type 2 diabetes and a complication associated with type 2 diabetes, such as diabetic neuropathy, retinopathy, nephropathy, cardiovascular disease (eT2D) and the level of each of the markers listed in Tables 1-3 was determined. Pairwise comparisons of the level of each marker in NGT subjects and; IGT subjects; nT2D subjects; eT2D; and a combination of nT2D and eT2D subjects (All T2D) were performed and the area under the curve for each marker was calculated. Similarly, pairwise comparisons of the level of each marker in IGT subjects and; nT2D subjects; eT2D; and a combination of nT2D and eT2D subjects (All T2D) were performed and the area under the curve for each marker was calculated. The results of these analyses are shown in Table 14. Therefore a substantial number of well performing candidates was identified. For most comparison, multiple biomarker candidates with good performance indicators were identified.

TABLE 14

Area Under the Curve (AUC) for Single Markers.

| Marker | NGT vs | | | | IGT vs | | |
|---|---|---|---|---|---|---|---|
| | IGT | nT2D | eT2D | All T2D | nT2D | eT2D | All T2D |
| USP9X | 0.718 | — | — | — | — | — | — |
| DAG1 | — | — | 0.989 | — | — | 0.947 | — |
| SEPT3 | — | — | 0.732 | 0.814 | — | 0.834 | 0.824 |
| PTPRJ | — | — | — | 0.774 | — | 0.774 | 0.923 |
| CPM | — | 0.876 | 0.785 | 0.814 | — | 0.742 | 0.746 |
| SERPINB13 | — | 0.885 | — | — | 0.940 | — | — |
| LDLR | — | — | 0.802 | 0.835 | — | — | — |
| MMP7 | — | — | 0.884 | 0.838 | — | 0.847 | — |
| BTC | — | 0.690 | — | — | 0.968 | 0.833 | 0.798 |
| PPY | — | 0.907 | 0.881 | 0.923 | 0.961 | 0.937 | 0.945 |
| INS | — | 0.983 | 0.802 | 0.818 | — | — | — |
| CSTF3 | — | 0.766 | — | — | — | — | — |
| NELL1 | — | 0.741 | — | — | — | — | — |
| SLIT3 | — | 0.861 | — | — | 0.812 | — | — |

TABLE 14-continued

Area Under the Curve (AUC) for Single Markers.

| Marker | NGT vs | | | | IGT vs | | |
|---|---|---|---|---|---|---|---|
| | IGT | nT2D | eT2D | All T2D | nT2D | eT2D | All T2D |
| LAMTOR2 | — | 0.850 | — | — | 0.813 | — | — |
| MGAT4B | — | 0.826 | — | — | 0.786 | — | — |
| TMPRSS11F | — | 0.822 | — | — | 0.741 | — | — |
| ATAD3B | — | 0.765 | — | — | 0.751 | — | — |
| PTPRN | — | — | 0.730 | — | — | — | — |
| WNT9B | — | 0.794 | — | 0.513 | — | — | 0.705 |
| FUT6 | — | 0.844 | — | 0.572 | 0.885 | — | 0.591 |
| B4GALT1 | — | — | — | 0.945 | — | — | 0.885 |
| FAM20C | — | — | — | — | — | — | 0.878 |
| CNTN1 | — | — | — | — | — | — | 0.758 |
| MGAT1 | — | 0.915 | — | — | — | — | — |
| STX1A | — | 0.828 | — | — | — | — | — |
| NMU | — | — | 0.782 | 0.877 | — | — | — |
| CD59 | — | — | — | 0.980 | — | — | 0.903 |
| CASR | — | — | — | 0.898 | — | — | — |
| CPE | 0.590 | — | — | — | — | 0.850 | 0.875 |

The ability of these individual biomarkers to act in combination, as a panel, was also assessed. This preliminary panel analysis focused on identifying combinations that improved discrimination accuracy, but also used the smallest possible number of biomarkers. As shown in Table 15, small panels of proteins that were able to accurately discriminate between each of the disease progression cohorts were successfully identified. The area under the curve (AUC) for various combinations of the markers listed in Tables 1-3 was also determined. The results of these analyses are shown in Table 15.

TABLE 15

Area Under the Curve (AUC) for Marker Combinations.

| Markers | Proteins in panel | NGT vs | | | | IGT vs | | |
|---|---|---|---|---|---|---|---|---|
| | | IGT | nT2D | eT2D | All T2D | nT2D | eT2D | All T2D |
| INS; USPX | 2 | 0.774 | — | — | — | — | — | — |
| INS; SERPINB13 | 2 | — | — | — | — | 0.998 | — | — |
| BTC; MMP7; PPY | 3 | — | — | — | — | — | 0.999 | — |
| INS; SERPINB13 | 2 | — | 0.998 | — | — | — | — | — |
| CPM; INS; MMP7; LDLR | 4 | — | — | 0.948 | — | — | — | — |
| PPY; SEPT3; PTPRJ | 3 | — | — | — | — | — | — | 0.952 |
| PPY; DAG1 | 2 | — | — | — | 0.986 | — | — | — |

The biomarker candidates associated with pancreatic function and disease progression were also evaluated in plasma from morbidly obese type 2 diabetics or pre-diabetics. Fewer proteins overall (13 vs 30) compared to the initial, less obese, cohorts were found to have acceptable individual discrimination power. However, the list of candidate biomarkers from both cohorts overlapped, with only 2 of the 13 better biomarker candidates from the obese subject dataset were detected only in the obese subjects. This suggests that the bulk of the biomarker candidates identified with good discriminatory power had similar performance in both cohorts. While this suggests that these biomarker candidates could be relevant in multiple populations, there were also important differences. One of these appears to be that combinations containing more proteins were necessary to separate the diabetic from the pre-diabetic subjects from the obese cohorts. For example, a combination of 5 proteins was required to generate a panel able to discriminate morbidly obese diabetics from morbidly obese pre-diabetics with an accuracy of 0.826. By comparison, non-morbidly obese pre-diabetics could be distinguished from diabetics of comparable BMI with an accuracy of 0.998 using a combination of only 3 proteins. This suggests that it might be more difficult to separate the obese diabetics from the obese pre-diabetics, which is why more panel members were required and even then these additional panel members produced an overall less accurate combination. Variability among the cohort subjects may be a factor affecting panel performance, since the morbidly obese subjects included had widely varying BMI values, ranging from 35 to 70. Once the subjects were sorted into two groups, one containing subjects with BMI of up to 40, and the other subjects with BMI above 40, the best 5 protein panel composition became different for each of these groups, and the best panel performance rose from 0.826 to 0.843 and 0.889, respectively (Table 16).

TABLE 16

BCM|BCF|TEM High BMI [Diabetics vs Non Diabetics]

| PANEL COMPOSITION | #PROTEINS | AUC |
|---|---|---|
| CD59 | CNTN1 | MGAT1 | TRIM42 | USP9X | 5 | 0.889 |
| CD59 | CHKA | CNTN1 | TRIM42 | USP9X | 5 | 0.881 |
| CD59 | CNTN1 | PTPRJ | TRIM42 | USP9X | 5 | 0.879 |
| B4GALT1 | CD59 | CNTN1 | TRIM42 | USP9X | 5 | 0.874 |
| CD59 | CNTN1 | TRIM42 | USP9X | BTC | 5 | 0.872 |
| CD59 | CNTN1 | TRIM42 | USP9X | CPM | 5 | 0.872 |
| CD59 | CNTN1 | TRIM42 | USP9X | PPY | 5 | 0.871 |
| CD59 | CNTN1 | FAM20C | TRIM42 | USP9X | 5 | 0.871 |
| CD59 | CNTN1 | TRIM42 | USP9X | 4 | 0.871 |

TABLE 16-continued

BCM|BCF|TEM High BMI [Diabetics vs Non Diabetics]

| PANEL COMPOSITION | #PROTEINS | AUC |
|---|---|---|
| CD59 | CNTN1 | TRIM42 | USP9X | INS | 5 | 0.871 |
| CNTN1 | MGAT1 | PTPRJ | TRIM42 | USP9X | 5 | 0.868 |
| CD59 | CHKA | CNTN1 | MGAT1 | USP9X | 5 | 0.867 |
| CHKA | CNTN1 | MGAT1 | TRIM42 | USP9X | 5 | 0.867 |
| B4GALT1 | CHKA | CNTN1 | TRIM42 | USP9X | 5 | 0.867 |
| B4GALT1 | CNTN1 | PTPRJ | TRIM42 | USP9X | 5 | 0.867 |
| CNTN1 | MGAT1 | TRIM42 | USP9X | INS | 5 | 0.865 |
| CHKA | CNTN1 | PTPRJ | TRIM42 | USP9X | 5 | 0.865 |
| B4GALT1 | CNTN1 | MGAT1 | TRIM42 | USP9X | 5 | 0.863 |
| CNTN1 | FAM20C | MGAT1 | TRIM42 | USP9X | 5 | 0.863 |
| CNTN1 | MGAT1 | TRIM42 | USP9X | BTC | 5 | 0.861 |
| CNTN1 | MGAT1 | TRIM42 | USP9X | CPM | 5 | 0.860 |
| CD59 | CHKA | CNTN1 | FAM20C | USP9X | 5 | 0.860 |
| CNTN1 | MGAT1 | TRIM42 | USP9X | 4 | 0.860 |
| CD59 | CNTN1 | PTPRJ | TRIM42 | INS | 5 | 0.860 |
| CD59 | CHKA | CNTN1 | PTPRJ | USP9X | 5 | 0.859 |

TABLE 16-continued

BCM|BCF|TEM High BMI [Diabetics vs Non Diabetics]

| PANEL COMPOSITION | #PROTEINS | AUC |
|---|---|---|
| CNTN1 \| MGAT1 \| TRIM42 \| USP9X \| PPY | 5 | 0.859 |
| CD59 \| CNTN1 \| MGAT1 \| PTPRJ \| TRIM42 | 5 | 0.859 |
| B4GALT1 \| CNTN1 \| FAM20C \| TRIM42 \| USP9X | 5 | 0.858 |
| B4GALT1 \| CNTN1 \| TRIM42 \| USP9X \| INS | 5 | 0.857 |
| B4GALT1 \| CNTN1 \| TRIM42 \| USP9X \| PPY | 5 | 0.857 |
| CD59 \| CHKA \| CNTN1 \| USP9X \| PPY | 5 | 0.856 |
| B4GALT1 \| CNTN1 \| TRIM42 \| USP9X | 4 | 0.856 |
| CHKA \| CNTN1 \| FAM20C \| MGAT1 \| USP9X | 5 | 0.855 |
| CD59 \| CHKA \| CNTN1 \| USP9X \| BTC | 5 | 0.855 |
| B4GALT1 \| CNTN1 \| TRIM42 \| USP9X \| CPM | 5 | 0.855 |
| CNTN1 \| PTPRJ \| TRIM42 \| USP9X \| INS | 5 | 0.855 |
| CD59 \| CHKA \| CNTN1 \| USP9X \| CPM | 5 | 0.855 |
| CD59 \| CHKA \| CNTN1 \| USP9X \| INS | 5 | 0.854 |
| B4GALT1 \| CNTN1 \| TRIM42 \| USP9X \| BTC | 5 | 0.854 |
| B4GALT1 \| CD59 \| CHKA \| CNTN1 \| USP9X | 5 | 0.853 |
| CD59 \| CHKA \| CNTN1 \| USP9X | 4 | 0.853 |
| CNTN1 \| PTPRJ \| TRIM42 \| USP9X \| BTC | 5 | 0.853 |
| CNTN1 \| PTPRJ \| TRIM42 \| USP9X \| PPY | 5 | 0.853 |
| CD59 \| CNTN1 \| FAM20C \| PTPRJ \| TRIM42 | 5 | 0.853 |
| CD59 \| CHKA \| CNTN1 \| PTPRJ \| TRIM42 | 5 | 0.853 |
| B4GALT1 \| CHKA \| CNTN1 \| MGAT1 \| USP9X | 5 | 0.852 |
| CNTN1 \| PTPRJ \| TRIM42 \| USP9X | 4 | 0.852 |
| CNTN1 \| FAM20C \| PTPRJ \| TRIM42 \| USP9X | 5 | 0.852 |
| CHKA \| CNTN1 \| MGAT1 \| PTPRJ \| USP9X | 5 | 0.852 |
| CD59 \| CNTN1 \| PTPRJ \| TRIM42 \| PPY | 5 | 0.852 |
| CNTN1 \| PTPRJ \| TRIM42 \| USP9X \| CPM | 5 | 0.852 |
| B4GALT1 \| CHKA \| CNTN1 \| FAM20C \| USP9X | 5 | 0.851 |
| CHKA \| CNTN1 \| MGAT1 \| USP9X \| INS | 5 | 0.851 |
| CD59 \| CHKA \| MGAT1 \| TRIM42 \| USP9X | 5 | 0.851 |
| CD59 \| CNTN1 \| PTPRJ \| TRIM42 \| BTC | 5 | 0.850 |
| B4GALT1 \| CD59 \| CNTN1 \| PTPRJ \| TRIM42 | 5 | 0.850 |
| CD59 \| CNTN1 \| PTPRJ \| TRIM42 | 4 | 0.850 |
| CD59 \| CNTN1 \| PTPRJ \| TRIM42 \| CPM | 5 | 0.850 |

Example II. Determination of the Level of One or More Biomarkers in a Subject Sample A biological sample (e.g., serum, saliva) is obtained from a subject and the level of one or more of the markers listed in Tables 1-3 is determined by mass spectrometry to determine (e.g., whether a subject has or will develop type 2 diabetes, whether the subject has or will develop impaired glucose tolerance, whether the subject will develop a type 2 diabetes-associated complication, whether the subject having impaired glucose tolerance and/or type 2 diabetes will respond to a therapy). Briefly, the sample is digested with trypsin to generate peptides. The peptides are then separated by strong cation exchange chromatography (SCX) into three fractions. Each of the three fractions per sample is analyzed by reversed phase liquid chromatography, coupled by electrospray to a Waters QTOF mass spectrometer (LC-MS). Components are detected and matched across all samples and compared for relative peak intensity. Peak intensity is normalized. The level of the one or more markers in the sample is compared to a level of the one or more markers in a control sample and a difference in the level of the one or more markers in the subject sample as compared to the level of the one or more markers in the control sample indicates that the subject has or will develop impaired glucose tolerance.

EQUIVALENTS

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2, etc., or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

INCORPORATION BY REFERENCE

The contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

We claim:

1. A method for monitoring the effectiveness of a diabetic treatment in a subject having type 2 diabetes, the method comprising
determining the level of carboxypeptidase M (CPM), insulin-1 (INS), matrilysin (MMP7), and low-density lipoprotein receptor (LDLR) in a first fluid sample(s) obtained from the subject prior to the initiation of the treatment,
wherein the determining of the level of CPM, INS, MMP7, and LDLR in the first fluid sample(s) is performed using mass spectrometry or immunoassay;
determining the level of CPM, INS, MMP7, and LDLR in a second fluid sample(s) obtained from the subject after the treatment has been administered,
wherein the determining of the level of CPM, INS, MMP7, and LDLR in the second fluid sample(s) is performed using mass spectrometry or immunoassay; and
comparing the level of CPM, INS, MMP7, and LDLR in the first sample(s) with a level of CPM, INS, MMP7, and LDLR in the second sample(s), wherein a lower level of CPM, INS, and MMP7, and a higher level of LDLR in the second sample(s) as compared to the level of CPM, INS, MMP7, and LDLR in the first sample(s) indicates that the subject is responding to the diabetic treatment, thereby monitoring the effectiveness of the treatment in the subject.

2. The method of claim 1, further comprising determining one or more of the level of the hemoglobin A1c (HbA1c) level, and the fasting plasma glucose level in a sample(s) from the subject.

3. The method of claim 1, further comprising determining the level of one or more markers selected from the group consisting of probable ubiquitin carboxyl-terminal hydrolase FAF-X (USP9X), similar to dystroglycan precursor (DAG1), neuronal-specific septin-3 (SEPT3), receptor-type tyrosine-protein phosphatase eta (PTPRJ), Serpin B13 (SERPINB13), probetacellulin (BTC), and pancreatic icosa-peptide (PPY) in a sample(s) obtained from the subject.

4. The method of claim 1, further comprising determining the level of one or more markers selected from the group consisting of cleavage stimulation factor subunit 3 (CSTF3), protein kinase C-binding protein NELL1 (NELL1), slit homolog 3 (SLIT3), regulator complex protein LAMTOR 2 (LAMTOR2), alpha-1,3-mannosyl-glycoprotein 4-beta-acetylglucosaminyl transferase B (MGAT4B), transmembrane protease serine 11F (TMPRSS11F), ATPase family AAA domain-containing protein 3B (ATAD3B), receptor-type tyrosine-protein phosphatase-like N (PTPRN), protein Wnt-9b (WNT9B), alpha-(1,3)-fucosyltransferase (FUT6), beta-1,4-galactosyltransferase 1 (B4GALT1), family with sequence similarity 20, member C (FAM20C), contactin-1 (CNTN1), alpha-1,3-mannosyl-glycoprotein 2-beta-acetylg-lucosaminyl transferase (MGAT1), syntaxin-1A (STXIA), neuromedin U (NMU), CD59 glycoprotein (CD59), peripheral plasma membrane protein CASK (CASR), and carboxypeptidase E (CPE) in a sample(s) obtained from the subject.

5. The method of claim 1, wherein the fluid sample(s) is a blood sample(s).

6. The method of claim 1, wherein the subject is a non-human mammal.

7. The method of claim 1, wherein the subject is human.

8. The method of claim 1, wherein the combination of CPM, INS, MMP7, and LDLR has an area under the curve (AUC) of greater than about 0.70.

\* \* \* \* \*